(12) United States Patent
Moon et al.

(10) Patent No.: US 9,023,638 B2
(45) Date of Patent: May 5, 2015

(54) MICROVESSELS, MICROPARTICLES, AND METHODS OF MANUFACTURING AND USING THE SAME

(71) Applicant: Illumina, Inc., San Diego, CA (US)

(72) Inventors: John A. Moon, San Diego, CA (US); M. Shane Bowen, La Jolla, CA (US); Ryan C. Smith, San Diego, CA (US); Michel Perbost, San Diego, CA (US); Michal Lebl, San Diego, CA (US); Steven H. Modiano, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/969,050

(22) Filed: Aug. 16, 2013

(65) Prior Publication Data

US 2014/0100123 A1 Apr. 10, 2014

Related U.S. Application Data

(62) Division of application No. 12/916,242, filed on Oct. 29, 2010, now Pat. No. 8,524,450.

(60) Provisional application No. 61/256,582, filed on Oct. 30, 2009.

(51) Int. Cl.
*G01N 33/50* (2006.01)
*B01J 19/00* (2006.01)
(Continued)

(52) U.S. Cl.
CPC ....... *G01N 33/50* (2013.01); *B01J 2219/00596* (2013.01); *B01J 19/0046* (2013.01); *B01J 2219/00306* (2013.01);
(Continued)

(58) Field of Classification Search
None
See application file for complete search history.

(56) References Cited

U.S. PATENT DOCUMENTS 4,528,159 A 7/1985 Liston
4,751,186 A 6/1988 Baisch et al.
(Continued)

FOREIGN PATENT DOCUMENTS

WO 9745556 12/1997
WO 0178889 A2 10/2001
WO 2008063227 5/2008

OTHER PUBLICATIONS

Jason R. Dorvee, et al. "Digital microfluidics and delivery of molecular payloads with magnetic porous silicon chaperones." Dalton Transactions, 6, Feb. 14, 2008, pp. 721-730.
(Continued)

*Primary Examiner* — Betty Forman
(74) *Attorney, Agent, or Firm* — Small Patent Law Group; Dean Small; Jason Gross

(57) ABSTRACT

A plurality of isolated microvessels including a plurality of encoded microvessels each having a microbody and a reservoir core. The microbody is configured to separate a biological or chemical substance in the reservoir core from an ambient environment surrounding the microbody. The microbody includes a transparent material that at least partially surrounds the reservoir core and facilitates detection of an optical characteristic of the substance within the reservoir core. The microbody of each microvessel includes an identifiable code that distinguishes individual microvessels of the plurality of encoded microvessels from each other. The plurality of isolated microvessels also includes a plurality of compartments each configured to separate individual microvessels of the plurality of encoded microvessels from each other.

21 Claims, 29 Drawing Sheets

(51) Int. Cl.
*B01L 3/00* (2006.01)
*C40B 20/04* (2006.01)
*G01N 21/25* (2006.01)
*G01N 21/64* (2006.01)
*G01N 21/01* (2006.01)
*G01N 35/00* (2006.01)

(52) U.S. Cl.
CPC ............... *B01J 2219/00511* (2013.01); *B01J 2219/0052* (2013.01); *B01J 2219/00524* (2013.01); *B01J 2219/00545* (2013.01); *B01J 2219/00576* (2013.01); *B01J 2219/00585* (2013.01); *B01J 2219/00673* (2013.01); *B01J 2219/00702* (2013.01); *B01J 2219/0072* (2013.01); *B01L 3/502761* (2013.01); *B01L 3/5082* (2013.01); *B01L 3/50857* (2013.01); *B01L 3/5088* (2013.01); *B01L 3/545* (2013.01); *C40B 20/04* (2013.01); *G01N 21/253* (2013.01); *G01N 21/6452* (2013.01); *G01N 21/01* (2013.01); *G01N 35/00732* (2013.01)

(56) References Cited

U.S. PATENT DOCUMENTS

| | | | |
|---|---|---|---|
| 5,359,184 | A | 10/1994 | Froehlich et al. |
| 5,518,923 | A | 5/1996 | Berndt et al. |
| 5,639,603 | A | 6/1997 | Dower et al. |
| 6,096,496 | A | 8/2000 | Frankel |
| 6,375,898 | B1 | 4/2002 | Ulrich |
| 6,489,103 | B1 | 12/2002 | Griffiths |
| 6,908,737 | B2 | 6/2005 | Ravkin |
| 7,106,513 | B2 | 9/2006 | Moon |
| 7,126,755 | B2 | 10/2006 | Moon |
| 7,190,522 | B2 | 3/2007 | Moon |
| 7,349,158 | B2 | 3/2008 | Moon |
| 7,375,890 | B2 | 5/2008 | Putnam |
| 7,399,643 | B2 | 7/2008 | Moon |
| 7,433,123 | B2 | 10/2008 | Putnam |
| 7,441,703 | B2 | 10/2008 | Moon |
| 7,508,608 | B2 | 3/2009 | Kersey |
| 7,602,952 | B2 | 10/2009 | Kersey |
| 7,604,173 | B2 | 10/2009 | Kersey |
| 7,619,819 | B2 | 11/2009 | Moon |
| 7,623,624 | B2 | 11/2009 | Moon |
| 7,659,983 | B2 | 2/2010 | Moon |
| 7,830,575 | B2 | 11/2010 | Moon |
| 7,872,804 | B2 | 1/2011 | Moon |
| 7,901,630 | B2 | 3/2011 | Putnam |
| 7,923,260 | B2 | 4/2011 | Moon |
| 8,081,792 | B2 | 12/2011 | Moon |
| 2002/0012909 | A1 | 1/2002 | Plaksin |
| 2002/0031783 | A1 | 3/2002 | Empedocles |
| 2002/0045272 | A1* | 4/2002 | McDevitt et al. ............ 436/518 |
| 2003/0124564 | A1 | 7/2003 | Trau |
| 2003/0129654 | A1 | 7/2003 | Ravkin |
| 2003/0203390 | A1 | 10/2003 | Kaye |
| 2004/0126875 | A1 | 7/2004 | Putnam et al. |
| 2004/0197819 | A1 | 10/2004 | Yang et al. |
| 2004/0209376 | A1 | 10/2004 | Natan |
| 2005/0003556 | A1 | 1/2005 | Nagasawa et al. |
| 2005/0037406 | A1 | 2/2005 | De La Torre-Bueno et al. |
| 2005/0085708 | A1 | 4/2005 | Fauver et al. |
| 2005/0227252 | A1 | 10/2005 | Moon |
| 2005/0270603 | A1 | 12/2005 | Putnam |
| 2006/0012130 | A1 | 1/2006 | Vann |
| 2006/0019264 | A1* | 1/2006 | Attiya et al. ...................... 435/6 |
| 2006/0057729 | A1 | 3/2006 | Moon |
| 2006/0063271 | A1 | 3/2006 | Putnam |
| 2006/0088928 | A1 | 4/2006 | Sweet et al. |
| 2006/0134324 | A1 | 6/2006 | Putnam |
| 2006/0160208 | A1 | 7/2006 | Putnam |
| 2007/0053800 | A1* | 3/2007 | Lehto ............................ 422/102 |
| 2008/0003571 | A1 | 1/2008 | McKernan et al. |
| 2008/0176216 | A1* | 7/2008 | Doyle et al. ..................... 435/5 |
| 2009/0220789 | A1 | 9/2009 | DeSimone et al. |
| 2009/0226891 | A2 | 9/2009 | Nova et al. |
| 2009/0298712 | A1* | 12/2009 | Kiryukhin et al. .............. 506/16 |

OTHER PUBLICATIONS

Ji-Ho Park, et al. "Local Heating of Discrete Droplets Using Magnetic Porous Silicon-Based Photonic Crystals," J. Am. Chem. Soc. 2006, 128, pp. 7938-7946.

J. Christopher Thomas, et al. "Delivery of nanogram payloads using magnetic porous silicon microcarriers." Lab Chip, 2006, 6, pp. 782-787.

Supplementary Search Report, mailed May 7, 2013, for European Patent Application No. EP 10 82 7565.

Pommersheim et al "Immobilization of enzymes by multilayer microcapsules" Macrolm Chem. Phys. 1994, 195: 1557-1567.

International Search Report and Written Opinion of PCT/US2010/584829, filed Oct. 29, 2010, 10 pgs.

U.S. Appl. No. 60/410,541, filed Sep. 12, 2002, Improved Digital Optical Identification Element.

U.S. Appl. No. 60/405,087, filed Aug. 20, 2002, Digital Optical Identification Element.

Morrison, et al., Nanoliter high throughput quantitative PCR, Nucleic Acids Research, 2006, vol. 34, No. 18.

Margulies, et al., Genome sequencing in microfabricated high-density picolitre reactors, vol. 437, Sep. 15, 2005.

* cited by examiner

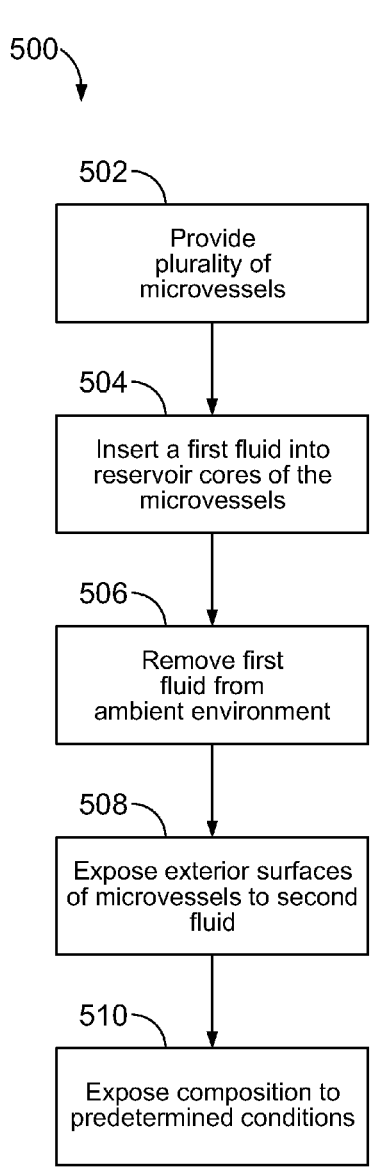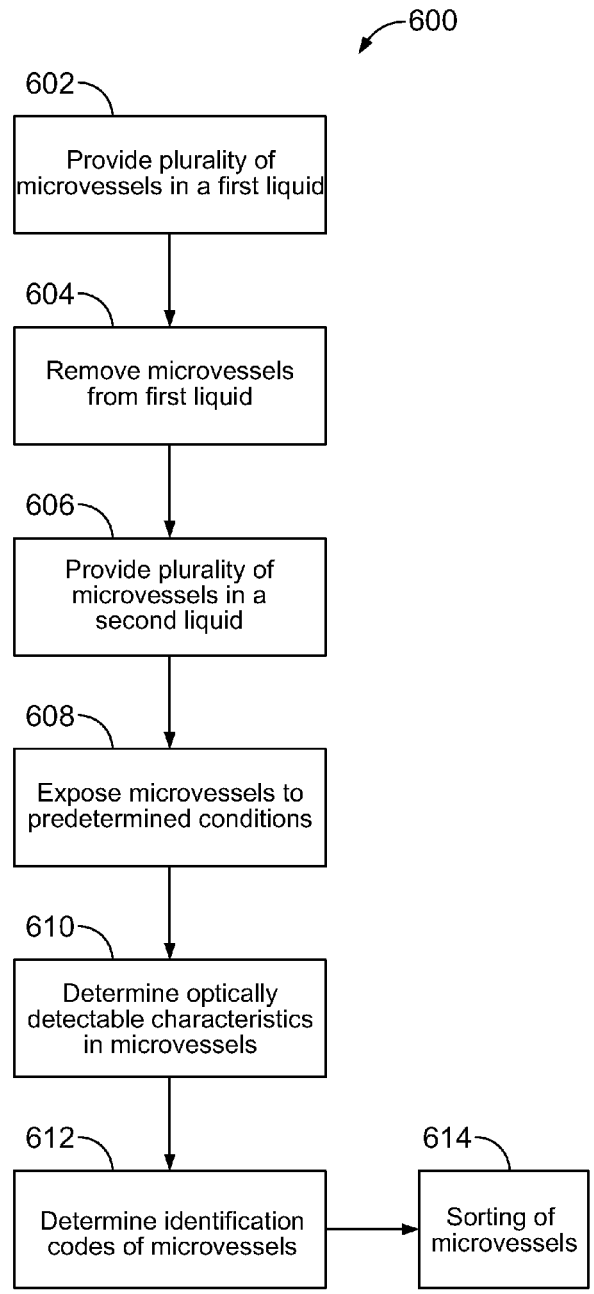
FIG. 23
FIG. 25

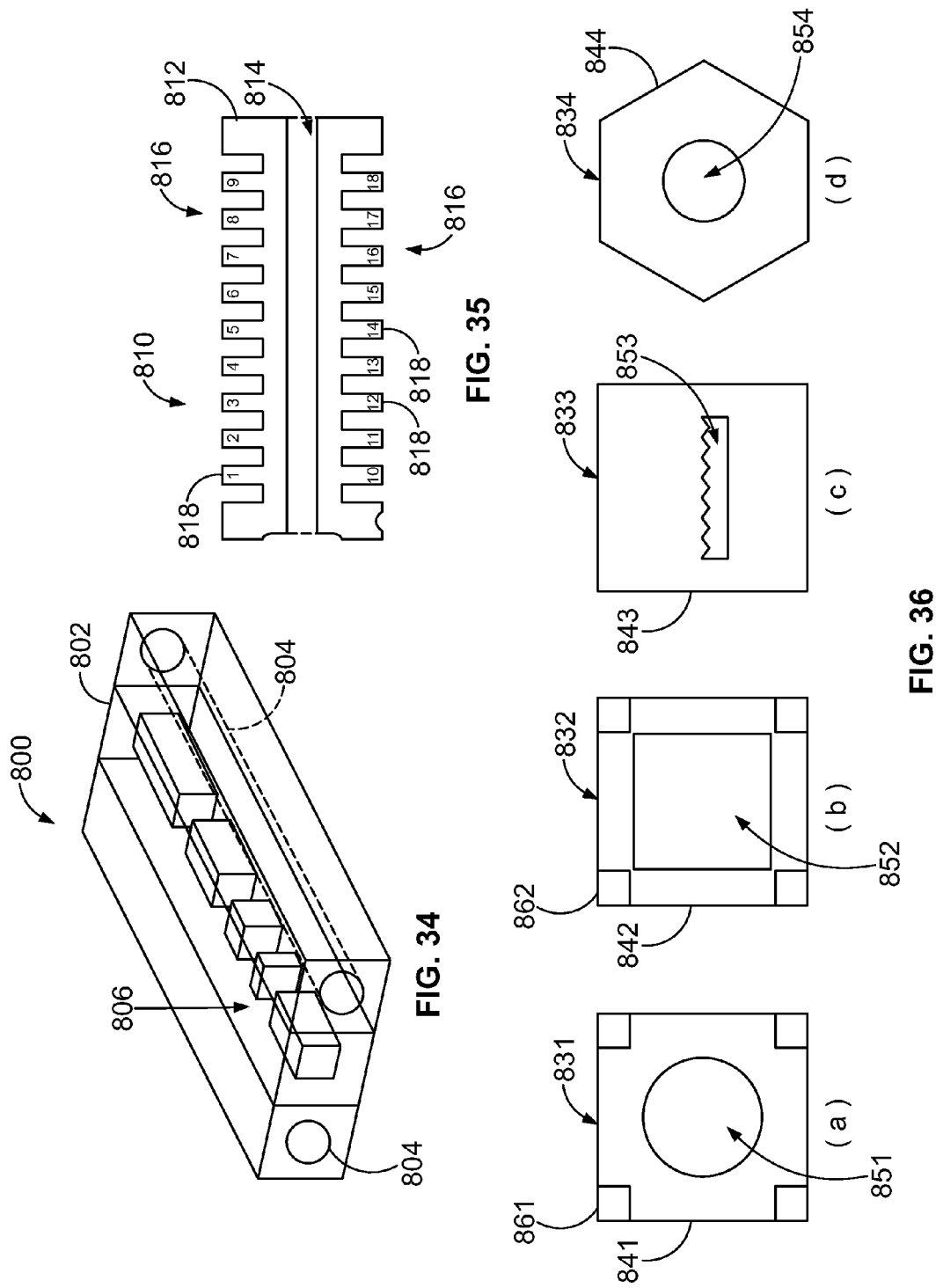

MICROVESSELS, MICROPARTICLES, AND METHODS OF MANUFACTURING AND USING THE SAME

CROSS-REFERENCES TO RELATED APPLICATIONS

The present application is a divisional of U.S. application Ser. No. 12/916,242, filed on Oct. 29, 2010, which claims the benefit of U.S. Provisional Application No. 61/256,582, filed Oct. 30, 2009. Each of the above applications is incorporated by reference in its entirety.

BACKGROUND OF THE INVENTION

Embodiments of the present invention relate generally to microparticles and more particularly, to microvessels that separate substances, such as biological or chemical substances, from an ambient environment.

Various protocols in biological or chemical research involve performing a large number of controlled chemical reactions within solutions or mixtures that are isolated from each other and/or from an ambient environment. Such isolated solutions or mixtures (i.e., reaction volumes) may be formed in assays by using test tubes, microcentrifuge tubes, and wells of microplates. For example, in multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Generally, in assays such as the above, it is desirable to observe as many chemical reactions as possible in the least amount of time. It is also desirable to reduce costs and increase control and efficiency of the chemical reactions.

For example, a known quantitative PCR method uses a flat stainless steel plate that has two opposite plate surfaces and an array of through-holes extending completely through the plate between the plate surfaces. The through-holes are configured to hold nanoliter-sized reaction volumes of a liquid. The plate is chemically modified so that the plate surfaces are hydrophobic and interior surfaces of the through-holes are hydrophilic. The differential hydrophobic-hydrophilic quality retains liquid within the through-holes during the plate preparation process. Select primer pairs are inserted into through-holes in the plate so that each primer pair has a known through-hole location in the array. The primer pairs are immobilized onto the interior surfaces of the corresponding through-holes. Once the plate is prepared, a cDNA sample is mixed with fluorescent PCR reagents and loaded into the through-holes of the array. The through-holes are then sealed and the plate undergoes a thermal cycle pursuant to known PCR protocols. If a particular primer pair is capable of hybridizing with the cDNA sample, then mRNA having fluorescent properties will be amplified within the through-hole of that particular primer pair. Images of the plate are acquired and subsequently analyzed to determine which primer pairs amplified the mRNA and to what amount.

However, the above method may have certain challenges or limitations. For example, each primer pair must have a known through-hole location in order to identify the primer pairs that positively react with the cDNA sample. In other words, the reaction volumes within the through-holes are not separately identifiable, but must be identified by the through-hole's position in the array. Second, an imager or optical detector cannot detect amplification from a side of the through-hole but must face one of the plate surfaces in order to detect light emitting from the through-holes. As such, in assays that include real-time imaging or in assays that are interested in diffusion properties of the reactants, the image may provide limited information. Furthermore, the plate's size and shape limit or restrict the plate's use in systems where more sortable or transportable substrates are desired.

Another method that seeks to form separate reaction volumes is known as "emulsion PCR." Emulsion PCR may be used to address problems where unwanted DNA fragments are amplified in conventional PCR amplification. In the emulsion PCR method, an oil-surfactant mixture is mixed with an aqueous solution to form tiny aqueous micelles that are separated from each other by the oil-surfactant mixture. The aqueous solution includes DNA fragments as well as other PCR components for amplifying the DNA fragments. A density of the DNA fragments compared to the rest of the aqueous solution is relatively small so that when the aqueous solution is mixed with the oil-surfactant mixture to make the aqueous micelles, there are at most a few DNA fragments in each aqueous micelle. The emulsion is then subjected to known PCR protocols to amplify the DNA fragment(s) in each aqueous micelle. Each aqueous micelle that contains at least one DNA fragment effectively functions as a bioreactor where the DNA fragment is amplified. With very few DNA fragments in the aqueous micelles, unwanted DNA fragments are not amplified.

One known pyrosequencing method uses emulsion PCR to sequence, for example, genomic DNA on a large number of capture beads. Each capture bead includes one sstDNA fragment (single-stranded DNA fragment) that is immobilized on the capture bead. The capture beads are added to a water-in-oil mixture similar to the emulsion described above. When the aqueous micelles are formed, each capture bead may be within one corresponding aqueous micelle. The aqueous micelles may then experience PCR thermal cycles to generate clonally amplified DNA fragments on the capture beads. After amplification, the capture beads are then added to corresponding wells in a microplate where each capture bead undergoes a sequencing-by-synthesis technique known as pyrosequencing. More specifically, nucleotides are sequentially delivered to the wells by flowing a solution containing a specific nucleotide through the microplate. When a nucleotide contacts a particular capture bead having template DNA strand with an appropriately complementary position, the nucleotide is added to a growing DNA strand that is hybridized to the template on the capture bead. Addition of a nucleotide that is complementary to the template DNA generates a fluorescent light signal that is captured by a CCD camera. The images are subsequently analyzed to determine the sequence of the genome.

However, emulsion PCR has limited applications. First, the aqueous micelles are difficult to individually identify and manipulate. Rather, information about the amplified nucleic acids within the aqueous micelles is typically determined through subsequent analysis and after the destruction of the aqueous micelles. Second, the aqueous micelles have limited sizes and shapes and have a limited stability since the surface tension properties are determined by the composition of the aqueous solution. As such, use of the emulsion PCR method is generally limited to situations when the composition of the aqueous solution forms stable aqueous micelles in the oil-surfactant mixture. Accordingly, emulsion PCR may not be suitable for assays that desire bioreactors having certain sizes or shapes. Third, after the aqueous micelles are formed in emulsion PCR, it may be difficult to manipulate or handle the aqueous micelles in a controlled manner. For example, it may be difficult to add reagents or other chemicals incrementally to the aqueous micelles. Furthermore, it may be difficult to add reagents or other chemicals selectively to certain aqueous micelles and not others.

Accordingly, there is a need for individually identifiable microvessels that separate reaction volumes from each other and/or an ambient environment. There is also a need for bioreactors that may be at least one of transported, sorted, and manipulated during a biological or chemical assay without destroying the reaction volume or somehow negatively affecting the chemical reaction therein. There is also a need for microvessels that may hold substances within reservoir cores where the substances and/or chemical reactions involving the substances may be detected externally. There is also a need for microvessels that store, transport, and release chemical substances in ways that they can be kept separated or combined for various steps of a synthetic or analytic process.

BRIEF DESCRIPTION OF THE INVENTION

In accordance with one embodiment, an encoded microvessel is provided that includes a microbody and a reservoir core that extends into the microbody. The microbody can be configured to separate a substance, such as a biological or chemical substance, in the reservoir core from an ambient environment that surrounds the microbody. The microbody can include a material that at least partially surrounds the reservoir core and facilitates detection of a characteristic of the substance within the reservoir core. Optionally, the material can be transparent so as to facilitate detection of an optical characteristic of a substance within the reservoir core. The microbody can have an identifiable code that is associated with the substance.

In another embodiment, a method of manufacturing a plurality of microvessels that are configured to separate one or more substances from an ambient environment is provided. The method can include providing an optical substrate having a core region and a coding region that surrounds the core region and writing at least one identifiable code in the coding region of the substrate. The method can also include removing the core region of the substrate and fragmenting the optical substrate to form a plurality of microvessels. Each of the microvessels can include a microbody and a reservoir core within the microbody. The reservoir core can be configured to hold a corresponding substance.

In yet another embodiment, a method of reading a plurality of encoded microvessels used in an assay for biological or chemical analysis is provided. The method can include providing a plurality of encoded microvessels. The microvessels can include a respective microbody and a reservoir core configured to hold a substance in the reservoir core. The microbody can include a material that surrounds the reservoir core and facilitates detection of a characteristic of the substance within the reservoir core. Optionally, the material can be transparent so as to facilitate detection of an optical characteristic of a substance within the reservoir core. The microbody can include an identifiable code associated with the substance. The method can also include determining the corresponding codes of the microvessels.

In a further embodiment, a method of conducting an assay for biological or chemical analysis is provided. The method can include providing a plurality of encoded microvessels. Each microvessel can include a microbody and a reservoir core that holds a substance within the reservoir core. The microbody can include a material that surrounds the reservoir core and facilitates detecting a characteristic of the substance within the reservoir core. Optionally, the material can be transparent so as to facilitate detection of an optical characteristic of a substance within the reservoir core. The microbodies of the plurality of microvessels can have identifiable codes associated with the corresponding substances. The method can also include exposing the microvessels to conditions for conducting desired reactions within the respective reservoir cores and determining a detectable characteristic of the substances within the corresponding reservoir cores. The method can also include determining the codes of the microvessels.

In another embodiment, an isolated microvessel is provided that includes an encoded microvessel having a microbody and a reservoir core. The microbody can be configured to separate a biological or chemical substance in the reservoir core from an ambient environment surrounding the microbody. The microbody can include a material that at least partially surrounds the reservoir core and facilitates detection of a characteristic of the substance within the reservoir core. Optionally, the material can be transparent so as to facilitate detection of an optical characteristic of a substance within the reservoir core. The microbody can include an identifiable code associated with the substance. The isolated microvessel can also include a compartment that is configured to separate the microvessel from an ambient environment surrounding the compartment.

In a further embodiment, a plurality of isolated microvessels is provided that includes a plurality of encoded microvessels. Each encoded microvessel can include a microbody and a reservoir core. The microbody can be configured to separate a biological or chemical substance in the reservoir core from an ambient environment surrounding the microbody. The microbody can include a material that at least partially surrounds the reservoir core and facilitates detection of a characteristic of the substance within the reservoir core. Optionally, the material can be transparent so as to facilitate detection of an optical characteristic of a substance within the reservoir core. The microbody of each microvessel can include an identifiable code that distinguishes individual microvessels of the plurality of encoded microvessels from each other. The plurality of isolated microvessels can also include a plurality of compartments. Each compartment can be configured to separate individual microvessels of the plurality of encoded microvessels from each other.

In another embodiment, a method of producing an array having biomolecules at known locations is provided. The method includes providing a holder that has an active side including a plurality of recesses thereon. The recesses have respective recess locations. The method also includes providing a plurality of microparticles to the holder. The microparticles have identifiable codes and hold biomolecules that are associated with the corresponding identifiable codes. The microparticles are randomly located within corresponding recesses. The method also includes determining the identifiable codes of the microparticles within the corresponding recesses and designating the recesses as reaction sites that include the biomolecules of the corresponding microparticles in the recess.

In another embodiment, a method of conducting an immunoassay is provided. The method includes providing a plurality of encoded microvessels. Each microvessel includes a microbody and a reservoir core that holds a solid-phase material in the reservoir core. The microvessels have identifiable codes, and the solid-phase material in the microbodies have corresponding allergens immobilized thereon that are associated with the corresponding identifiable code. The method includes exposing the microvessels to a sample having antibodies. The antibodies selectively binding to the allergens of the microvessels. The method also includes identifying the microvessels that exhibit binding events between the antibodies and the corresponding allergens and determining the identifiable codes of the microvessels to determine the allergens that are associated with the binding events.

BRIEF DESCRIPTION OF THE DRAWINGS

FIG. 23 is a block diagram illustrating a method of selectively modifying interior and exterior surfaces of a plurality of microvessels in accordance with one embodiment.

FIG. 25 is a block diagram illustrating a method of performing an assay in accordance with one embodiment.

FIG. 34 illustrates a perspective view of a microvessel formed in accordance with an alternative embodiment.

FIG. 35 illustrates a plan view of a microvessel formed in accordance with another embodiment.

FIG. 36 illustrates cross-sectional views of various microvessels formed in accordance with other embodiments.

DETAILED DESCRIPTION OF THE INVENTION

Figure 1:
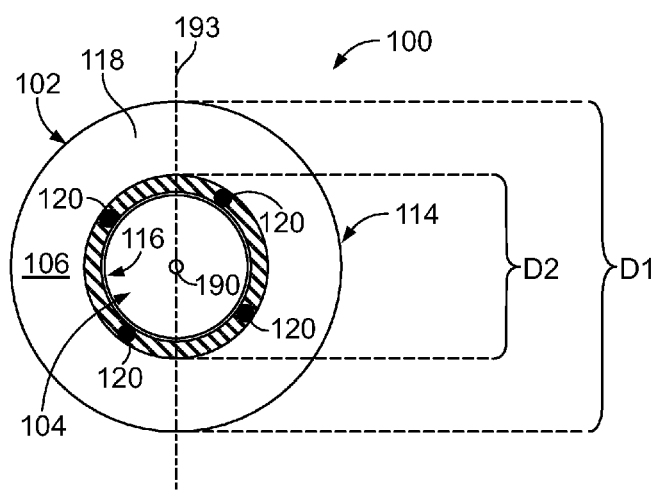
FIG. 1 is an end view of a microvessel formed in accordance with an embodiment.
Figure 2:
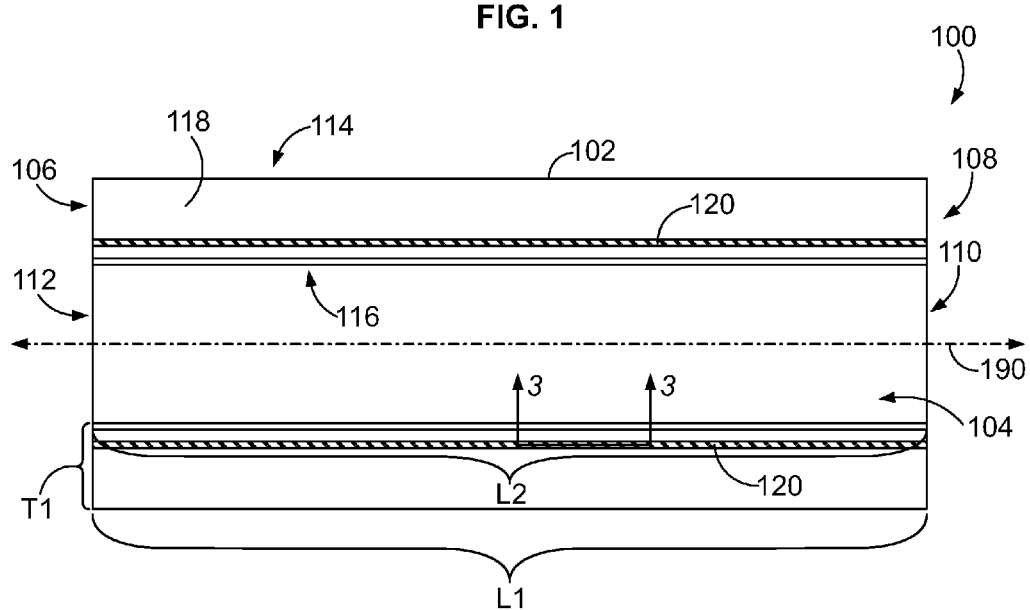
FIG. 2 is a side cross-sectional view of the microvessel shown in FIG. 1.

FIGS. 1 and 2 illustrate an exemplary microvessel 100 that may be formed in accordance with one embodiment. The microvessel 100 may include a microbody 102 having a reservoir core or cavity 104 where a substance, such as a biological or chemical substance (not shown), may be located. Embodiments described herein include microvessels that are configured to isolate or separate a substance from an ambient environment and/or other microvessels. In some embodiments, the microvessels may function as reactors that isolate or separate biological, chemical, or other substances within the reservoir cores from the ambient environment and compartmentalize reactions, such as chemical or biological reactions, therein. For example, microvessels may be used to amplify or sequence nucleic acids within the reservoir core. Accordingly, the microvessels may be referred to as microreactors (or bioreactors or chemical reactors). In particular embodiments, microvessels described herein may also be referred to as capillary beads or capillary particles.

In particular embodiments, individual microvessels are encoded with one or more identifiable codes. The identifiable code may be associated with a substance that the corresponding microvessel contains (i.e., the substance can be determined based upon the corresponding identifiable code) and/or the identifiable code may provide information regarding the microvessel (e.g., date of production, manufacturing plant, type of material, source of substances in the reservoir core). For example, a database may include a list of identifiable codes that are correlated to the substances within the microvessels or information about the microvessels. The identifiable code may also provide other information. The identifiable code may comprise any detectable property(ies) or feature(s) that can be associated with the microvessel. The code may distinguish one microvessel over other similar microvessels. Examples of identifiable codes are described in greater detail below. Each microvessel may be detected, scanned, or imaged (individually or with other microvessels) to determine the identifiable code and to determine any detectable characteristics indicative of a substance or reaction.

In other embodiments, a microvessel may function as a micropackage that is configured to hold a substance within the reservoir core until a desired time has elapsed or until a desired occurrence. At such time or occurrence, the substance can be released or allowed to interact with the ambient environment, or another substance can be introduced into the reservoir core. For example, the microvessels may include reagents or enzymes held within the reservoir core. When the microvessel is added to a chamber (or compartment) that includes, for example, an aqueous solution, the reagents or enzymes may diffuse out of the reservoir core and into the chamber. Accordingly, the microvessels may also be referred to as micropackages or microcapsules. In some embodiments, such microvessels may be encoded to identify the substance that was delivered to the chamber.

In alternative embodiments, microparticles that do not include a reservoir core may be used in a similar manner for transporting biomolecules. For example, embodiments described herein include methods for providing an array of reaction sites. The method may include delivering biomolecules to random recesses in a microplate using microparticles that may or may not have a reservoir core.

In particular embodiments, a microvessel can function as a reference standard or calibration standard. For example, the reservoir core can hold a detectable substance in an amount that is known or otherwise reliable for producing predictable characteristics. Any of a variety of characteristics can be used for calibration or reference including, for example, electromagnetic characteristics such as signal intensity, absorbance wavelength, excitation wavelength, emission wavelength, polarization state, excited state lifetime or a combination thereof. Other useful characteristics that can be alternatively or additionally used include, but are not limited to, electrical properties, weight, mass, magnetic properties, chemical properties or a combination thereof. Microvessels that are used as calibration standards may or may not be encoded with an identifiable code.

One or more microvessels having a detectable substance, for example in different amounts or concentrations, can be used for calibration or reference in an instrument or process that utilizes detection of the substance. For example, a set of microvessels that produce different signal intensities can be used to calibrate the gain for an instrument that detects the signal. In particular embodiments, the microvessels can hold known amounts of fluorophore that emit fluorescence at different intensities in a defined wavelength range and the microvessels can be used to adjust the gain for a fluorescence detector. In embodiments wherein a plurality of microvessels is used to calibrate an instrument or process, the microvessels can further be encoded with an identifiable code that indicates one or more characteristic of the microvessel that is relied upon for calibration, such as the amount of a substance held in the reservoir core of each microvessel, the chemical identity of a substance held in the reservoir core of each microvessel, source of a substance held in the reservoir core of each microvessel, date of manufacture of a substance held in the reservoir core of each microvessel, date of manufacture of each microvessel, history of use for each microvessel, or the like.

As used herein the term "microbody" is intended to mean an individual mass of solid material. A microbody can have a spatial size with a total volume that is at least one cubic nanometer, at least 10 cubic nanometers, at least 100 cubic nanometers, at least 1 cubic millimeter, at least one cubic centimeter, at least 10 cubic centimeters, at least 100 cubic centimeters or more. Additionally or alternatively, a microbody can have a spatial size with a total volume that is at most 100 cubic centimeters, at most 10 cubic centimeters, at most 1 cubic centimeter, at most 1 cubic millimeter, at most 100 cubic nanometers, at most 10 cubic nanometers, at most 1 cubic nanometer or less.

As used herein the term "reservoir core" is intended to mean a region in a microbody or other solid material that is separated from the ambient environment of the microbody. In some embodiments, the region is at least substantially defined by interior surfaces of the microbody. The region may occupy or pass through the geometric center of a microbody. However, the region need not pass through the geometric center of a microbody and can avoid the geometric center altogether in other embodiments. In particular embodiments, the region can be entirely surrounded by the microbody. Alternatively, the microbody can have one or more openings between the region and the ambient environment. For example, the microbody can have no more than a single opening between the region and the ambient environment, the microbody can have no more than two openings between the region and the ambient environment or the microbody can have a plurality of openings (two or more) between the region and the ambient environment. In some embodiments the reservoir core can have the shape of a tube, capillary, a single channel, network of channels, well, cup, divot, pit, or the like.

In addition to a microbody and a reservoir core, a microvessel may have other component(s), feature(s), and/or substance(s). The microvessels may have solids or semi-solids inserted, fully or partially, into the reservoir cores. For example, the reservoir core may be filled with a porous gel or substance that is configured to control diffusion or filter fluidic substances that may flow into the reservoir core. Similarly, a solid or semi solid can cover or coat the opening of a reservoir core in a microvessel to control or block the flow of a substance into or out of the reservoir core. The microbody may also hold one or more items, such as DNA capture beads or controlled pore glass (CPG) beads. In addition, the microbodies may hold a solid phase cellulose material that may be used to measure allergen-specific IgE antibodies similar to ImmunoCAP® test developed by Pharmacia Diagnostics. As such, the microvessel may also be referred to as a composition or a microdevice.

Furthermore, in some embodiments, the microbody may have multiple reservoir cores where the reservoir cores include a common substance or different substances. The reservoir cores may be separate from one another such that the reservoir cores are not in fluid communication with each other through the microbody. Alternatively, the reservoir cores may be in fluid communication with one another through micro-channels that extend between and join the reservoir cores.

In some embodiments described herein, one or more microvessels may be used with various systems or apparatuses and in conjunction with various methods. For example, the microvessels may be added to a water-in-oil mixture similar to those described in U.S. Pat. No. 7,323,305 and U.S. Pat. No. 6,489,103, each of which is incorporated herein by reference in its entirety. When aqueous micelles are formed within the mixture, one or more microvessels may be within an aqueous micelle. In particular embodiments, the micelles in a population will contain, on average, no more than one microvessel. Furthermore, in some embodiments, one or more microvessels may be isolated from other microvessels within a chamber or a well. The microvessels may be used to perform reactions within the chamber or well. Accordingly, embodiments described herein include isolated microvessels or apparatuses having isolated microvessels.

As used herein, "reaction" includes a chemical transformation, chemical change, or chemical interaction. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. Exemplary reactions also include allergens-of-interest reacting with antibodies. Either the allergens or the antibodies can be disposed within the reservoir cores of microparticles. Furthermore, the antibodies can be IgE antibodies of a patient's sample.

Any of a variety of substances can be used in a method or composition described herein. As used herein, "biomolecules" includes at least one of nucleosides, nucleic acids, polynucleotides, oligonucleotides, proteins, enzymes, polypeptides, antibodies, antigens (such as allergens), ligands, receptors, polysaccharide, carbohydrate, polyphosphates cells, tissues, organisms, and any other biologically active chemical compound(s) such as analogs or mimetics of the aforementioned species. As used herein, a "biological or chemical substance" includes biomolecules and samples, as well as other chemical compound(s). For example, a biological or chemical substance may include a substance configured to modify the surface properties of a reservoir core such as a polymeric molecule. A biological or chemical substance may also be used to detect, identify, or analyze other chemical compound(s), or function as intermediaries to study or analyze other chemical compound(s). By way of example, the biological or chemical substance may be components used in amplification protocols, such as buffer solution, primers, reagents, and dyes. In a further example, the biological or chemical substance can be an enzyme or reagent used in a coupled reaction to detect the product of another reaction such as an enzyme or reagent used to detect pyrophosphate in a pyrosequencing reaction. Enzymes and reagents useful for pyrophosphate detection are described, for example, in U.S. Patent Publication No. 2003/0208867, which is incorporated by reference herein in its entirety. Biomolecules, samples, and biological or chemical substances may be naturally occurring or synthetic and may be suspended in a solution or mixture within a microvessel or may be immobilized on a surface of the microvessel. Biomolecules, samples, and biological or chemical substances may also include a pharmaceutical composition. Biomolecules, samples, and biological or chemical substances of interest may also be referred to as targets, probes, or analytes.

As used herein, the term "modified," when used with respect to a surface, includes the surface being chemically changed and/or physically changed. In physical modification, a surface may be roughened, pitted, patterned, shaped, or smoothed to facilitate holding a substance. For example, a surface may be physically modified to facilitate immobilizing desired biomolecules thereon or to facilitate deterring immobilization of unwanted biomolecules. The surface may also be roughened, smoothed, pitted, patterned, or shaped to produce desired effects on light transmission through the microbodies of the microvessels. Exterior and/or interior surfaces may be shaped to increase radiation of light energy onto predetermined portions of the reservoir core. For example, an interior surface may have induced modulations in the index of refraction of the material, ridges or grooves (e.g., gratings) formed thereon to increase an intensity of radiation on biomolecules attached to the interior surface. The exterior and/or interior surfaces of the microvessels may also be modified to facilitate detection of reactions occurring within the reservoir cores. For example, the exterior and/or interior surfaces may be shaped to filter light emitting from the reactions.

Chemical modification of a surface may result in physical changes to the exterior and/or interior surfaces (e.g., through etching). Chemical modification may also facilitate a desired interaction with a substance that interfaces directly or indirectly with the surface. For example, the interior surfaces may be modified to increase wettability (i.e., the interior surface may be made hydrophilic). In such embodiments, the interior surfaces may be configured to draw a polar liquid into the reservoir core (e.g., through capillary action). As another example, the exterior surfaces of the microvessels may be modified to be hydrophilic so that when, for example, the microvessels are mixed in a water-in-oil emulsion at least one microvessel is isolated within an aqueous micelle. A microvessel can be applied to an emulsion partitioning technique in a method similar to the method of isolating DNA capture beads within aqueous micelles used in pyrosequencing as set forth elsewhere herein.

A surface of a microvessel, whether in a reservoir core or on an exterior microbody surface can have a moiety that acts as a chemical linker or precursor to a chemical linker. Any of a variety of linker moieties and precursor moieties known in the art can be used, examples of which include, but are not limited to, those described in U.S. Patent Publication No. 2006/0057729 A1, and U.S. Pat. No. 7,504,499, each of which is incorporated herein by reference in its entirety. A surface of a microvessel can be chemically modified to incorporate a linker precursor or linker moiety using methods known to those skilled in the art or readily ascertainable based on the properties of the surface, linkage chemistry, and substance to be linked to the surface.

Chemical modification may also include selectively immobilizing desired biomolecules to at least one of the interior and exterior surfaces. As used herein, the term "immobilized," when used with respect to a biomolecule, includes substantially attaching the biomolecule at a molecular level to a surface. For example, biomolecules may be immobilized to a surface of the microbody using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules to a surface of a microbody may be based upon the properties of the microbody surface, the liquid medium carrying the biomolecules, and the properties of the biomolecules themselves. In some cases, a surface may be first modified to have functional groups bound to the surface. The functional groups may then bind to biomolecules to immobilize the biomolecules to the surface.

Nucleic acids can be immobilized to a surface of a microvessel and replicated on the surface using a solid phase amplification technique. For example, a nucleic acid can be attached to a surface and amplified using bridge amplification. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, using methods set forth in further detail below.

In some embodiments, items or solid substances (including semi-solid substances) may be disposed within the reservoir core. When disposed, the item or solid may be physically held within the reservoir core through an interference fit, adhesion, or entrapment. Exemplary items or solids that may be disposed within the reservoir cores include polymer beads, pellets, agarose gel, powders, quantum dots, or other solids that may be compressed and/or held within the reservoir core. As another example, a solid phase cellulose (e.g., 3D cellulose polymer) having an allergen-of-interest or antibody attached thereto may be disposed within the reservoir core. In particular embodiments, a nucleic acid superstructure such as a DNA ball can be disposed in or at a reservoir core, for example, by attachment to a surface of the reservoir core or by residence in a liquid within the reservoir core. A DNA ball or other nucleic acid superstructure can be preformed and then disposed in or at the reservoir core. Alternatively, a DNA ball can be synthesized at the reservoir core. A DNA ball can be synthesized by rolling circle amplification to produce a concatamer of a particular nucleic acid sequence and the concatamer can be treated with conditions that form a relatively compact ball. DNA balls and methods for their synthesis are described, for example in, U.S. Patent Publ. No. 2008/0242560 A1, which is incorporated herein by reference in its entirety.

A substance that is held in a reservoir core of a microvessel can be in a solid, liquid, or gaseous state. A substance can be held in a reservoir core in the same state that it was introduced to the reservoir core. For example, a liquid substance can be loaded into a reservoir core and the substance can remain liquid whether or not it is converted to a different chemical species. Alternatively, a substance can be introduced to a reservoir core in a first state and then converted to another state. For example, a substance can be introduced to a reservoir core in a liquid state and the microvessel can be subsequently subjected to lyophilization or freeze drying to convert the substance in the reservoir core of the microvessel to a solid state.

As used herein, an "ambient environment" may be liquid, gas, or solid or a combination thereof. As used herein, when the term "to separate" is used with respect to an ambient environment and a substance within a reservoir core, the substance may be separate from the ambient environment without being completely isolated from the ambient environment. Rather, a substance may be separate from an ambient environment when the substance is retained within the reservoir core for a desired period of time. As one example, a microvessel may separate a hydrophilic solution within the reservoir core from an ambient environment that includes a non-polar liquid even though a portion of the hydrophilic solution in the reservoir core interfaces with the non-polar liquid. Accordingly, the substance within the reservoir core and the ambient environment may be predetermined or controlled to prevent or limit interaction between the substance and the ambient environment until a desired event occurs or time elapses.

In alternative embodiments, separation of a substance from an ambient environment can be a fluidic isolation such that the substance in the reservoir core is prevented from making physical contact with a liquid, gas, or solid in the ambient environment. For example, a reservoir core can be capped or sealed to prevent passage of a substance either permanently or temporarily until the cap or seal is removed.

In some embodiments, the substances are not necessarily separated from the ambient environment but from other substances in other reservoir cores. For example, in testing for allergen sensitivity, the allergens-of-interest in each reservoir core are separated from the other allergens-of-interest, but all allergens-of-interest are exposed to the same ambient environment (e.g., patient's sample).

In some embodiments, the ambient environment is controlled to facilitate holding or retaining an item or substance within the reservoir core or to facilitate separating the item or substrate from the ambient environment or other microvessels. More specifically, embodiments described herein may utilize forces experienced by the substance located within the reservoir core. When the substance includes a liquid, such forces may be cohesive forces (i.e., attractive forces between like molecules of the liquid) and adhesive forces (i.e., attractive forces between molecules of the liquid and a solid surface or vapor that surrounds the liquid). Cohesive and adhesive forces arise from the interaction of atoms and molecules that are located along, for example, a liquid-vapor interface and a liquid-solid interface. These forces may also be characterized as capillary forces when the liquid is a polar liquid.

A liquid may have different wetting abilities to a solid surface depending upon the nature of the liquid and the solid surface. Wetting is a liquid's ability to spread along a solid surface. The wetting of a solid surface by a liquid is controlled by the intermolecular interactions of molecules along an interface between the two phases. If the adhesive forces are relatively greater than the cohesive forces, the wetting of the liquid to the surface is greater. If the cohesive forces are relatively greater than the adhesive forces, the wetting of the liquid to the surface is smaller. Embodiments may utilize the wetting abilities of a microvessel or container during the course of an assay or other usage.

In embodiments utilizing aqueous or polar liquids, the interaction between the liquid and the solid surface can be characterized as hydrophobic or hydrophilic. As used herein, a solid surface is hydrophobic if it repels an aqueous or polar liquid. For example, a contact angle between the aqueous or polar liquid and the hydrophobic surface of the solid is typically greater than 90 degrees. A surface is hydrophilic if it is attracted to an aqueous or polar liquid. For example, a contact angle between the aqueous or polar liquid and the hydrophilic surface of the solid will typically be less than 90 degrees.

In other embodiments, a non-polar liquid, such as alkanes, oils, and fats, may be used as the liquid within the reservoir core and/or as part of the ambient environment. Non-polar liquids may be attracted to a surface that has a hydrophobic interaction with aqueous or polar liquids. Likewise, non-polar liquids are not attracted to a surface that has a hydrophilic interaction with aqueous or polar liquids. As such, hydrophobic and hydrophilic surfaces may be used with embodiments described herein to retain or control the flow of liquids within the reservoir core or to control the microvessels as the microvessels are manipulated, sorted, or transported.

Other factors may affect the contact angle or the wetting of a liquid to a solid. For example, a purity of the liquid or whether a surfactant is used may affect the surface tension of the liquid and the molecular interactions along the solid-liquid interface. A purity of the solid or whether a coating is placed on the solid surface may affect the surface energy of a solid. Also, temperature of the environment, a composition of the surrounding air, and the roughness or smoothness of the surface may all affect the interactions between the liquid and the solid surface. As such, embodiments described herein may utilize these other factors for certain purposes.

The fluidic concepts discussed briefly above are discussed in greater detail in *Surfaces, Interfaces, and Colloids: Principles and Applications, Second Edition*, Drew Meyers, 1999, John Wiley & Sons, Inc. and in *Contact Angle, Wettability, and Adhesion*, edited by Robert F. Gould (1964), each of which are hereby incorporated by reference in its entirety.

Thus, the reservoir core may have microfluidic dimensions in which surface tension and cohesive forces of a liquid in the reservoir core and the adhesive forces between the liquid and interior surfaces that define the reservoir core have a significant effect on the liquid therein. More specifically, the dimensions of the reservoir core (as well as the interior surfaces that define the reservoir core) may be configured to retain a liquid within the reservoir core after the liquid has been deposited therein. The liquid may be retained within the reservoir cores even though the microvessels are transported, sorted, manipulated, or otherwise subject to forces that would normally move liquid that is not held within a reservoir core.

By way of example, the reservoir core may have a diameter that is less than or equal to about 1 mm. More specifically, the diameter may be less than or equal to about 500 µm or, more specifically, less than 100 µm. The diameter may be less than or equal to about 50 µm. In particular embodiments, the diameter may be less than 25 µm, and in even more particular embodiments the diameter may be less than 10 µm. Alternatively or additionally, the diameter may be greater than 10 µm, 25 µm, 50 µm, 100 µm or 500 µm. As used herein, a "diameter" is a distance measured between substantially opposing surfaces. A diameter can be measured as the shortest, longest or average distance between substantially opposing surfaces in a cross-section of the reservoir core. A diameter is not intended to be limited to reservoir cores having circular cross-sections. Rather, the reservoir core may have other geometrically shaped cross-sections, such as an elliptical cross-section; an N-sided cross-section where N is an integer greater than 3 including, for example, a 4-sided rectangular cross-section, a 4-sided square cross-section, or a 6-sided hexagonal cross-section; and the like.

Accordingly, embodiments described herein may be used in various biological or chemical processes and systems for academic or commercial analysis, research, and investigation. Embodiments may also be used in various biological or chemical processes for commercial production of biological or chemical substances, including pharmaceutical compositions. By way of example, microvessels may be used in various methods and processes that include amplifying or sequencing nucleic acids. The microvessels may also be used in various methods and processes to deliver reagents or other chemicals to a chamber or another reaction volume. In addition, the microvessels may be used in various methods and processes where it is desired to observe a detectable property of a reaction within a defined reaction volume. In alternative embodiments, the microvessels may be used to calibrate an imaging system and/or provide a reference standard of a detectable property. In other embodiments, the microvessels may be used to screen or test an individual's sensitivity to allergens-of-interest similar to ImmunoCAP® test developed by Pharmacia Diagnostics. In a similar manner, the microvessels may also be used to detect or test for certain reactants (e.g., pollutants, toxins) in the ambient environment.

Returning to FIGS. 1 and 2, the microbody 102 may be configured to separate an item or a substance (not shown) located in the reservoir core 104 from an ambient environment that surrounds the microbody 102. The substance may be a biological or chemical substance. As shown, the microbody 102 has a length $L_1$ (FIG. 2) that extends along a central longitudinal or core axis 190 between a pair of opposite facing ends 106 and 108 (FIG. 2). The microbody 102 also has a width or diameter $D_1$ (FIG. 1) that may be measured transverse to the core axis 190. Also shown, the reservoir core 104 has a length $L_2$ that may extend along the core axis 190 and a width or diameter $D_2$. The microbody 102 may be elongated such that the length $L_1$ is substantially greater than the diameter $D_1$. The reservoir core 104 may extend lengthwise (i.e., through the larger dimension of the microbody 102).

In the exemplary embodiment, the reservoir core 104 extends entirely through the microbody 102 between a pair of core openings 110 and 112 such that the lengths $L_1$ and $L_2$ are substantially equal. However, in alternative embodiments, the reservoir core 104 may extend only partially into the microbody 102 such that the lengths $L_1$ and $L_2$ are not substantially equal. Also, in alternative embodiments, the reservoir core may extend along the diameter $D_1$ (or a shorter dimension of the microbody 102). The core openings 110 and 112 may provide fluidic access into the reservoir core 104 (i.e., the core openings 110 and 112 lead into the reservoir core 104). In the exemplary embodiment, the reservoir core 104 extends linearly through the microbody 102 in a non-curved manner without turning or changing shape. However, in alternative embodiments, the reservoir core 104 may have different configurations. For example a reservoir core can form a single large chamber or void space. Alternatively, a reservoir core can be porous having a network or collection of interconnected chambers or void spaces.

The microbody 102 has an exterior surface 114 that extends around the core axis 190 and may be in contact with the ambient environment. The microbody 102 may form one or more walls 118 that extend around the reservoir core 104 and between the interior and exterior surfaces 116 and 114. The interior surface 116 defines the reservoir core 104 of the microvessel 100. As shown in FIGS. 1 and 2, the microbody 102 has one continuous tubular or cylindrical wall 118 that extends about the core axis 190 (i.e., curves around the core axis 190). The wall 118 may have a thickness $T_1$ (FIG. 2) measured between the interior and exterior surfaces 116 and 114.

As shown in FIG. 1, the thickness $T_1$ may be substantially uniform about the core axis 190. Furthermore, the reservoir core 104 may be centered about a geometric center of the microvessel 100 (indicated by the core axis 190 in FIG. 1). As such, the microvessel 100 may be substantially symmetric with respect to a plane 193 that divides the microbody 102 and includes the core axis 190. (The plane 193 is indicated by dashed lines that intersect the core axis 190 in FIG. 1.) Furthermore, the microvessel 100 may be rotationally symmetric about the core axis 190. In such embodiments, the wall 118 may have a substantially equal effect on light energy emitted from within the reservoir core 104 and transmitted through the wall 118 regardless of the rotational orientation of the microvessel 100 about the core axis 190.

The exterior and interior surfaces 114 and 116 may be modified to have predetermined surface properties. For example, the interior surface 116 may be configured to interact with or affect the reactions that occur within the reservoir core 104. Alternatively, the interior surface 116 may be substantially inert with respect to the substance held therein so that the interior surface 116 does not interfere with the desired reaction. In some embodiments, the interior surface 116 is modified to retain the substance within the reservoir core 104. For example, the interior surface 116 may be at least partially hydrophilic to facilitate retaining a polar liquid within the reservoir core 104. The interior surface 116 may also be at least partially hydrophobic to facilitate retaining a non-polar liquid therein. Furthermore, the interior surface 116 may have portion(s) that are hydrophilic and portion(s) that are hydrophobic. For example, a polar liquid may be held within one region of the reservoir core 104 and a non-polar liquid may be held in a different region of the reservoir core 104.

A cross-section of the reservoir core 104 taken transverse to the core axis 190 may be substantially uniform between the core openings 110 and 112. Dimensions of the reservoir core 104 and the surface properties of the interior surface 116 may be configured to control a flow of fluid through the reservoir core 104. For example, as a contact angle of a liquid with respect to the interior surface 116 of the reservoir core 104 increases, cross-sectional dimensions of the reservoir core 104 may be increased to enable fluid to flow into and through the reservoir core 104. Likewise, as the contact angle of the liquid with respect to the interior surface 116 decreases, the cross-sectional dimensions of the reservoir core 104 may be decreased. As such, the flow of the fluid through the reservoir core 104 may be controlled by the surface properties and the cross-sectional dimensions of the reservoir core 104. Controlling the flow of the fluid includes increasing or decreasing a rate of wetting by the fluid. Furthermore, controlling the flow of the fluid also includes preventing the fluid from entering the reservoir core 104.

Modification of the interior and exterior surfaces 116 and 114 may include immobilizing substances along the surfaces. For example, coatings and resins may be deposited onto the interior and exterior surfaces 116 and 114. Chemical modifications can also be used as described previously herein. In particular embodiments, substances immobilized onto the interior surface 116 and/or the exterior surfaces 114 do not negatively affect transmission of light such that optically detectable characteristics within the reservoir cores 104 are rendered undetectable or substantially undetectable.

The microbody 102 may be formed from a material that provides structural integrity to the microvessel 100 so that the microvessels 100 may be used for a certain purpose. The material of the microbody 102 may be at least partially buoyant so that the microvessel 100 may be mixed and transported with other similar microvessels in a fluidic medium. In some embodiments, the microvessels 100 may be transported by flowing through a microfluidic circuit, mixed together in a fluidic medium, and arranged on an examination surface for imaging. Exemplary microfluidic circuits, flow systems, and methods for providing or arranging microbeads on an examination surface are described in U.S. Patent Application Publ. No. 2006/0063271, which is incorporated by reference in its entirety, and which may also be used with the microvessels described herein. The microvessels 100 may also be exposed to thermal cycling and harsh chemicals. Furthermore, the material may be at least partially transparent to allow an optically detectable property of a reaction within the reservoir core 104 to be detected through the transparent material of the microbody 102. The material may also be configured to efficiently conduct heat or, alternatively, may be substantially insulative. Examples of material that may be used to form the microbody 102 include at least one of silica glass ($SiO_2$), phosphate glass, borosilicate glass, plastic, co-doped materials (i.e. having more than one dopant such as boron-oxide and germanioum-oxide); doped glasses (e.g. $SiO_2$ doped with quantum dots, fluorescent dyes, rare earth atoms, and other atoms), and rubber. Other useful materials include polymethyl methacrylate (PMMA), cyclo-olefin-copolymer (COC), polycarbonate, polystyrene, polypropylene, and poly (tetrafluoroethylene) (PTFE). Also useful are thermally processable polymers capable of forming holographic images via density gradients. Metal or semiconductor materials are also useful.

Various embodiments of the invention are exemplified herein with regard to optical detection methods. It will be understood that other detection methods can be employed such as chemical detection, electromagnetic detection, texture-based or force-based detection such as atomic force detection, acoustic detection, mass detection, thermal detection, magnetic detection among others. For example, thermal detection can be used in which case a microbody may be formed from a material that provides a temperature transducer. The material can include a pressure transducer, for example, in embodiments that utilize pressure detection of a chemical reaction induces outgassing. Non-magnetic material can be used for embodiments employing magnetic detection.

In the exemplary embodiment, the microbody 102 has an elongated shape having a circular cross-section that is taken perpendicular to the core axis 190. However, in other embodiments, the cross-section may have different shapes. For example, a shape of the cross-section may be square, rectangular, elliptical, clam-shell, D-shaped, and the like. Furthermore, the side cross-sectional view of the microbody 102 (as shown in FIG. 2) may have other cross-sectional shapes other than a rectangle. For example, the side cross-sectional shape of the microbody 102 may be circular, square, elliptical, clam-shell, D-shaped, and the like. In addition, the microbody may have a three-dimensional shape or geometry other than a cylinder. For example, the microbody 102 may be shaped as a sphere, a cube, a pyramid, a bar, a parallelepiped, a slab, a plate, a brick, a disc shape, and the like. In other embodiments, different regions or portions of the microbody 102 may have different shapes. For example, a first portion may be substantially cylindrical and a second portion may be substantially rectangular.

The size and shape of microbody 102 and the reservoir core 104 may be configured for a certain purpose. In several embodiments, the microbody 102 is sized for highly parallel multiplex assays. For example, the lengths $L_1$ and/or $L_2$ may be less than or equal to about 10 mm (1 cm). More specifically, the lengths $L_1$ and/or $L_2$ may be less than or equal to about 1 mm, less than or equal to about 500 µm, or less than and equal to about 100 µm. Furthermore, in particular embodiments, the lengths $L_1$ and/or $L_2$ may be less than or equal to about 50 µm and, more particularly, the lengths $L_1$ and/or $L_2$ may be less than or equal to about 25 µm. In the exemplary embodiment, the lengths $L_1$ and/or $L_2$ are larger than the diameter $D_1$. However, in other embodiments, the diameter $D_1$ may be greater than or equal to the lengths $L_1$ and/or $L_2$.

Dimensions of a spatial size of the microbody 102 may be characterized as micro-sized or nano-sized. In addition to the dimensions described above, the microbody 102 may have a spatial size with a total volume that is less than or equal to about 50 microliters. In other embodiments, the microbody 102 may have a spatial size with a total volume that is less than or equal to about 10 microliters. Still, in other embodiments, the microbody 102 may have a spatial size with a total volume that is less than or equal to about 1.0 microliter or even less than or equal to about 0.1 microliters. In more particular embodiments, the microbody 102 may have a spatial size with a total volume that is less than or equal to 500 pL. In even more particular embodiments, the microbody 102 may have a spatial size with a total volume that is less than or equal to about 250 pL. More specifically, the microbody 102 may have a spatial size with a total volume that is less than or equal to about 100 pL.

Dimensions of the reservoir core 104 may at least partially define a reaction volume of the microvessel 100 where biological or chemical substances may undergo a reaction. The biological or chemical substance within the reservoir core 104 may provide an optically detectable property or characteristic that indicates an occurrence of a reaction. The reservoir core 104 may have a volume that is less than or equal to about 10 microliters. In other embodiments, the volume of the reservoir core may be less than or equal to about 1 microliter. Still, in other embodiments, the volume of the reservoir core 104 may be less than or equal to about 0.1 microliters or even less than or equal to about 1000 picoliters (pL). In more particular embodiments, the volume reservoir core may be less than or equal to 500 pL. In even more particular embodiments, the volume of the reservoir core 104 may be less than or equal to about 100 pL. More specifically, the volume of the reservoir core 104 may be less than or equal to about 25 pL.

Optionally, the microvessel 100 may be an encoded microvessel having an identifiable code 120. Various coding systems may be used with the microvessels and microparticles described herein including, but not limited to, codes that reflect/refract or filter incident light into a predetermined output pattern; spectral codes that use one or more fluorescent dyes distinguished by their intensities or spatial positions; fluorescently labeled DNA or RNA strands; and codes that are patterned along or through surfaces of the microvessels or microparticles.

Figure 3:
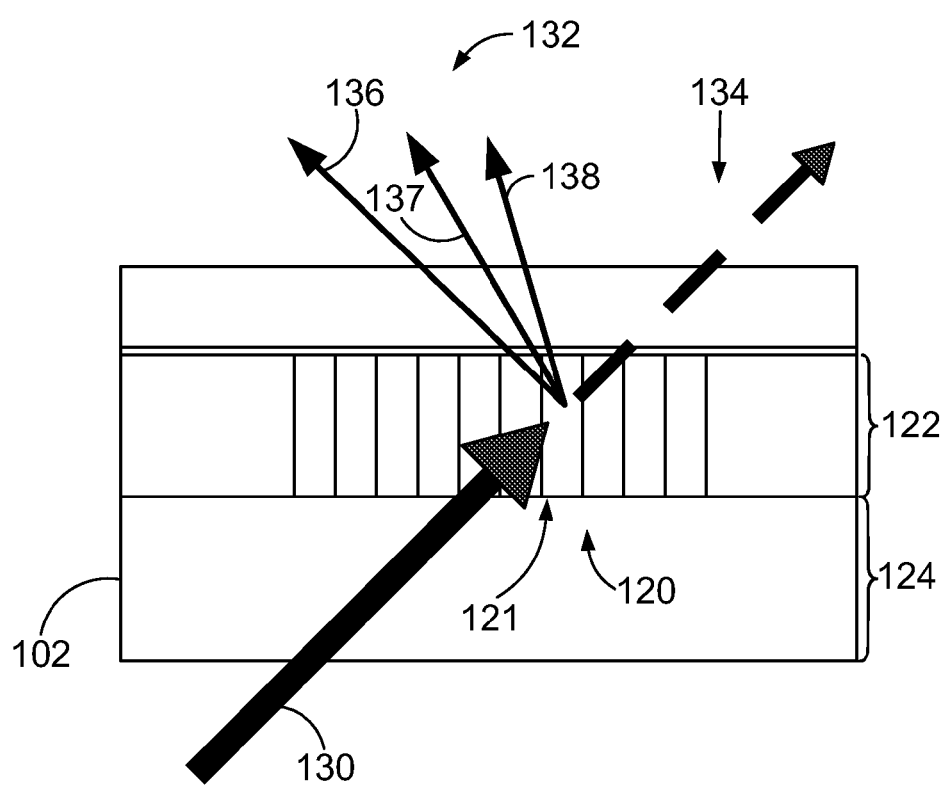
FIG. 3 is an enlarged portion of the microvessel taken along the line 3-3 in FIG. 2.

The identifiable code 120 may be written, impressed, embedded, imprinted, etched, grown, deposited, or otherwise formed within the volume of the microbody 102 and/or along the exterior and interior surfaces 114 and 116. As shown in FIG. 3, the microbody 102 may have an inner coding region 122 and an outer region 124 that surrounds the coding region 122 about the core axis 190. The coding and outer regions 122 and 124 may extend parallel to each other in a direction along the core axis 190. In some embodiments, a material of the coding region 122 may be configured to allow the identifiable code 120 to be the formed within the coding region 122. For example, the coding region 122 may be photosensitive to allow the writing or impressing of the identifiable code 120. Furthermore, the coding region 122 may include a material that allows the identifiable code 120 to be etched, embedded, grown, deposited, or otherwise formed along or within the coding region 122.

In some embodiments, the optical characteristics of any substances or reactions occurring in the reservoir core 104 may be detected through the coding region 122. More specifically, light emitted in the reservoir core 104 may transmit through the coding region 122 and the exterior surface 114 where the emitted light may be detected by an appropriate detection system. Furthermore, the emitted light may transmit through the identifiable code 120 within the coding region 122 to be detected by the detection system.

The identifiable code 120 may be disposed within a volume of the microbody 102 (i.e., between and not including the exterior and interior surfaces 114 and 116). Alternatively, the identifiable code 120 may extend along and include at least one of the exterior and interior surfaces 114 and 116. For example, the identifiable code 120 may be a bar code. Furthermore, the identifiable code 120 may be morphological markings along the exterior surface 114, such as ridges or grooves. The identifiable code 120 may also include a grating formed along the exterior surface 114. For example, the grating can be provided by a modulation in a physical property, such as the density, of the material forming a microbody.

In the exemplary embodiment, the identifiable code 120 is formed from at least one of a variation in refractive index and effective optical absorption of the microbody 102. The variation in refractive index and/or effective optical absorption may provide a predetermined optical output pattern or signal when illuminated with an incident light. For example, the variation may reflect or refract the incident light in a predetermined manner to provide the output pattern. The variation in refractive index and/or effective optical absorption may also passively affect (e.g., through filtering) the incident light to provide the output pattern. The output pattern may be indicative of the identifiable code 120 and may uniquely identify the microvessel 100 and/or the substance within the microvessel 100. The identifiable codes 120 may be gratings and, more particularly, diffraction gratings. In particular embodiments, the identifiable codes 120 are Bragg gratings. The identifiable codes 120 may comprise gratings with a superposition of different predetermined regular periodic variations of an index of refraction disposed in the particle substrate along an axis. Such identifiable codes and others are described in U.S. patent application Ser. No. 10/661,234 (filed Sep. 12, 2003); Ser. No. 10/645,686 (Aug. 20, 2003); Ser. No. 10/645,689 (Aug. 20, 2003); Ser. No. 10/661,031 (Sep. 12, 2003); Ser. No. 10/661,082 (Sep. 12, 2003); Ser. No. 10/661,115 (Sep. 12, 2003); Ser. No. 10/661,116 (Sep. 12, 2003); Ser. No. 10/661,234 (Sep. 12, 2003); Ser. No. 10/661,254 (Sep. 12, 2003); Ser. No. 10/661,836 (Sep. 12, 2003); Ser. No. 10/763,995 (Jan. 22, 2004); Ser. No. 10/956,791 (Oct. 1, 2004); Ser. No. 10/990,057 (Nov. 15, 2004); Ser. No. 11/063,660 (Feb. 22, 2005); Ser. No. 11/063,665 (Feb. 22, 2005); Ser. No. 11/063,666 (Feb. 22, 2005); Ser. No. 11/158,782 (Jun. 21, 2005); Ser. No. 11/187,262 (Jul. 21, 2005); Ser. No. 11/206,987 (Aug. 18, 2005); Ser. No. 11/226,892 (Sep. 13, 2005); Ser. No. 11/226,914 (Sep. 13, 2005; Ser. No. 11/281,907 (Nov. 16, 2005); Ser. No. 11/281,910 (Nov. 16, 2005); Ser. No. 11/281,937 (Nov. 16, 2005); Ser. No. 11/283,517 (Nov. 17, 2005); Ser. No. 11/283,518 (Nov. 17, 2005); Ser. No. 11/454,307 (Jun. 16, 2006); Ser. No. 11/544,309 (Oct. 6, 2006); Ser. No. 11/546,027 (Oct. 10, 2006); Ser. No. 11/601,584 (Nov. 16, 2006); Ser. No. 11/607,837 (Nov. 30, 2006); Ser. No. 11/784,798 (Apr. 10, 2007); Ser. No. 12/053,242 (Mar. 21, 2008); Ser. No. 12/144,209 (Jun. 23, 2008); Ser. No. 12/174,490 (Jul. 16, 2008); Ser. No. 12/235,834 (Sep. 23, 2008), each of which is incorporated by reference in its entirety.

FIG. 3 is an enlarged portion of the encoded microvessel 100 (FIG. 1) taken along the line 3-3 in FIG. 2. FIG. 3 illustrates the identifiable code 120 within the coding region 122. In the exemplary embodiment shown in FIG. 3, the identifiable code 120 is a periodic or aperiodic variation in the effective refractive index and/or effective optical absorption of at least a portion of the microbody 102. The variation in the refractive index and/or effective optical absorption of the microbody 102 provides a predetermined optical output pattern or signal 132 when illuminated with incident light 130. The output pattern of light 132 may be indicative of the identifiable code 120.

In particular embodiments, the identifiable code 120 may be a combination of one or more individual spatial periodic sinusoidal variations in the refractive index that are collocated along the length $L_1$ (FIG. 2) of the microbody 102. Each sinusoidal variation may have a spatial period (or pitch) Λ. As such, the identifiable code 120 may include a grating 121 (or a combination of gratings) that provides the optical output pattern 132 that is indicative of the identifiable code 120 when illuminated by the incident light 130. The output pattern 132 may include a digital pattern having a series of bits indicative of the identifiable code 120. In one embodiment, a bit corresponds to a unique pitch Λ within the grating 121. The grating 121 may also be characterized as a composite or collocated grating. Also, the grating 121 may transform, translate, or filter the incident light 130 into the predetermined output pattern 132. In some embodiments, the identifiable code 120 may be characterized as a holographic code.

As one example, the outer region 124 may be comprised of pure silica ($SiO_2$) and have a refractive index $n_2$ of about 1.458 (at a wavelength of about 1553 nm). The inner coding region 122 of the microbody 102 may include dopants, such as germanium and/or boron, to provide a refractive index $n_1$ of about 1.453, which is less than that of outer region 124 by about 0.005. Other indices of refraction $n_1$, $n_2$ for the coding and outer regions 122 and 124, respectively, may be used, if desired, provided the grating 121 can be impressed in the desired coding region 122. For example, the coding region 122 may have an index of refraction that is larger than that of the outer region 124, the coding region 122 may have an index of refraction that is less than that of the outer region 124, or the coding region 122 may have the same index of refraction as the outer region 124 if desired.

The incident light 130 may have a wavelength λ (e.g., 532 nm from a known frequency doubled Nd:YAG laser or 632 nm from a known Helium-Neon laser). As shown, the incident light 130 is incident on the grating 121 in the coding region 122 of the microbody 102. Other input wavelengths λ may be used if desired provided that the wavelength λ is within an optical transmission range of the microbody 102.

Also shown, a transmitted portion 134 of the incident light 130 passes through the grating 121. The remainder of the incident light 130 may be diffracted or reflected by the grating 121 and form a plurality of beams 136-138 (collectively referred to as the output pattern 132). Each beam 136-138 may have the same wavelength λ as the wavelength λ of the incident light 130 and each beam 136-138 may be diffracted or reflected at a different angle. The different angles of diffraction or reflection may be indicative of the different pitches (Λ1-Λn) that exist in the grating 121. A resultant combination of these individual pitches is the grating 121 comprising spatial periods (Λ1-Λn) each representing a bit in the identifiable code. Accordingly, the identifiable code 120 may be determined by which spatial periods (Λ1-Λn) exist (or do not exist) in a given composite grating 121. The identifiable code 120 may also be determined by other parameters as well. The output pattern 132 may be provided to a detector (not shown), e.g., a CCD camera. The output pattern 132 may be a series of illuminated stripes that indicate ones and zeros of a digital pattern or code of the grating 121. In alternative embodiments, the transmitted portion 134 of the incident light 130 that is transmitted through the identifiable code 120 without being diffracted or reflected may provide an output pattern that is indicative of the identifiable code 120. The portion transmitted 134 (or output pattern) may be detected to determine the identifiable code 120 as well.

Each of the individual spatial periods (Λ1-Λn) in the grating 121 may be slightly different than the others thereby producing an array of unique diffraction conditions (or diffraction angles). When the coding region 122 of the microbody 102 is illuminated from a side at the appropriate angle with a single input wavelength λ (monochromatic) source, the diffracted (or reflected) beams 136-138 are generated. Although only beams 136-138 are illustrated in FIG. 3, more beams may be provided in other embodiments (e.g., 8, 12, 20, and more).

When the identifiable code 120 provides the output pattern 132 (or the transmitted portion 134), the output pattern 132 may be transmitted through the reservoir core 104 or through portions of the coding and outer regions 122 and 124 depending upon the refraction/reflection by the grating 121 and/or angle of the incident light 130. The detector may be configured to detect either transmission of the output pattern.

In particular embodiments, the reservoir core is not required to extend through the portion of the microbody having the identifiable code. For example, the identifiable code can be located in a central portion of the microbody and the reservoir core can form a cup or well at an outer portion of the microbody. As another example, the microbody may have two reservoir cores that extend toward each other from opposite ends of the elongated microbody. However, the two reservoir cores may be spaced apart by a middle region or portion. The identifiable code may be in the middle region of such an alternative embodiment.

Furthermore, the identifiable code 120 is not limited to codes formed by gratings. Additional methods exist for providing a variation in effective refractive index and/or effective optical absorption. Also, as will be described in greater detail below, the identifiable code 120 may be formed in other manners. For example, the identifiable code 120 may be formed through morphological changes along the exterior surface 114. Moreover, the identifiable code 120 is not required to be part of or formed with the microbody 102. In alternative embodiments, the identifiable code 120 may be an oligo-tag that is immobilized to one of the interior or exterior surfaces or somehow attached to the microbody 102. Other encoding parameters known in the art can also be used including, but not limited to, optical labels, mass labels, magnetic labels, and the like.

Returning to FIG. 1, the microbody 102 may have a plurality of identifiable codes 120 located within the coding region 122 of the microbody 102. The identifiable codes 120 may extend parallel to each other and to the core axis 190. As shown, the identifiable codes 120 are the same code (i.e., may provide substantially the same output pattern) and may be distributed about the core axis 190. In some embodiments, the identifiable codes 120 are evenly distributed about the core axis 190. In such embodiments, the locations of the identifiable codes 120 may ensure that at least one identifiable code 120 is positioned to be more accessible for the incident light 130 (FIG. 3) when illuminated from a side of the microbody 102 regardless of the rotational orientation of the microbody 102 with respect to the core axis 190. Furthermore, in some embodiments, the identifiable code 120 is continuously repeated for at least a significant portion along the length $L_1$ of the microbody 102.

Figure 4:
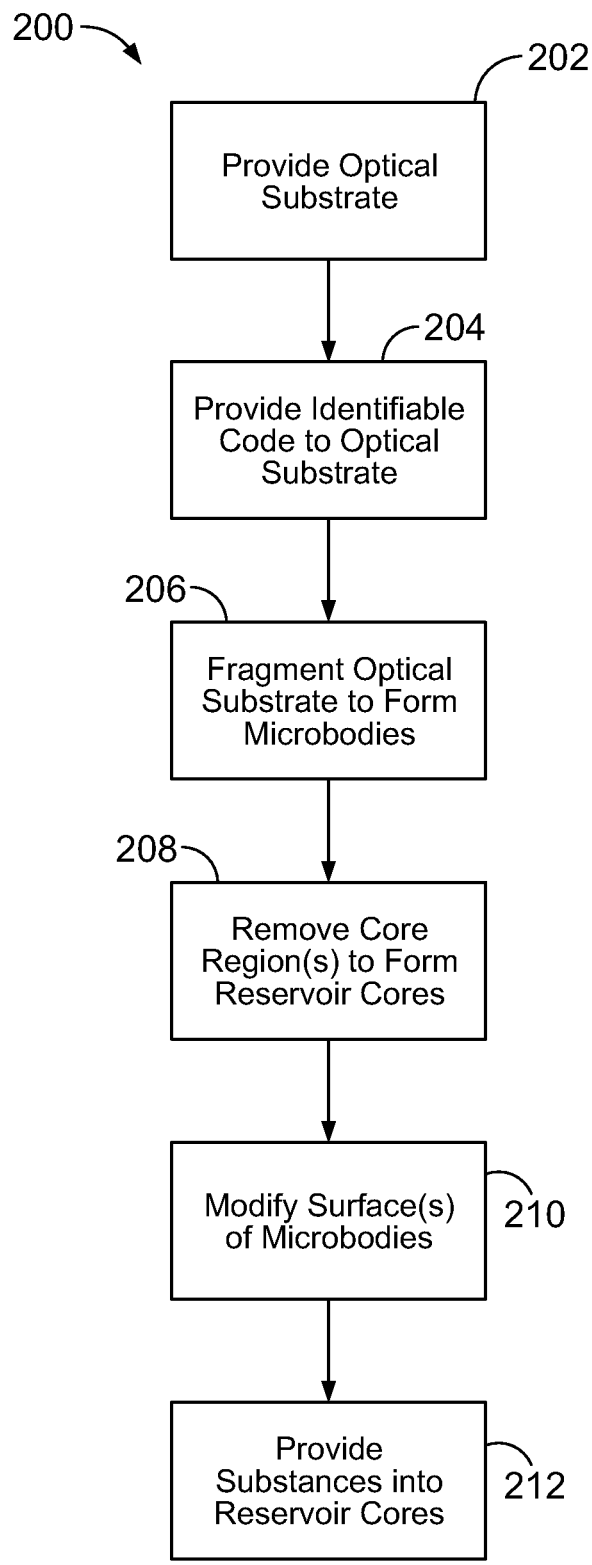
FIG. 4 is a block diagram illustrating a method of manufacturing a plurality of encoded microvessels.

FIGS. 4-21 describe various embodiments related to the manufacturing of a plurality of microvessels, such as the microvessels 100 described with reference to FIGS. 1-3. FIG. 4 is a block diagram illustrating an exemplary method 200 of manufacturing a plurality of microvessels. At 202, an optical substrate is provided that is capable of having an identifiable code formed within a volume of and/or along a surface of the optical substrate. Material of the optical substrate may include at least one of silica glass ($SiO_2$), phosphate glass, borosilicate glass, plastic, co-doped materials (i.e. having more than one dopant such as boron-oxide and germanioum-oxide); doped glasses (e.g. $SiO_2$ doped with quantum dots, fluorescent dyes, rare earth atoms, and other atoms), and rubber. Other useful materials include polymethyl methacrylate (PMMA), cyclo-olefin-copolymer (COC), polycarbonate, polystyrene, polypropylene, and poly(tetrafluoroethylene) (PTFE). Also useful are thermally processable polymers capable of forming holographic images via density gradients. Metal or semiconductor materials are also useful.

In certain embodiments, the optical substrate is manufactured through chemical deposition or vacuum deposition. Thus, any materials capable of forming an optical substrate through such deposition processes may be used. The optical substrate may be shaped, for example, as an optical filament, fiber, rod, brick, block, chip, wafer, and the like. In some embodiments, the optical substrate is a substantially single material (e.g., fused silica). However, in other embodiments, the optical substrate may be a composition or assembly of different materials.

The optical substrate may have a plurality of regions, including a core region and a coding region. The core region may be configured to be removed from the optical substrate and the coding region may be configured to have the identifiable code formed therein. In some embodiments, the core and coding regions have inherent property differences or characteristics that enable the core region to be removed. The coding region may be adjacent to or surround the coding region. However, in alternative embodiments, the core and coding regions may be separated from each other by another region. The other region may have inherent property differences or characteristics with respect to the coding region and the core region.

At 204, at least one identifiable code is written into the coding region of the substrate. As used herein, "writing" includes providing or forming the identifiable code in the optical substrate. For example, "writing" includes impressing, embedding, imprinting, etching, growing, or depositing the identifiable code into the optical substrate. In particular embodiments, the identifiable code is written by illuminating a photosensitive portion of the coding region with an ultraviolet (UV) beam that is filtered by a phase mask or an interference pattern of UV light. However, as will be described in greater detail below, the identifiable code may be written into the optical substrate using other processes.

At 206, the optical substrate is fragmented to form the plurality of microbodies. The fragmenting 206 of the optical substrate may occur before, after, or during the writing 204 of the identifiable code. Fragmenting includes separating the microbodies by chemical methods (e.g., etching) and/or mechanical methods (e.g., mechanically cutting or breaking the optical substrate). The fragmented portions of the optical substrate may include the microbodies of the microvessels.

At 208, the core region of the microbodies is removed thereby forming reservoir cores as described above. Removing the core region may occur before or after the writing of the identifiable code and before or after fragmenting the optical substrate. In embodiments where the material of the microbodies may be etched, e.g., fused silica, the method 200 may use a differential etching process. In the differential etching process, the core region is doped with one or more predetermined dopants (e.g., $GeO_2$ or $B_2O_3$) causing the core region to etch at a faster rate than other regions of the microbodies.

As used herein, "faster rate" or "different rates" includes at least one region being etchable and at least one other region being substantially etch-resistant (i.e., effectively having no etching rate or being non-etchable). For example, the core region can be made of boron-oxide doped silica and regions surrounding the core can be made of germanium-oxide doped silica, such that treatment with acid results in faster etching of the core region to produce a microvessel having a reservoir core.

In alternative embodiments, the removing the core region may occur before fragmenting the substrate to form microbodies. When the core region is removed from the substrate (e.g., through etching), a continuous void may extend through a portion of the substrate. When the substrate is fragmented into a plurality of microbodies, the continuous void within the microbodies becomes the reservoir cores of the microvessels.

Optionally, at 210, interior and exterior surfaces of the microbodies may be selectively modified for the intended purposes of the microvessels. For example, at least one interior surface may be made to be hydrophilic or hydrophobic. Furthermore, surfaces of the microbodies may be modified to facilitate attaching substances to the surface. For example, the surfaces may be modified to facilitate immobilizing oligonucleotides to the surface. Modification of the interior or exterior surfaces also includes immobilizing biomolecules onto the surfaces. In some embodiments, the interior surface may also be modified to facilitate disposing a solid-phase material within the reservoir core.

Optionally, at 212, biological or chemical substances may be provided (e.g., inserted or deposited) into the reservoir cores of the microbodies. The substances may be immobilized onto the interior surfaces, held by the reservoir core, or suspended within a liquid that is within the reservoir core. The substances may include at least one of an analyte and a reagent that is configured to chemically react with the analyte. For example, the substances may include polymerase chain reaction (PCR) reagents and enzymes. The substances may also include nucleic acid templates and one or more primers that are complementary to the templates. The identifiable code may be correlated with a sequence of the nucleic acid template(s) or a sequence(s) of the one or more primers. In other embodiments, a solid-phase material is disposed within the reservoir core. For example, cellulose polymers, polysaccharides, agarose gels, or other gelating polymers may be deposited within the reservoir core.

Figure 5A:
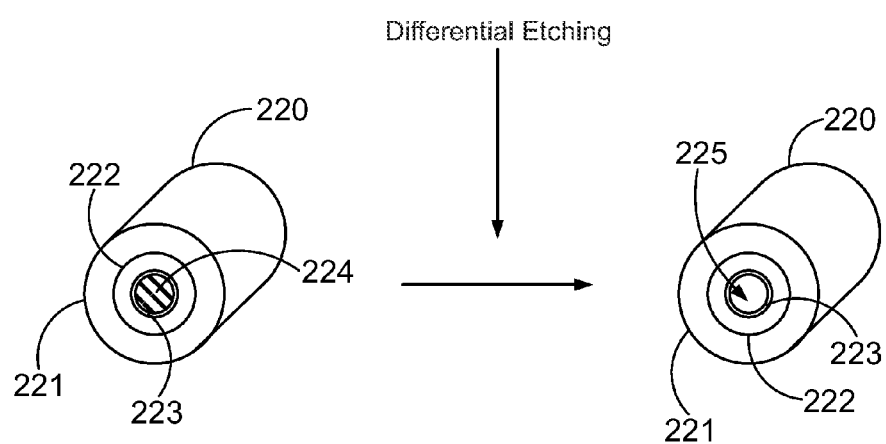
FIG. 5A illustrates an optical substrate before and after undergoing a differential etching process.

FIG. 5A illustrates an optical substrate 220 before and after a differential etching process is applied to the optical substrate 220. The optical substrate 220 shown in FIG. 5A may be formed into a plurality of microvessels or the optical substrate 220 may be already fragmented from a larger optical substrate such that the optical substrate 220 shown in FIG. 5A only forms one microvessel. As shown, the optical substrate 220 includes a plurality of regions 221-224. The optical substrate 220 may be formed through at least one of chemical deposition and vacuum deposition. The material of the optical substrate 220 may be any solid material that may be formed through chemical and/or vacuum deposition (e.g., glass materials). In particular embodiments, the optical substrate 220 is an elongated optical filament comprising fused silica that was formed through Plasma-Activated Chemical Vapor Deposition (PCVD), Advanced Plasma Vapor Deposition (APVD), or Furnace Chemical Vapor Deposition (FCVD). The optical filament may be similar to those used in the telecommunications industry.

However, it is noted that embodiments described herein are not limited to optical filaments and that optical substrates other than optical filaments may be used in alternative embodiments. As one example, optical substrates suitable for embodiments described herein may be manufactured in a similar manner as Vycor® materials manufactured by Corning Incorporated. In that case, a relatively soft alkaliborosilicate glass may be melted and then pressed, drawn, blown, or somehow shaped into a desired but oversized structure. The resultant workpiece may be subjected to additional finishing operations if desired. The workpiece may then be heated above an annealing point but below a temperature that would produce deformation. During this heat treatment, two continuous closely intermingled glassy phases are produced. The first phase is rich in alkali and boric oxide and is readily soluble in acids. The first phase may represent the core region that is to be removed to provide the reservoir core for embodiments described herein. The second phase may comprise a greater percentage of silica such that the second phase is insoluble or relatively insoluble with respect to the first phase. After heat treatment, the workpiece may be placed in an acid solution that is configured to remove the first phase of the workpiece thereby providing a porous high-silica modified workpiece. The porous workpiece may be slowly heated (e.g., to greater than 1200° C.) whereby the porous workpiece is consolidated into the desired microvessel. The desired microvessel may be similar to Vycor products and comprise 96% $SiO_2$ glass or reconstructed glass. A similar process as described above and variations thereof are discussed in further detail in Elmer, Thomas, "Porous and Reconstructed Glasses" *Engineered Materials Handbook*, Volume 4, *Ceramics and Glasses*, p. 427-432 (1992), which is incorporated herein by reference in the entirety.

Other methods of manufacturing microvessels consistent with those described herein may be used. For example, the microvessels may be made by fragmenting capillaries or sheaths that are similar to those used in flow cytometry.

Returning to FIG. 5A, the optical substrate 220 may include a plurality of concentric regions or layers that surround a core region. For example, in the exemplary embodiment, the optical substrate 220 includes an outer region or cladding 221, a coding region or annulus 222, a boundary region 223, and a core region 224. Although four regions are shown in FIG. 5A, other embodiments may include fewer or more than four regions. The regions 221-224 may have different properties that allow the regions 221-224 to be etched at different rates. For example, the optical substrate 220 may be a substantially single material where at least one of the regions 221-224 may be doped to facilitate removing the corresponding region or to facilitate providing an identifiable code within the corresponding region. For example, the optical substrate 220 may be fused silica where different regions of the fused silica have different levels or amounts of dopants.

By way of one example as to the material, properties, and dimensions of the optical substrate 220, the cladding 221 may be pure fused silica having an outer diameter of about 28 μm and an inner diameter of about 12.3 μm. The annulus 222 may have an outer diameter of about 12.3 μm and an inner diameter of about 8.6 μm. The annulus 222 may be fused silica that is doped with $GeO_2$. The dopants may facilitate providing or writing an identifiable code within the annulus 222. A concentration of the $GeO_2$ may be at least about 10.0 wt. % in the annulus 222. The boundary region 223 may have an outer diameter of about 8.6 μm and an inner diameter of about 7.6 μm. The boundary region 223 may comprise pure fused silica similar to the cladding 221. The outer diameter of the core region 224 may be about 7.6 μm. The core region 224 may be fused silica that is doped with $B_2O_3$. A concentration of $B_2O_3$ may be at least 10.0 wt % in the core region 224. In the above example, the substantially single material is fused silica. However, other materials may be used that include dopants or other modifications that facilitate at least one of removing and providing an identifiable code within the material.

In particular embodiments, regions having a low-etch rate compared to the core region may comprise about 4.5 to about 8.5 wt % $GeO_2$ and about 8.0 to about 12.0 wt % $B_2O_3$. The core region (or other regions desired to be removed through differential etching) may comprise about 3.0-8.0 wt % $GeO_2$ and at least about 20.0 wt % $B_2O_3$. In more particular embodiments, regions having a low-etch rate compared to the core region may comprise about 6.5 wt % $GeO_2$ and about 10.0 wt % $B_2O_3$. The core region (or other regions desired to be removed through differential etching) may comprise about 5.0-6.0 wt % $GeO_2$ and at least about 25 wt % $B_2O_3$.

Alternative embodiments of the optical substrate 220 may be used. The regions may have different radial thicknesses and some of the regions may be optional. For example, the boundary region may be optional and not used in other embodiments. Furthermore, the optical substrate may include only a core region and a coding region. In particular embodiments, the cladding may be doped to have a high etch rate and the annulus may include pure silica or another etch-resistant material. The core region may also have a high etch rate. In such embodiments, both the cladding and the core region may be removed through differential etching thereby forming a smaller microvessel. For example, the annulus 222 shown in FIG. 5A may be the only remaining mass after the outer region 221, the boundary region 223, and the core region 224 are removed. Accordingly, one of the inner regions of the initial preform or optical substrate may eventually constitute the microbody of the microvessel after the other regions are removed through differential etching. Such methods may enable production of smaller microvessels.

In some embodiments, the preform or optical substrate may be configured so that the etched interior surface that defines the reservoir core may have desired or predetermined surface properties. For example, in addition to being configured to have a low-etch rate, the boundary region 223 may be configured to have desired material properties. More specifically, the boundary region 223 may comprise a material that facilitates solid-phase synthesis.

Returning to FIG. 5A, the optical substrate 220 or a plurality of optical substrates 220 may be added to an etch solution to remove the core region 224 or core regions 224 if a plurality of optical substrates 220 are present. Since the regions 221-224 have different rates of etching (or different etchabilities), the core region 224 may be removed faster than the other regions. Time and other conditions (e.g., temperature, chemical composition of etch solution, agitation) may be configured to control the etching of the optical substrate(s) 220. After a predetermined or otherwise desired time has elapsed, the core region 224 can be removed thereby creating a reservoir core or a continuous void 225 in the optical substrate 220. The optical substrate(s) 220 may be removed from the etch solution, washed, and further processed for making the desired microvessels. For example, an identifiable code may be added to the optical substrate 220 and/or exposed surfaces of the substrates may be modified.

Figure 5C:
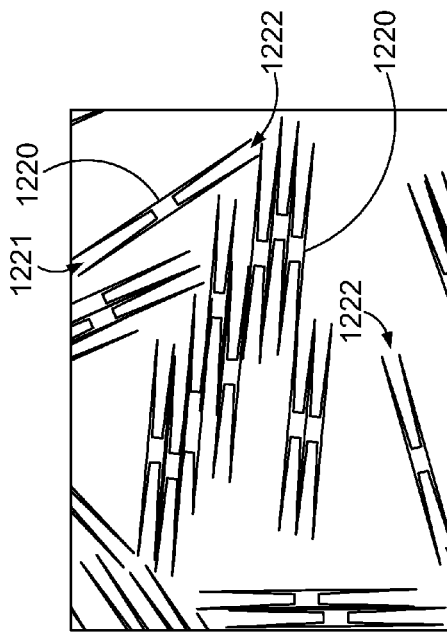
FIG. 5C is an image showing the microbodies in the etch solution after a later, second predetermined period of time.
Figure 5B:
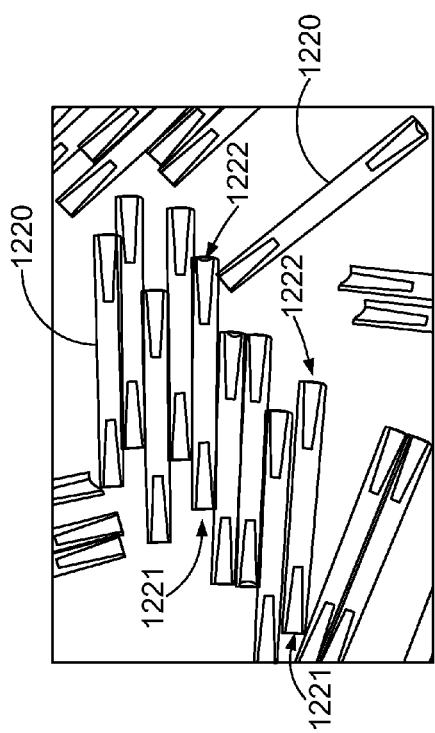
FIG. 5B is an image showing microbodies after a first predetermined period of time in an etch solution.
Figure 5D:
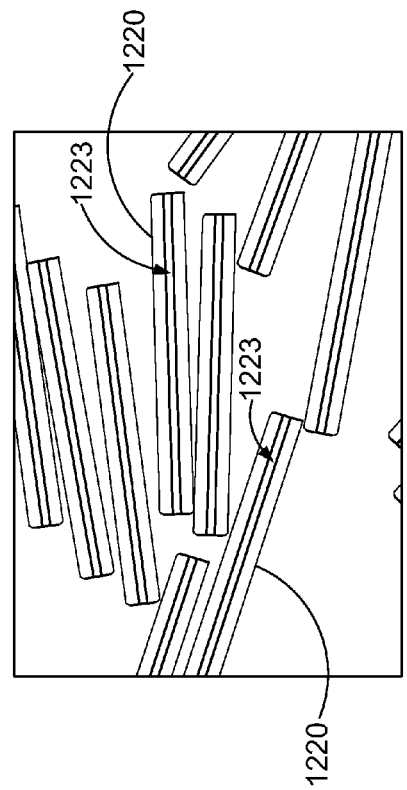
FIG. 5D is an image showing the microbodies after undergoing a differential etching process.

FIGS. 5B-5D illustrate a differential etching process and show images of a plurality of microbodies 1220 after being exposed to an etch solution for different periods of time. As shown, the microbodies 1220 have already been fragmented from a larger optical substrate, such as an optical filament, to form a plurality of microbodies 1220. FIG. 5B shows the microbodies 1220 after four hours within an etch solution, and FIG. 5C shows the microbodies 1220 after six hours within an etch solution. The microbodies include regions, such as regions 221-224 in FIG. 5A, that etch at different rates. As shown in FIGS. 5B-5D, the inner core region etches at a faster rate than the outer region. During the etching process, etch recesses 1221 and 1222 begin to form at opposite ends of each microbody 1220. As the etching progresses, the recesses 1221 and 1222 grow larger (compare FIGS. 5B and 5C) and extend toward each other. The recesses 1221 and 1222 join each other within the corresponding microbody 1220 proximate to a central point along a length of the microbody 1220. As such, the recesses 1221 and 1222 join each other to form a reservoir core 1223 that extends completely through the microbody 1220 (e.g., from one end to the opposite end).

In other embodiments, the microbodies 1220 may be removed from the etch solution before the recesses 1221 and 1222 join each other within the corresponding microbodies 1220. As such, the microbodies 1220 may have two reservoir cores that extend from opposite ends of the microbodies toward each other. In such embodiments, the reservoir cores may be separate from each other so that the reservoir cores are not in fluid communication.

However, in some alternative embodiments, the optical substrate 220 may be formed to include a hollow core such that the above etching steps to remove the core regions are not needed. Such methods of forming hollowed optical substrates 220 may be known by those skilled in the art with respect to optical filaments. For example, capillaries or other hollow filaments can be manufactured using glass drawing techniques such as those used routinely for HPLC applications. In other embodiments, a material having a weakened core can be sonicated to produce a reservoir by removal of the weakened core. Also, solvent etching can be used to remove an inner region of a microbody if the microbody has an outer region that is relatively inert to the solvent under conditions that corrode the inner region.

Figure 6:
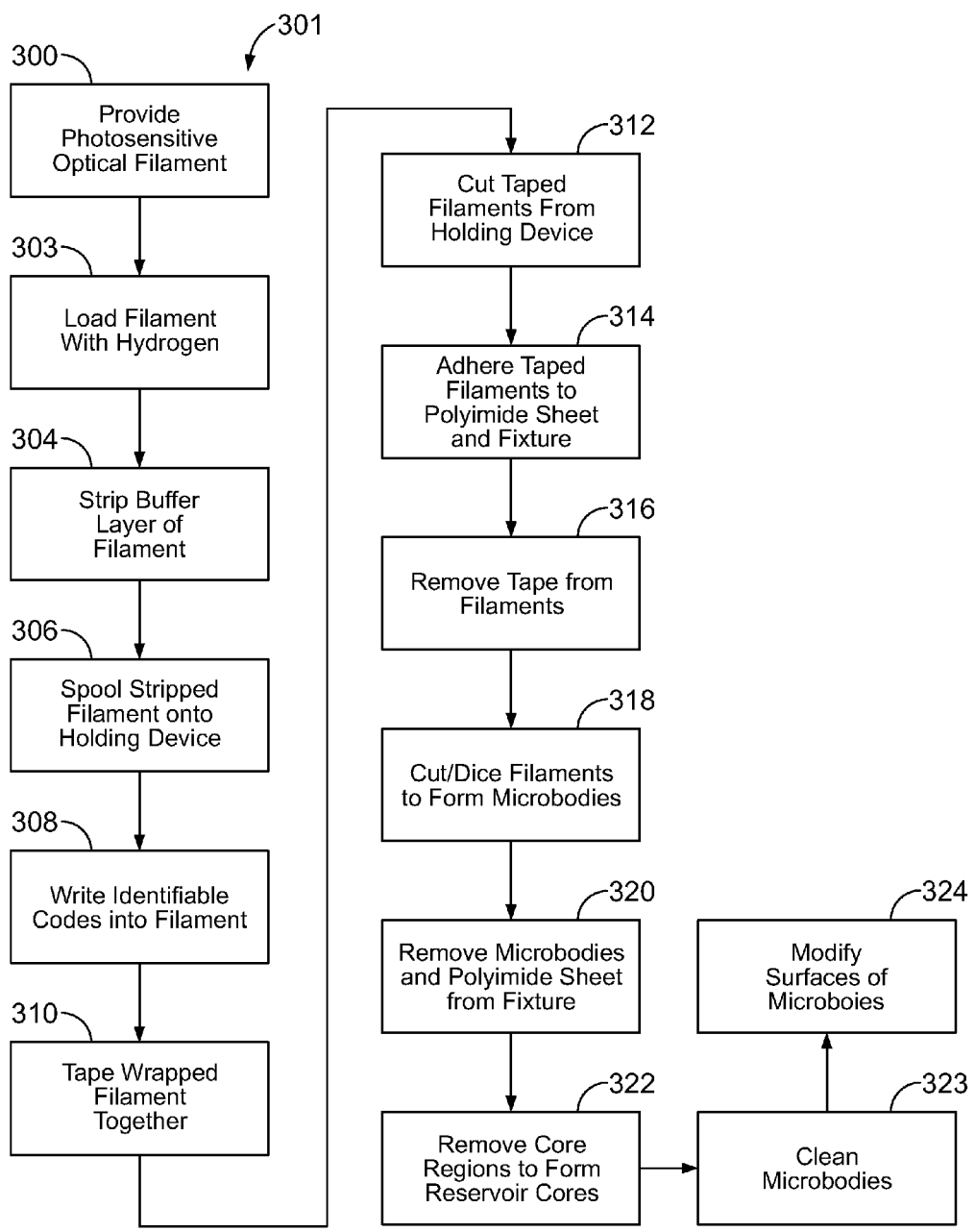
FIG. 6 is a block diagram illustrating a method of manufacturing microvessels in accordance with another embodiment.

FIG. 6 is a block diagram illustrating a method 301 of manufacturing a plurality of microvessels. FIGS. 7-21 provide various views of components and assemblies that may be used in the manufacturing of the microvessels and may be referenced in the description of the method 301. At step 300 in FIG. 6, a photosensitive optical substrate 302 is provided. (The optical substrate 302 is shown in FIG. 8.) The optical substrate 302 is illustrated as an optical filament in FIGS. 7-21. To simplify the following description of the method 301 of manufacturing, the optical substrate will be referred to as an optical filament 302. However, embodiments described herein may be formed from other optical substrates using similar or different manufacturing processes.

Figure 7:
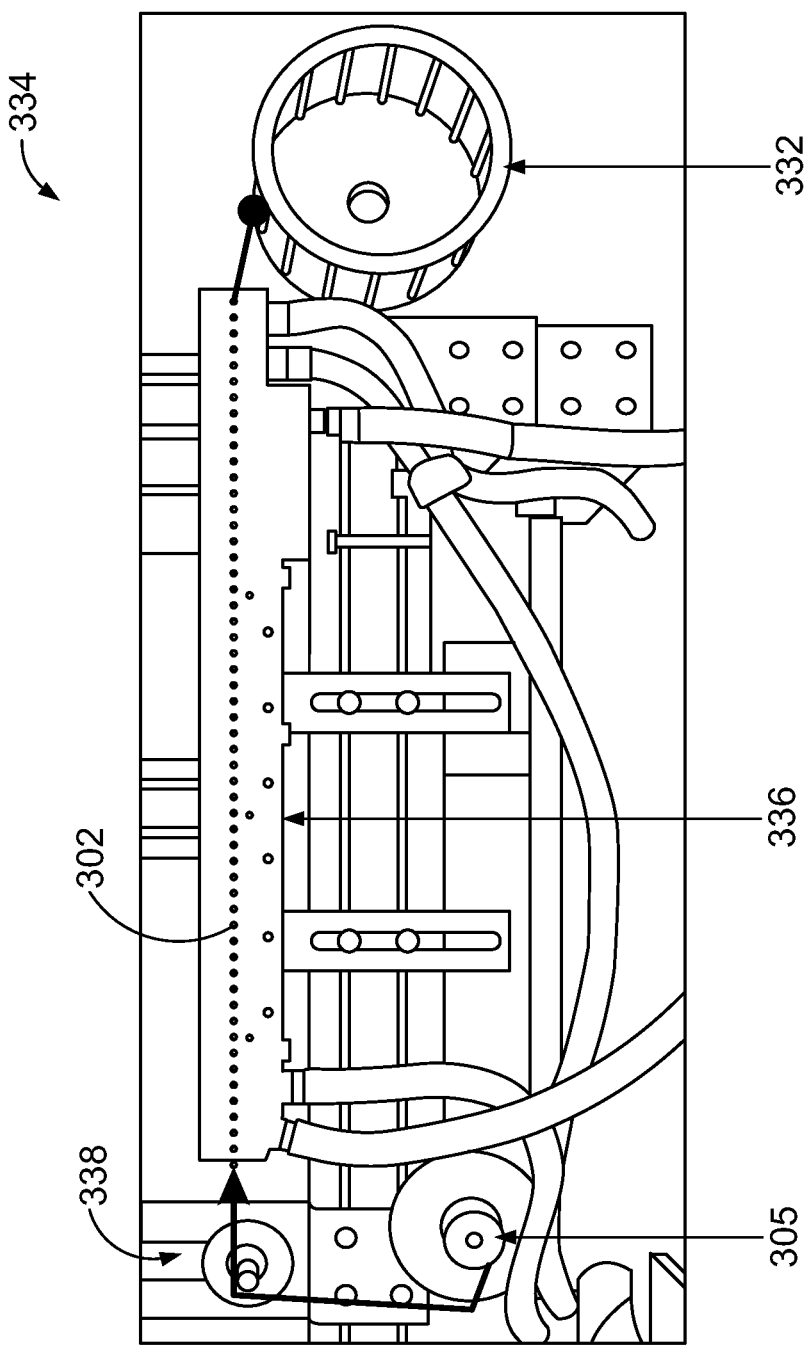
FIG. 7 is aside view of a substrate preparation system.
Figure 8:
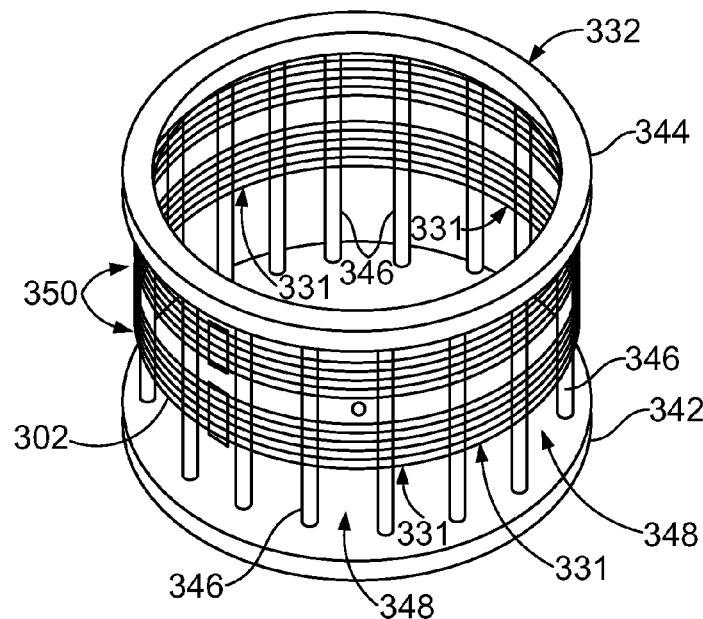
FIG. 8 is a perspective view of a holding device configured to hold the optical substrate while identifiable codes are written into the optical substrate of FIG. 7.

In the exemplary embodiment, the filament 302 is preformed and provided in a spool package 305 (shown in FIG. 7). The filament 302 may comprise a photosensitive material and a buffer layer (e.g., a water-soluble thermoplastic, such as Aquabond® 55, 65, or 85) that surrounds the photosensitive material. Alternatively, the filament 302 may comprise other material(s) as described above with respect to the optical substrate 220 or the microvessel 100. The filament 302 may be doped or loaded with any dopant that allows the filament 302 to have a predetermined level of photosensitivity for incident radiation (e.g., UV or other actinic radiation) that is used to write an identifiable code (also called grating). The dopant may be, for example, hydrogen, deuterium, boron, germanium, lead, and/or other dopants that provide photosensitivity.

In the exemplary embodiment, the filament 302 is provided at 302 without voids or reservoir cores. In alternative embodiments, the filament 302 may already include a void, such as the void 225 shown in FIG. 5, or the void may be formed by removing at least a portion of a core region after formation of the microbodies. The void can form a single chamber or be a part of a porous network or collection of chambers. Also, the void may be formed sometime during or between the steps of the process described below. In particular embodiments, a solid or semi-solid material can be inserted, fully or partially, into one or more voids. Alternatively or additionally, a solid or semi-solid material can cover or cap one or more voids.

At 303, in the exemplary embodiment, the filament 302 may be hydrogen loaded while held by the spool package 305. More specifically, a desired region of the filament 302, such as a coding region and/or a core region of the filament, may be loaded with hydrogen. For example, one or more spool packages 305 may be placed into a high pressure (e.g., greater than 8,000 psi) hydrogen reactor for a predetermined time to load hydrogen into the filament 302. The predetermined time may be at least 24 hours. Optionally, after hydrogen loading, the spool packages 305 may be stored in a low-temperature container to reduce a diffusion rate of the hydrogen from the filament 302 so that the spool packages 305 may be transferred to another location. The low temperature may be, for example, −40° C. and for as long as 72 hours. Each spool package 305 may be removed from the low-temperature container and thawed in a dehumidifying container or oven. When the filament 302 has thawed, the diffusion rate of the hydrogen leaving the filament may increase.

FIG. 7 illustrates a substrate preparation system 334. At 304, after the filament 302 has been warmed to a predetermined temperature, the filament 302 may be stripped of any coating or buffer layer that is disposed on an outer surface of the filament 302 and then cleaned. As shown in FIG. 7, the photosensitive filament 302 is removed from the spool package 305 and threaded through a stripper or strip tube 336 for stripping the buffer layer that surrounds or coats the filament 302. Although not shown, a heater may heat and soften the buffer layer before entering the strip tube 336 to ease the removal of the buffer layer from the filament 302.

The strip tube 336 may be connected to a fluidic system that delivers and removes solvents and other liquids from the strip tube 336 to wash and clean the filament 302. The solvent may be, for example, acetone. The substrate preparation system 334 may control the fluidic system to direct the flow of the solvent onto the filament 302 to remove the buffer layer. After removal of the buffer layer, at 306, the stripped filament 302 is then wound or spooled about a holding device 332. Also shown, the system 334 may include a tensiometer 338 that provides tension in the filament 302 when the filament 302 is removed from the spool package 305 and wound about the holding device 332. The tensiometer 338 may facilitate controlling the winding or wrapping of the stripped filament 302 onto the holding device 332 so that the stripped filament 302 has a desired position or orientation.

Figure 9:
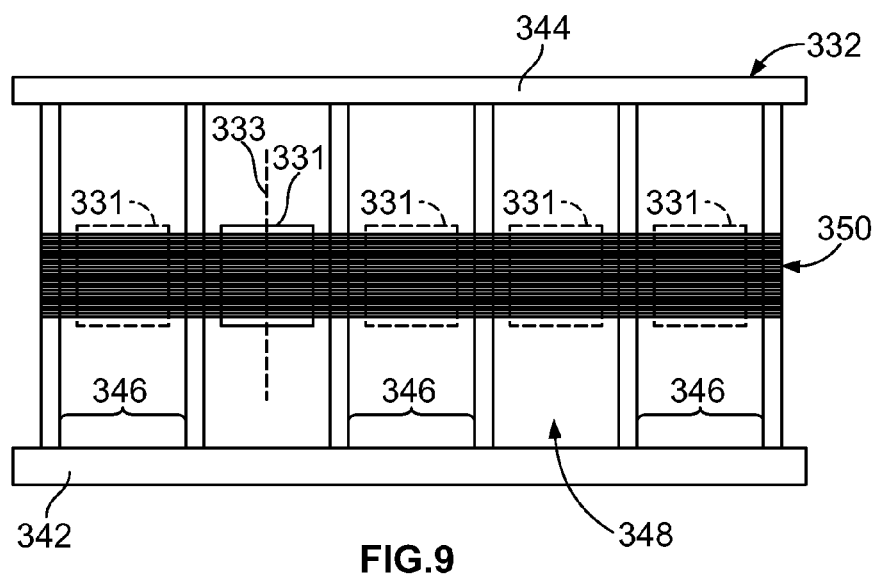
FIG. 9 is a side view of the holding device shown in FIG. 8.

FIGS. 8 and 9 are a perspective view and a side view, respectively, of the holding device 332. The holding device 332 is configured to hold the filament 302 in a desired manner so that identifiable codes may be written into the filament 302. The holding device 332 may be, for example, a cage or basket having a generally polygonal shape. When the filament 302 is wound about the holding device 332, the filament may form filament sections 331 (FIG. 9) of substantially flat areas.

As shown in FIGS. 8 and 9, the holding device 332 has a lower plate 342 and an upper ring support 344 with a plurality of rods or filament-supports 346 connected therebetween and spaced apart from each other. The rods 346 may be equispaced about the circumference of the holding device 332. As shown, the holding device 332 may include a plurality of openings 348. When wound around the rods 346 of the holding device 332, each filament wrap may be adjacent to and touch another filament wrap to form a single layer of a filament ribbon 350 around the holding device 332. The filament 302 may be wrapped around the holding device 332 numerous times (e.g., 100-120) to effectively form the single layer filament ribbon 350. The filament ribbon 350 forms a polygonal shape when wrapped around the holding device 332 to provide a plurality of flat sections 331. The flat sections 331 of the filament ribbon 350 provide an area of the filament 302 where an identifiable code may be written. As shown in FIG. 9, the filament wraps of one flat section 331 of the filament ribbon 350 are taped together at 333, including ends of the filament 302, to maintain tension of the filament 302 around the holding device 332 and to maintain the single layer of the filament ribbon 350. Although only a single filament ribbon 350 is disposed on the holding device 332 shown in FIG. 9, a plurality of filament ribbons 350 may be spaced apart on the holding device 332.

Figure 10:
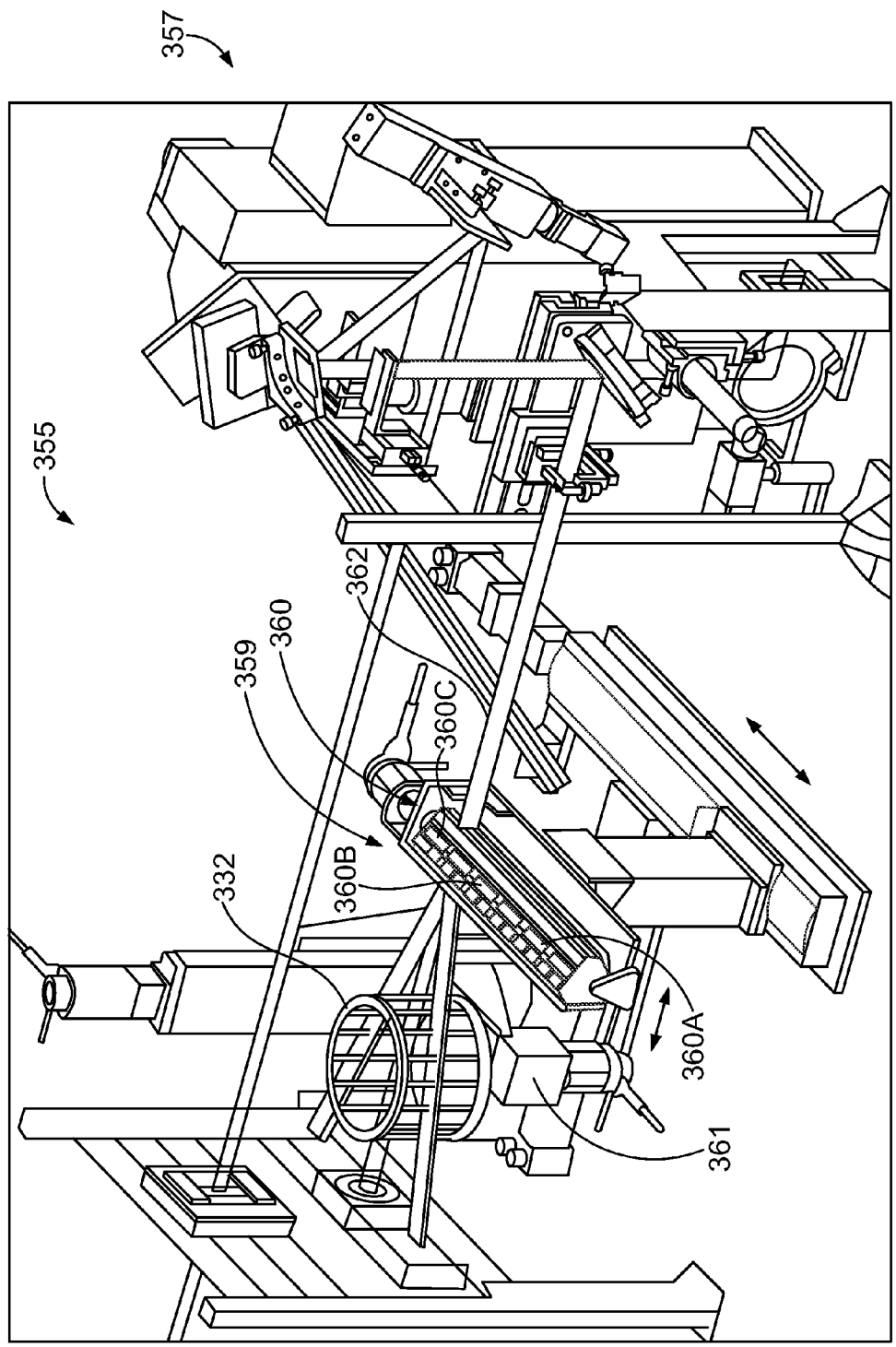
FIG. 10 is a perspective view of a writing system configured to write identifiable codes in the optical substrate in accordance with one embodiment.

FIG. 10 shows a writing system 355 for writing an identifiable code, at 308 (FIG. 6), into the filaments 302 (FIG. 7) of the filament ribbon 350 (FIG. 7). In particular embodiments, providing the identifiable codes includes writing gratings similar to gratings 121 (FIG. 3) described above. As shown, the writing system 355 includes an optical assembly 357, a phase mask assembly 359 having one or more phase masks 360, and a device stand 361 to position the holding device 332. In the illustrated embodiment, a combination of phase masks 360 can be used to write an identifiable code comprising a combination of individual spatial periodic sinusoidal variations in the refractive index that are collocated along the length of the microbody (see, for example, FIG. 2). By way of example, the phase mask assembly 359 may comprise a combination of different phase masks 360A, 360B, 360C. Furthermore, the phase mask assembly 359 may be movable in a lateral or side-to-side direction with respect to a direction of the laser in order to change the phase mask 360. The device stand 361 may also be movable to and from the phase mask assembly 359 to position the filament 302 immediately adjacent to the phase mask 360.

In the exemplary embodiment, during the writing 308 (FIG. 6) of the identifiable codes, the holding device 332 is positioned adjacent to the phase mask assembly 359. (However, FIG. 10 shows the holding device 332 being spaced apart from the phase mask assembly 359.) The optical assembly 357 directs one or more lasers 362, such as a highly coherent 248 nm excimer laser, through a phase mask 360 of the phase mask assembly 359. The laser 362 provides an ultra-violet (UV) beam that passes through at least one of the phase masks 360 to inscribe refractive index modulations into a coding region of the filament 302. For example, a common identifiable code may be written into the filament 302 of a one flat section 331 using phase masks 360A, 360B, and 360C. After the identifiable code is written, the device stand 361 may be rotated about an axis that extends parallel to the supports 346 (FIG. 8) to position another flat section 331 adjacent to the phase mask assembly 359.

Each of the flat sections 331 of the filament ribbon 350 may be written with the same identifiable code (e.g., grating). Alternatively, each flat section 331 may have a different grating written therein such that each flat section 331 has a different identifiable code associated therewith. To provide different gratings for each flat section 331 using the co-located grating method, each flat section 331 would use a different combination of phase masks 360 to write each grating. For example, the first, third and fifth phase masks 360 of the phase mask assembly 359 may be used to write the grating that comprises the three co-located gratings written into a first flat section 331 of the filament ribbon 350. After writing an identifiable code into the first flat section 331, the holding device 332 may be rotated such that a second flat section 331 would be incident upon the UV beam. For the second flat section 331 of the filament ribbon 350, the first, fifth, sixth and eight phase masks 360 may be used to write the grating that comprises four co-located gratings written into the second flat section 331. Other flat sections 331 of the filament ribbon 350 may be similarly written using different combinations of phase masks 360.

Figure 11:
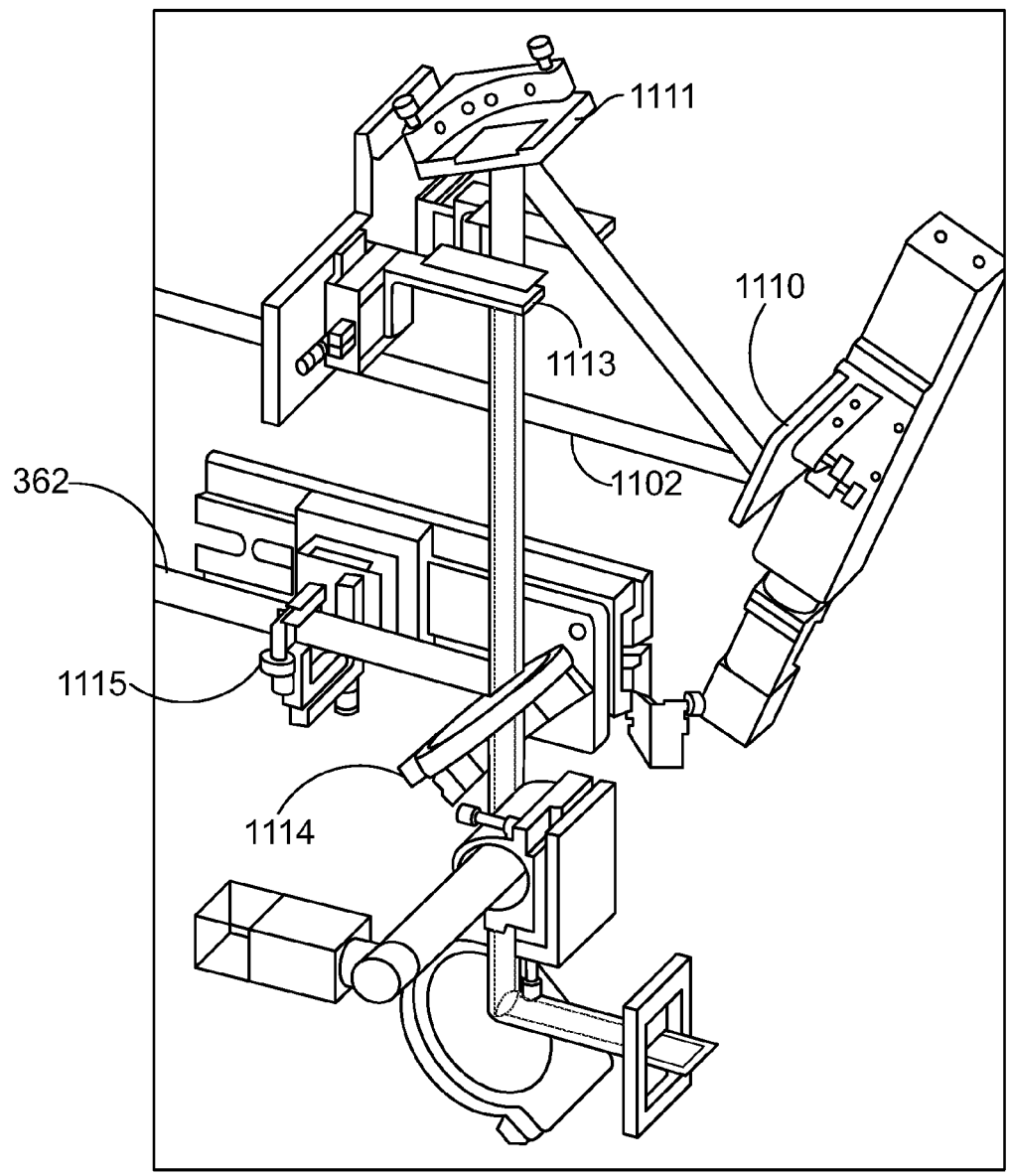
FIG. 11 is a perspective view of an optical assembly used in the writing system of FIG. 10.

FIG. 11 is an isolated perspective view of the optical assembly 357. The optical assembly 357 comprises a series of optical components to transform a rectangular output beam of a laser 1102 into the laser 362 having a line-beam shape. As shown, the laser 1102 is first incident upon an expansion mirror 1110 that reflects the beam onto a re-collimating mirror 1111. The beam may pass through an adjustable aperture 1113 onto a dichroic mirror 1114 that reflects a portion of the beam toward the phase mask assembly 359 (FIG. 10) through a focusing lens 1115.

Figure 12:
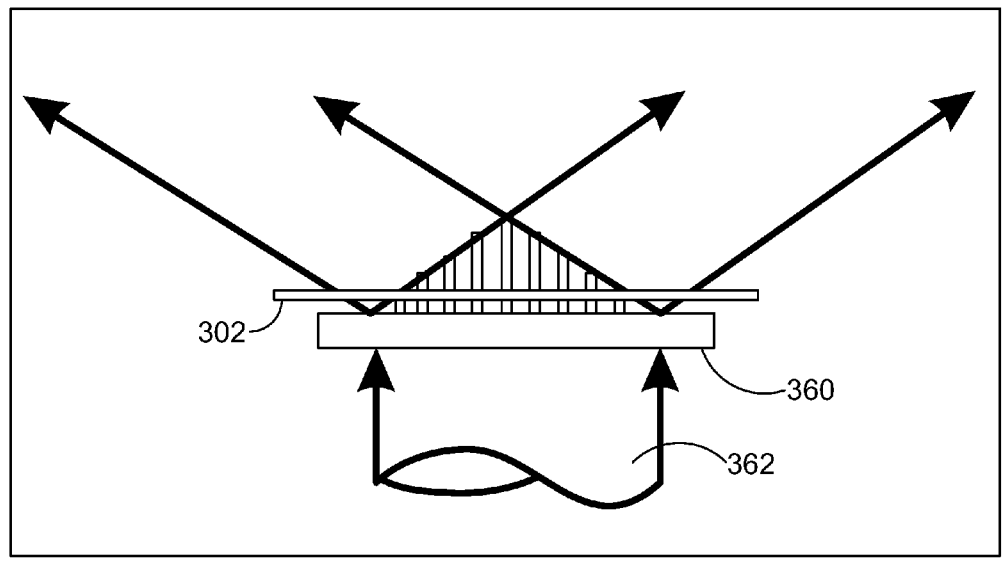
FIG. 12 illustrates a plan view of a filament as an identifiable code is written therein by the writing system of FIG. 10.

FIG. 12 illustrates the incident laser 362 being transmitted through the phase mask 360 to form a three-dimensional interference pattern. In some embodiments, the filament 302 may receive about 20 or fewer pulses per bit of the identifiable code. The filament 302 may be incident with approximately 200 mJ/cm$^2$ at 200 Hz.

Figure 13:
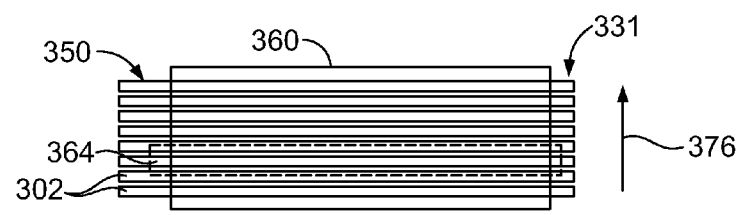
FIG. 13 is a plan view of filament sections of the optical substrate having identifiable codes written therein.

FIG. 13 illustrates a scanning method for exposing each flat section 331 of the filament ribbon 350 using a phase mask 360. As shown, a width of the UV beam 364 may be smaller than a width of the filament ribbon 350. The UV beam 364 may translate along the width of the filament ribbon 350 to scan each of the wraps of filament 302 in the section 331 of filament ribbon 350. For example, the UV beam 364 may be scanned over a small range, such as about 10.8 mm. The beam scan direction 376 may be vertical (i.e., from bottom to top or from top to bottom). The UV beam 364 may be scanned upward by translating the laser 362, or alternatively, the holding device 332 may be moved upward and downward in the axial direction.

Figure 14:
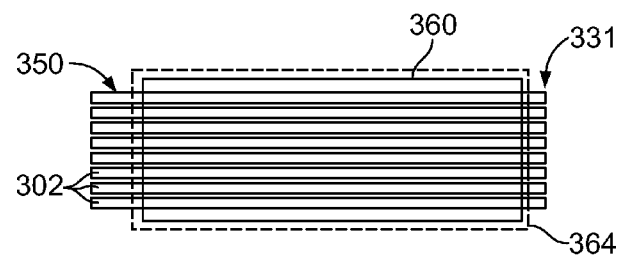
FIG. 14 is a plan view of the filament sections having identifiable codes written therein.
Figure 17:
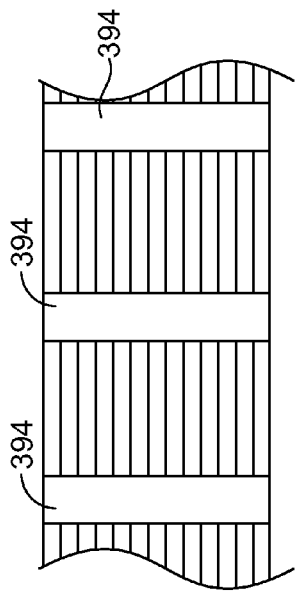
FIG. 17 is an enlarged view of the filaments being processed to form microvessels in accordance with one embodiment.

FIG. 14 illustrates a stationary or blanket method for exposing each section 331 of the filament ribbon 350 using a phase mask 360. As shown, a width of the UV beam 364 used to write the grating is as wide as or wider than a width of the filament ribbon 350. This method enables the entire section 331 to be exposed and a grating written in a single exposure.

Figure 15:
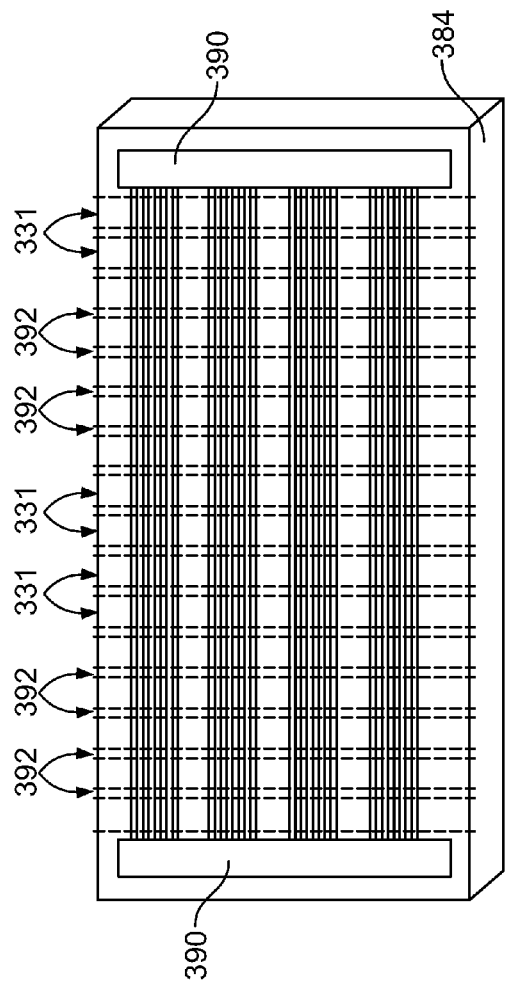
FIG. 15 is a perspective of filaments being held by a thermally conductive fixture.
Figure 16:
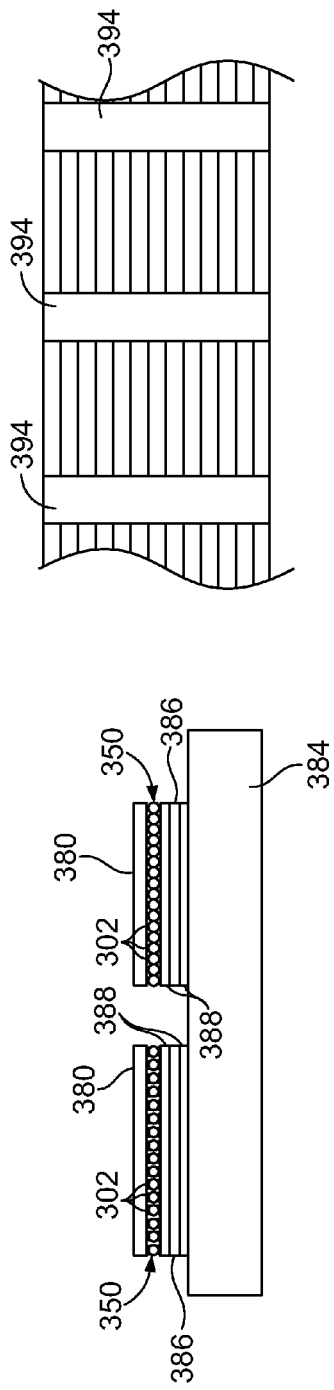
FIG. 16 is a cross-sectional view of the filaments being held by the thermally conductive fixture.

At 310 of the method 301 shown in FIG. 6, the filament 302 of the filament ribbon 350 may be taped together while on the holding device 332 using a tape 380 (FIG. 16). At 312, the tape is cut and the filament 302 adhered to the tape is removed. In step 314 of FIG. 6, the filament ribbon 350 is flattened and mounted to a thermally conductive fixture 384, as shown in FIGS. 15 and 16. As shown in FIG. 16, each ribbon 350 is bonded to a plastic sheet material 386 (e.g., polyimide sheet material) that it is bonded to the fixture 384. An adhesive 388 used to bond the polyimide sheet 386 to the fixture 384 and the filament ribbon 350 to the polyimide sheet 386 may be a water-soluble thermoset adhesive, such as that known as Aquabond®. In FIG. 15, the filament ribbons 350 are secured to the fixture by a pair of clamps 390. An exemplary length of the filament ribbons 350 may be approximately 632 mm. Once the filament ribbons 350 are clamped to the fixture 384, the fixture 384 is heated to liquefy the adhesive 388 (FIG. 16), which then encases the filaments 302 in the adhesive 388. The adhesive 388 is allowed to cool and harden to thereby encase the filaments 302 and bond to the polyimide sheet 386 and bond the polyimide sheet 386 to the fixture 384.

Optionally, at step 316, the tape 380 may be removed from the filaments. However, removal of the tape 380 may occur before, after, or during other steps of the manufacturing process. For example, the tape 380 may be removed after the filament is cut/diced or otherwise fragmented to form the microbodies.

In step 318 of FIG. 6, each section 331 having an identifiable code may be cut or diced to form the microvessels. The intermediate sections 392 may not include identifiable codes. In some embodiments, blades cut sufficiently deep to cut the filaments 302 and score the polyimide sheet 386 without cutting fully through the sheet. A portion of the filament ribbon 350 and the kerfs 394 (FIG. 17) created by the cutting blade. Before removing the filament ribbons 350 from the fixture 384, the intermediate sections 392 may be removed from the polyimide sheet 386. For example, the intermediate sections 392 may be cut away with a blade having a wide kerf. Alternatively, the fixture 384 can be heated to soften the adhesive 388 to permit the intermediate sections 392 of the ribbon 350 to be scraped away. Once the intermediate sections 392 are removed from the filament ribbons 350, the filament ribbons 350 are removed from the fixture 384 by heating the fixture 384 to soften the adhesive between the polyimide sheet 386 and the fixture 384.

Figure 18:
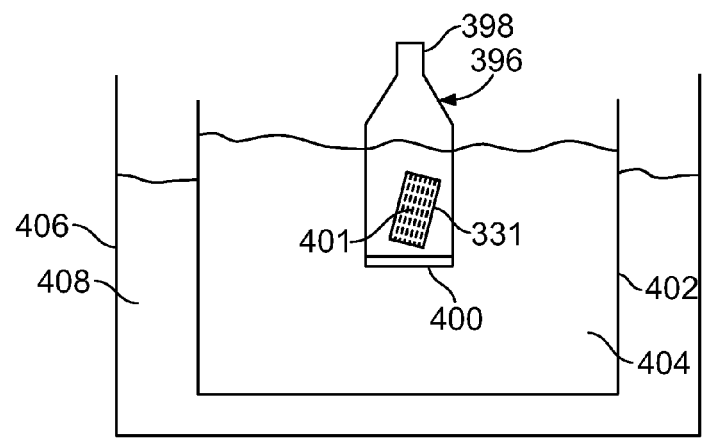
FIGS. 18-21 illustrate microvessels being released from a plastic sheet material in accordance with one embodiment.

In step 320 of FIG. 6, the microbodies are removed from each of section 331 of the filament ribbon 350. The polyimide sheet 386 (with or without the tape 380 thereon) may be cut across each of the intermediate sections to separate each of the sections 331 having a group of microbodies. As shown in FIG. 18, one or more sections 331 having the same code are placed within a container 396 having a tapered open end 398 and another end having a removable filter 400 (40 um filter material). The section having microbodies 401 may be placed into the container 396 by removing the filter 400 and replacing it. The container 396 can be placed filter end down within a vat 402 having water and solvent (e.g., Aquaclean®) solution 404 heated to approximately 86 degrees Celsius. The vat 402 can then be placed within an ultrasonic bath 406 of pure water 408, which agitates or vibrates the water at approximately 80 KHz. The solution may pass through the filter 400 of the container 396 and dissolve the water soluble adhesive 388 holding the microbodies 401 to the polyimide sheet 386. The ultrasonic vibration facilitates separating the microbodies 401 from the polyimide sheet 386.

At 322, the core regions of the microbodies 401 may be removed to form reservoir cores. As described above with respect to FIGS. 5A-5D, the microbodies 401 may be placed in a container having an etch solution. The core regions may etch at a faster rate than other regions of the microbodies. After a predetermined period of time, the microbodies may be removed from the container. Although step 322 is shown as occurring after step 320 and before step 323, the removal of the core regions in the optical filament or the optical substrate may occur at various times throughout the manufacturing process. In some embodiments, the core regions may be removed during step 320 or during step 323.

Figure 19:
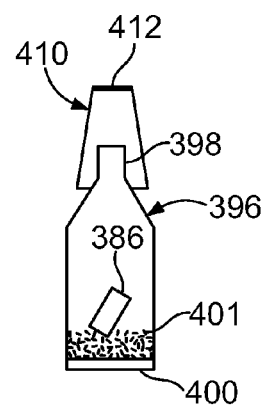
Figure 20:
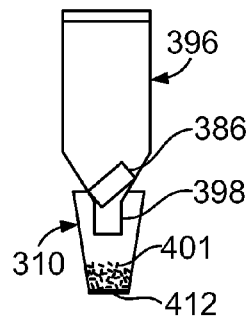
Figure 21:
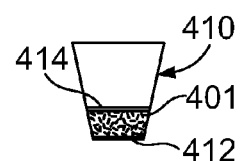

In step 323 of FIG. 6, the microbodies 401 are cleaned and stored. As shown in FIGS. 19 and 20, the container 396 may then be removed from the vat 402 and a polyethylene vial 410 is placed over the tapered opening 398 of the container 396, as shown in FIGS. 19 and 20. The container 396 and vile 410 are then turned upside down and flushed with de-ionized water to clean the microbodies 401. Consequently, the microbodies 401 may flow from the container 396 to the vial 410. The de-ionized water passes through a dense filter 412 disposed on the bottom of the vial 410. The polyimide sheet 386 may be retained within the container 396 because the tapered opening 398 of the vessel is smaller than the sheet 386. Referring to FIG. 21, another filter 414 may be placed in the vial 410 to secure the microvessels therein for storage.

At 324 shown in FIG. 6, surfaces of the microbodies may be modified. Although step 324 is shown as the final step in manufacturing a plurality of microvessels, surface modification may occur at various times throughout the method 301. Furthermore, the above described method of manufacturing microvessels is just one example and the microvessels may be formed in other manners.

In the above described embodiment, the microbodies are fragmented from the filament using a blade or other cutting device. However, in other embodiments, the microbodies may be fragmented using different mechanisms. For example, the filament may be etched to separate the microbodies from each other. The filament may also be etched to form weaker or thinner portions along the filament that are subsequently used as breaking points. A laser may also be used to fragment the filament to create the microbodies.

Figure 22:
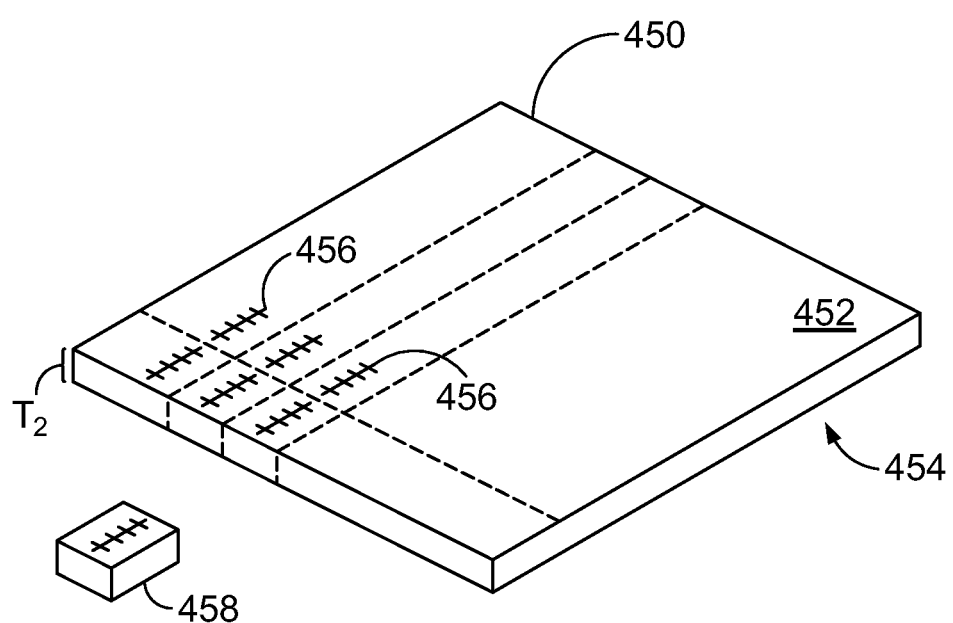
FIG. 22 illustrates another method of manufacturing a plurality of microvessels in accordance with one embodiment.

FIG. 22 illustrates another example of manufacturing a plurality of microvessels. As shown, an optical substrate 450 may be shaped as a rectangular block or plate having top and bottom surfaces 452 and 454 separated by a thickness $T_2$. One or more coding regions (not shown) within the thickness $T_2$ of the optical substrate 450 may be doped as described above. A plurality of identifiable codes 456 may be written into the coding regions within the thickness $T_2$. The identifiable codes 456 may be spaced apart from each other at predetermined locations. The optical substrate 450 may then be etched through the thickness $T_2$ from one surface 452 to the other surface 454 so that a plurality of microbodies 458 are formed where each microbody 458 has an identifiable code 456 within the microbody 458. For example, the optical substrate 450 may be etched in a grid-like pattern (indicated by the dashed lines) such that rectangular microbodies 458 (e.g. square-shaped or parallelepiped) are formed. The identifiable code 456 may extend along a longitudinal axis of the microbodies 458. The microbodies 458 may then be placed into a container (not shown) have an etch solution to remove core regions of the microbodies 458. Optionally, the core regions may extend alongside or through the coding regions so that when the void is formed, the identifiable codes are located alongside proximate to the void. The above example is just one alternative for manufacturing the microvessels and other processes may be used.

FIG. 23 is a block diagram illustrating a method 500 of selectively modifying interior or exterior surfaces of a plurality of microvessels having reservoir cores. In some embodiments, an interior surface that defines the reservoir core may be selectively modified to have at least one of a first substance and a first surface property, and the exterior surface may be selectively modified to have at least one of a second substance and a second surface property, wherein the modification of the exterior surface is different with respect to the interior surface (i.e. the first substance can be different from the second substance and/or the first surface property can be different from the second surface property. Although the following method is described with respect to a plurality of microvessels, the method may be configured to selectively modify surfaces of only one microvessel. Furthermore, in some embodiments, the microbodies may be encoded microbodies that have already been provided with identifiable codes. However, the identifiable code may be provided after the surfaces are selectively modified.

At 502, a plurality of microvessels may be provided. The microvessels may be provided in a container, such as a tray or vessel, or the microvessels may be within a microfluidic circuit. A tray may have a substantially smooth or planar examination surface or may have a plurality of channels formed along the examination surface. In some cases, the channels may be open-sided channels (i.e., grooves). The channels may be shaped to hold the microvessels in predetermined orientations to facilitate selectively modifying the surfaces of the microvessels. Furthermore, channels may be shaped to orient the microvessels to identify the microvessels and/or detect any reactions within the reservoir cores of the microvessels. When the microvessels are provided within a fluidic circuit, the microvessels may be shaped to flow through capillaries or other channels of the fluidic circuit. The microvessels may be buoyant or partially buoyant.

At 504, a first fluid may be inserted into the reservoir cores of the microvessels. A passive process such as diffusion or gravity flow can insert fluid into the reservoir cores. Alternatively, an active process such as application of positive or negative pressure using a mechanical pump can also be used. If the first fluid is a liquid (also called a first solution), the first fluid may have a relatively high boiling point. For example, the first solution may be DMSO. The first solution may be configured to chemically modify the interior surfaces. For example, the first solution may include biomolecules or other chemicals that bind to the interior surfaces. Furthermore, the interior surfaces of the microvessels may have surface properties that facilitate drawing the first fluid into the microvessels through capillary action. For example, the interior surface may be hydrophilic and the first solution may be a polar liquid. In some embodiments, the plurality of microvessels may be deposited into a common container having the first fluid therein. If necessary, the container may be agitated to facilitate inserting (i.e., drawing) the first fluid into the reservoir cores.

At 506, the first fluid can optionally be removed from the ambient environment that surrounds the microvessels. For example, the microvessels may be at least one of washed and evaporated to remove the first fluid. However, although the first fluid is removed from the ambient environment, the first fluid may be retained within the reservoir cores. At 508, the exterior surfaces of the microvessels may then be exposed to a second fluid or condition while the first fluid is retained within the corresponding reservoir cores. For example, the exterior surfaces may be exposed to a reactive gas or a second solution that is added to the container. In other embodiments a reagent can be added or other condition imposed such that the exterior surface of the microvessel is modified. The second fluid may be different than the first solution. In some embodiments, the first and second fluids may be configured to limit or resist chemical interaction with each other. For example, the first and second fluids may be configured to not mix or diffuse into each other. Furthermore, the second fluid may be configured to chemically modify the exterior surfaces of the microvessels. The second fluid may include different biomolecules than in the first solution. The biomolecules may be configured to be immobilized onto the exterior surfaces of the microvessels. Alternatively or in addition to, the second fluid may include chemicals that are configured to modify the surface properties of the exterior surfaces.

As such, a composition may be formed that includes the microvessels and the first and second fluids. The first fluid may be retained within the microvessels and the second fluid may at least partially define the ambient environment that surrounds the microvessels. Optionally, at 510, the composition may be exposed to predetermined conditions to facilitate the chemical modification of at least one of the interior and exterior surfaces. For example, the composition may be exposed to a thermal cycle, exposed to greater or reduced pressure, exposed to an electrical current, or exposed to predetermined wavelength(s) of light. Furthermore, the composition may have additional solutions subsequently added to the composition to facilitate the chemical modification(s). After being exposed to the predetermined conditions, the second fluid (and any additional fluids that were subsequently added) may be removed from the composition. Optionally, the first fluid may then be removed from the microvessels. The microvessels may then be used in an assay or stored for later use.

In alternative embodiments, the microvessels may be exposed to predetermined conditions before the second fluid is added to the composition or after the second fluid is removed from the composition. In other alternative embodiments, the first fluid may chemically modify the interior surfaces of the reservoir cores and be removed from the reservoir cores of the microvessels before the second fluid is added to the container. In such cases, the second fluid may be non-polar and the interior surfaces may be hydrophilic (or vice-versa) to deter the second fluid from being inserted into the reservoir cores. Chemical modification of the exterior surfaces may then occur without affecting the interior surfaces.

In another embodiment similar to the method 500, the microvessels may be prepared such that the first fluid that is retained within the microvessels may be different (i.e., different first fluids may have different biomolecules). For example, a plurality of microvessels may be deposited into a first container having a solution that includes first biomolecules (e.g., a first pair of primers). Another plurality of microvessels may be deposited into a second container having a solution that includes second biomolecules (e.g., a second pair of primes). There may also be additional containers having solutions with different biomolecules. With the corresponding solutions retained with the respective microvessels, the microvessels from the first, second, and any additional containers may be deposited (i.e., pooled) into a common container. A second fluid that is configured to chemically modify the exterior surfaces of the microvessels may then be added to the common container and the resulting composition may be exposed to predetermined conditions as described above. In such embodiments, microvessels may be formed that have similarly modified exterior surfaces but different biomolecules immobilized to the interior surfaces. However, in other embodiments, microvessels having similarly modified interior surfaces may be separated into separate containers where the exterior surfaces are then subsequently modified to have different biomolecules and/or surface properties.

Although the method 500 and alternative embodiments described above have been described as having few steps, the embodiments may include additional steps in order to modify the surfaces as desired.

Figure 47:
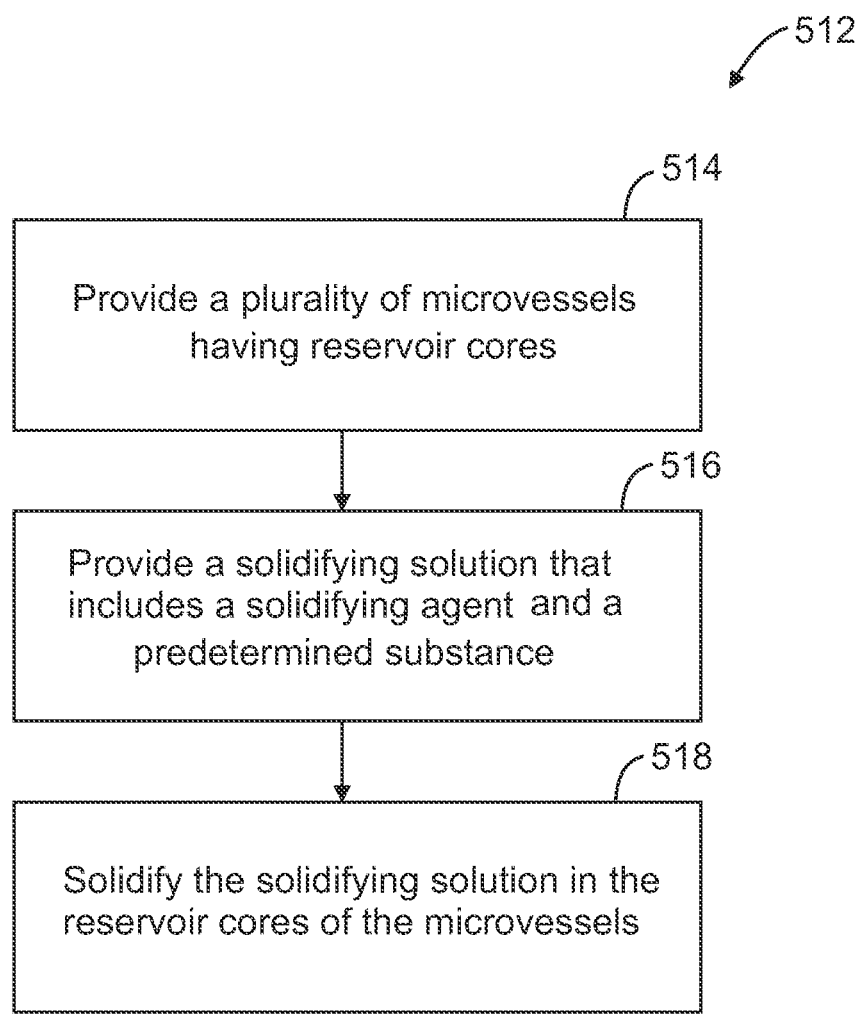
FIG. 47 is a block diagram illustrating a method of providing a solid or semi-solid material into reservoir cores.

FIG. 47 illustrates a method 512 of providing (e.g., depositing or loading) a solid or semi-solid material that includes a predetermined substance into the reservoir cores. The method 512 includes providing, at 514, a plurality of microvessels having reservoir cores. The microvessels may be similar to the microvessel 100 described above. In particular embodiments, the microvessels have identifiable codes that are or will be correlated to the predetermined substance. In embodiments where identifiable codes are desired, a pool of microvessels may be produced in a series of batches where each microvessel of the same batch has the same identifiable code and the same predetermined substance in the corresponding reservoir core. The method also includes providing, at 516, a solidifying solution or mixture that includes a solidifying agent and the predetermined substance so that the solidifying solution is loaded into the reservoir cores. The solidifying solution may then be solidified, at 518, within the reservoir cores so that the predetermined substance is held within the reservoir core.

In some embodiments, the providing and solidifying operations 516 and 518 may include subjecting the microvessels to different thermal conditions to facilitate adding the solidifying solution into the reservoir cores and solidifying the solidifying solution therein. For example, the solidifying agent may be a thickening agent, such as a gelling agent (e.g., agars, agaroses, gelatins, alginates, and the like). The predetermined substance may include, for example, a heat-resistance enzyme (e.g., Taq DNA polymerase) or a fluorescent dye or label (e.g., Rhodamine 6G or fluoroscein). Although one specific example of subjecting the microvessels to different thermal conditions is provided below, those skilled in the art understand that similar methods may be used for loading a solid or semi-solid material into the reservoir cores.

By way of one example, the solidifying mixture or solution may include Rhodamine 6G, 0.01 mM, and agarose, 4% by weight. The solidifying solution may be heated to a predetermined temperature (e.g., about 95° C.) and agitated as the solidifying solution is heated by using, for example, a shaking incubator such as a Vortemp™. The solidifying solution may be agitated (e.g., mixed, shaken, stirred, or the like) at the elevated temperature (e.g., about 95° C.) for a predetermined time period to facilitate diffusing the solidifying solution into the reservoir cores. In the exemplary embodiment, the solidifying solution of agarose and Rhodamine may be slowly cooled to about 50° C. over a period of about 15 minutes. Optionally, the solidifying solution may be centrifuged to compact the microvessels at a bottom of the container. The microvessels may then be removed from the solidifying solution and provided to another solution (e.g., distilled water) that has a predetermined temperature that is, for example, below a solidifying temperature (e.g., about 36° C.). The solidifying solution within the reservoir cores may then solidify so that the predetermined substance is held within the reservoir core.

In addition to the above examples, other materials that are capable of changing from a solid or semi-solid state at a base temperature (e.g., room temperature) to a more liquid state at an elevated temperature may be used. For example, such materials may include or be similar to saturated fatty acids (e.g., palmitic acid or stearic acid) or fatty alcohols (e.g., octadecyl, ceryl, or melissyl alcohol). Paraffin waxes, such as hexacosane and octacosane, may also be used.

In another embodiment, the solidifying operation 518 may include light-activation. For instance, the solidifying mixture may include a liquid photopolymer that will cure when exposed to ultraviolet light and/or visible light. Exemplary photopolymers may be optical adhesives produced by Norland Products (e.g., Norland Optical Adhesive 89). As one particular example, Rhodamine 6G, 0.01 mM, may be mixed with a low viscosity adhesive or photopolymer solution, such as Norland Optical Adhesive 89, to provide the solidifying solution or mixture. The solidifying solution may flow into the reservoir cores when the microvessels are added to the solidifying solution. After the microvessels are added to the solidifying solution, the solidifying solution may be added to another solution having a different density. For example, a higher-density solution may be used, such as an iodixanol solution (e.g., OptiPrep® Density Gradient Medium provided by Sigma-Aldrich). The higher-density solution and the solidifying solution form separate layers or a two-layered solution. The microvessels (having the photopolymers mixed with Rhodamine 6G within the reservoir cores) may be configured to fall to the bottom layer of the higher density solution. The top layer (or the solidifying solution) may then be removed so that the remainder may be essentially the higher density solution and the microvessels having the solidifying solution in the reservoir cores. The microvessels may then be exposed to a curing light (e.g., UV light). For example, the microvessels may be exposed to UV light at 365 nm for a time period that is sufficient to cure the solidifying solution (e.g., about 5 minutes). The photopolymers in the solidifying solution polymerize within the reservoir cores when exposed to the curing light so that the solidifying solution becomes a solid matrix having the predetermined substance.

Figure 24:
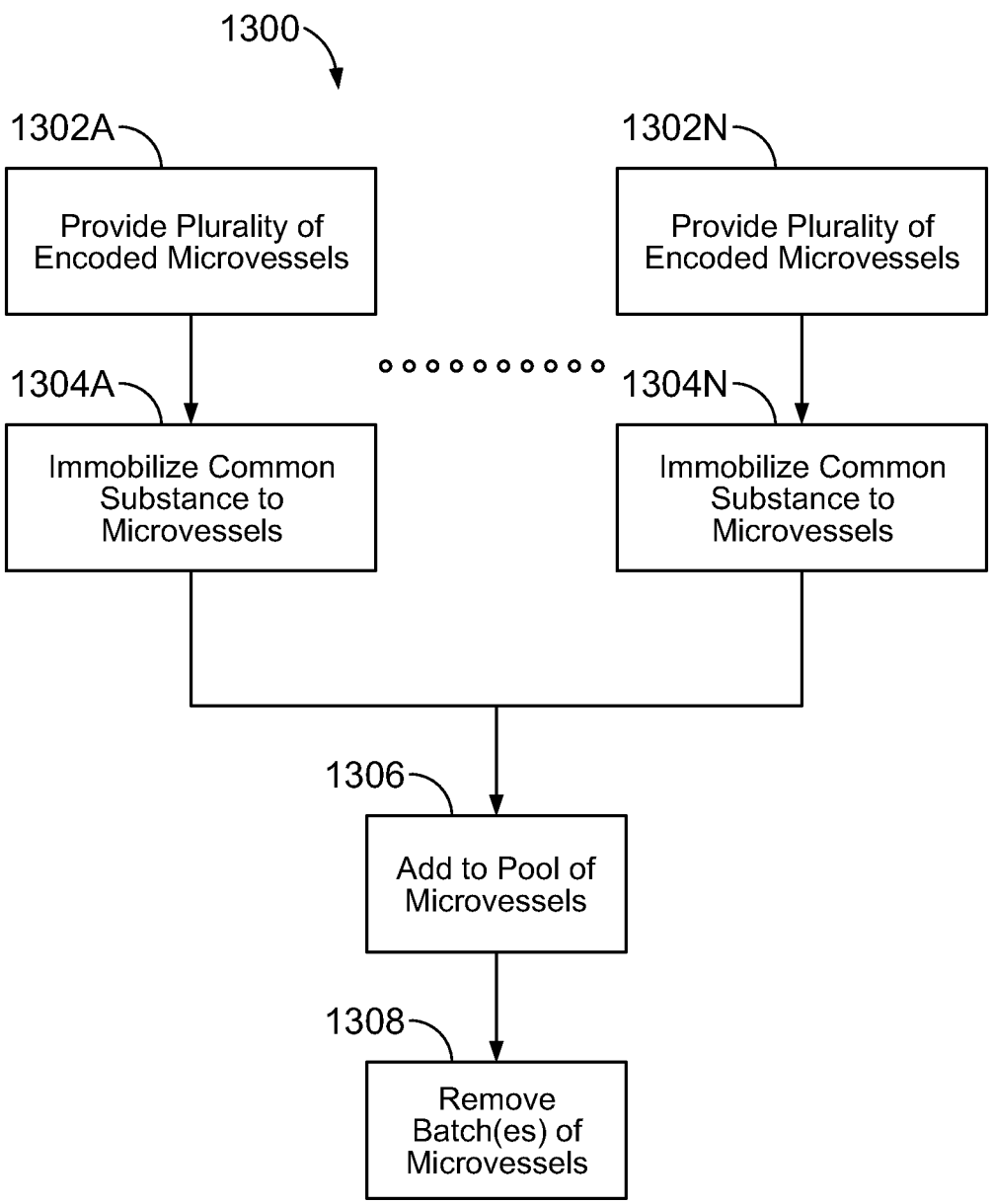
FIG. 24 is a block diagram illustrating a method of preparing a batch of encoded microvessels.

FIG. 24 is a block diagram illustrating a method 1300 of preparing one or more batches of microvessels. Embodiments described herein may require a batch of microvessels where each batch contains a predetermined number of different substances. For example, various protocols may require a batch of encoded microvessels as described above where each differently encoded microvessel has a unique primer pair. As another example, the reservoir cores of the encoded microvessels may contain a solid-phase material that has, for example, an allergen-of-interest attached thereto that is associated with the identifiable code. The microvessels may have other predetermined biomolecules or substances. Initially, to prepare the batch of microvessels, a plurality of encoded microvessels may be provided at 1302A to a common container or fluidic system. The microvessels may have a common or identical identifiable code. At 1304A, a common substance may be immobilized to the microvessels as described above. The substance may be immobilized within the reservoir cores or on an exterior surface of the microvessels. For example, if the substance includes a fluidic medium, the substance may be added to the reservoir cores through capillary forces. Alternatively, an active process such as application of positive or negative pressure using a mechanical pump can also be used. While in the common container or fluidic system, the microvessels may be exposed to various conditions and other media for immobilizing the substance thereon.

As such, each encoded microvessel in the plurality of microvessels may have a common identifiable code and a common substance thereon. Such a plurality of encoded microvessels may also be referred to as a sub-pool of encoded microvessels. As shown in FIG. 24, steps 1302A and 1304A may be performed in parallel with the preparation of a plurality of other sub-pools of encoded microvessels. At 1306, one or more of the sub-pools is added to a larger pool of encoded microvessels. The pool of encoded microvessels may then be mixed together. At 1308, a plurality or batch of the encoded microvessels is removed from the larger pool. The batch of encoded microvessels may include at least one encoded microvessel from each sub-pool of encoded microvessels made during steps 1302 and 1304. The batch of encoded microvessels may then be used in various embodiments described herein where each batch includes individual microvessels having corresponding substances, such as primer pairs, attached thereto. Each unique identifiable code may be associated with a corresponding substance that is immobilized to the microvessel.

FIG. 25 is a block diagram illustrating a method 600 of conducting an assay for biological or chemical analysis. Assays described herein may be used for binding assays or screenings and may include immobilization of a biomolecule within a reservoir core of a microvessel. For example, such screenings may involve specific binding of cells to a molecule (e.g. an antibody or antigen) that is immobilized on a microvessel and followed by analysis to detect whether or to what extent binding occurs. Alternatively, the microvessels may subsequently be sorted and analyzed via flow cytometry. Examples of biomolecules that may be assayed or screened using assays described herein include, agonists and antagonists for cell membrane receptors, toxins, venoms, viral epitopes, allergens, hormones, sugars, cofactors, peptides, enzyme substrates, drugs inclusive of opiates and steroids, proteins including antibodies, monoclonal antibodies, antisera reactive with specific antigenic determinants, nucleic acids, lectins, polysaccharides, cellular membranes and organelles. In addition, embodiments described herein may also be used in hybridization assays where nucleic acids are immobilized on a surface of a substrate, e.g. nucleic acid sequencing, genotyping, polymorphism detection, gene expression analysis, fingerprinting, and other methods of DNA- or RNA-based sample analysis or diagnosis.

Reactions between biomolecules and/or other chemicals may be detected through isotopic and non-isotopic labeling and detection methods. Spectroscopic methods may also be used to determine whether a molecule is bound to a surface coating in a desired configuration. Spectroscopic methods include e.g., UV-VIS, NMR, EPR, IR, Raman, mass spectrometry and other methods. For example, mass spectrometry may also be employed for the analysis of biological macromolecules, which may involve immobilization of a protein on a surface of a microvessel where the protein is then exposed to a ligand binding interaction. Following the ligand binding (or non-binding) the molecule may be desorbed from the surface and into a spectrometer using a laser. The microvessels in the assay may be used as substrates from which to input analytes in the mass spectrometry detection methods described above.

Other types of detectable labels, e.g., radioactive, enzyme linked, or spectroscopic labels may be used to provide optically detectable characteristics. An appropriate detection method applicable to the selected labeling method can be selected. Suitable labels include radionucleotides, enzymes, substrates, cofactors, inhibitors magnetic particles, heavy metal atoms, and particularly chromophores, fluorophores, luminophore, chemiluminescent species, and other spectroscopic labels.

With an appropriate label selected, a system adapted for detection of the label may be selected. An optically detectable system, e.g., fluorescence or chemilumnescence may be used. Other detection systems may be adapted to the purpose, e.g., electron microscopy, scanning electron microscopy (SEM), scanning tunneling electron microscopy (STEM), infrared microscopy, atomic force microscopy (AFM), electrical conductance, and image plate transfer.

Various embodiments may be conducted in an automated or semi-automated manner, generally with the assistance of data processing methods. Computer programs and other data processing methods may be used to store information including, for example, microvessel identifiers, probe sequence information, sample information, and binding signal intensities. Data processing methods may be used to read input data covering desired characteristics.

Embodiments may provide microvessels that compartmentalize desired reactions in multiplexed assays or other experiments. If desired, the microvessels can be uniquely identifiable, for example, based on the characteristics of a substance or reaction occurring in the reservoir core of the microvessel, based on an identifiable code associated with the microvessel, or based on a combination thereof. Some embodiments may enable thousands or millions of parallel reactions, enable large-scale repeated reactions, and increase productivity and reduce time-to-market for drug and other material development industries. Embodiments may be used in many areas such as synthesis of chemicals such as polymers like nucleic acids or peptides whether by combinatorial or other methods, drug discovery, functionalized substrates, biology, proteomics, combinatorial chemistry, DNA analysis/tracking/sorting/tagging, as well as tagging of molecules, biological particles, matrix support materials, immunoassays, receptor binding assays, scintillation proximity assays, radioactive or non-radioactive proximity assays, and other assays, (including fluorescent, mass spectroscopy), high throughput drug/genome screening, and/or massively parallel assay applications. Embodiments may also be used with various genotyping protocols. Although some methods for use of microvessels may be described or exemplified herein in the context of a single reaction, it will be understood that this is done for clarity and that those methods can also be carried out in multiplex formats.

Similar techniques and other assays have been described in U.S. patent application Ser. No. 10/661,234 (filed Sep. 12, 2003); Ser. No. 10/645,686 (Aug. 20, 2003); Ser. No. 10/645,689 (Aug. 20, 2003); Ser. No. 10/661,031 (Sep. 12, 2003); Ser. No. 10/661,082 (Sep. 12, 2003); Ser. No. 10/661,115 (Sep. 12, 2003); Ser. No. 10/661,116 (Sep. 12, 2003); Ser. No. 10/661,234 (Sep. 12, 2003); Ser. No. 10/661,254 (Sep. 12, 2003); Ser. No. 10/661,836 (Sep. 12, 2003); Ser. No. 10/763, 995 (Jan. 22, 2004); Ser. No. 10/956,791 (Oct. 1, 2004); Ser. No. 10/990,057 (Nov. 15, 2004); Ser. No. 11/063,660 (Feb. 22, 2005); Ser. No. 11/063,665 (Feb. 22, 2005); Ser. No. 11/063,666 (Feb. 22, 2005); Ser. No. 11/158,782 (Jun. 21, 2005); Ser. No. 11/187,262 (Jul. 21, 2005); Ser. No. 11/206, 987 (Aug. 18, 2005); Ser. No. 11/226,892 (Sep. 13, 2005); Ser. No. 11/226,914 (Sep. 13, 2005; Ser. No. 11/281,907 (Nov. 16, 2005); Ser. No. 11/281,910 (Nov. 16, 2005); Ser. No. 11/281,937 (Nov. 16, 2005); Ser. No. 11/283,517 (Nov. 17, 2005); Ser. No. 11/283,518 (Nov. 17, 2005); Ser. No. 11/454,307 (Jun. 16, 2006); Ser. No. 11/544,309 (Oct. 6, 2006); Ser. No. 11/546,027 (Oct. 10, 2006); Ser. No. 11/601, 584 (Nov. 16, 2006); Ser. No. 11/607,837 (Nov. 30, 2006); Ser. No. 11/784,798 (Apr. 10, 2007); Ser. No. 12/053,242 (Mar. 21, 2008); Ser. No. 12/144,209 (Jun. 23, 2008); Ser. No. 12/174,490 (Jul. 16, 2008); Ser. No. 12/235,834 (Sep. 23, 2008), each of which is incorporated by reference in its entirety.

Figure 26:
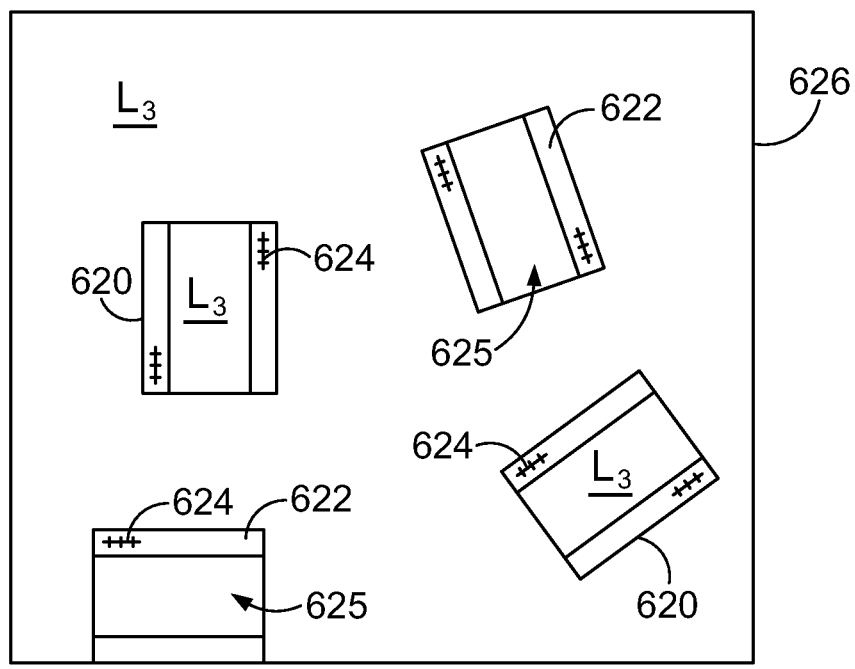
FIG. 26 is a side view of a container having a first liquid and microvessels in accordance with one embodiment held therein.
Figure 27:
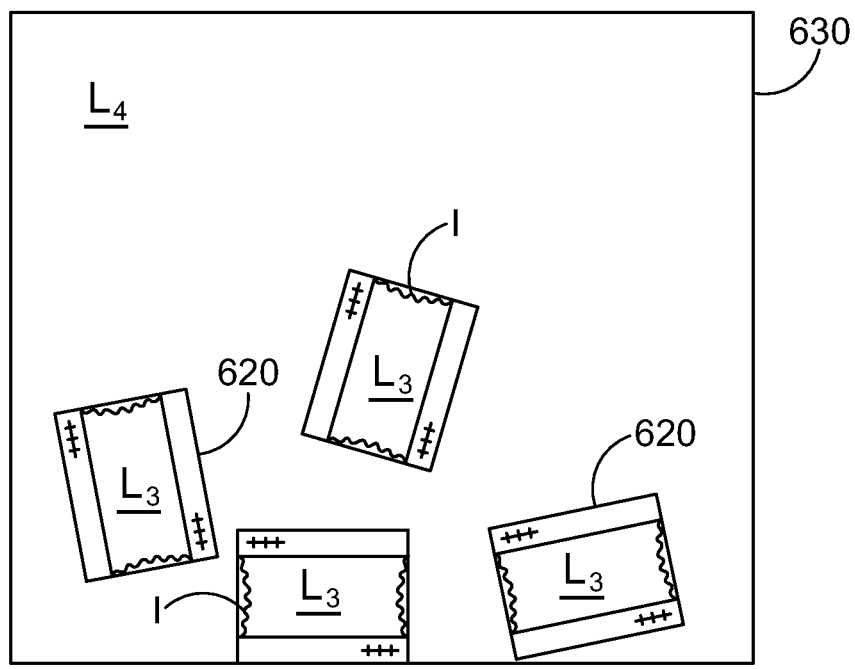
FIG. 27 is a side view of a container having a second liquid and the microvessels of FIG. 25 held therein.
Figure 28:
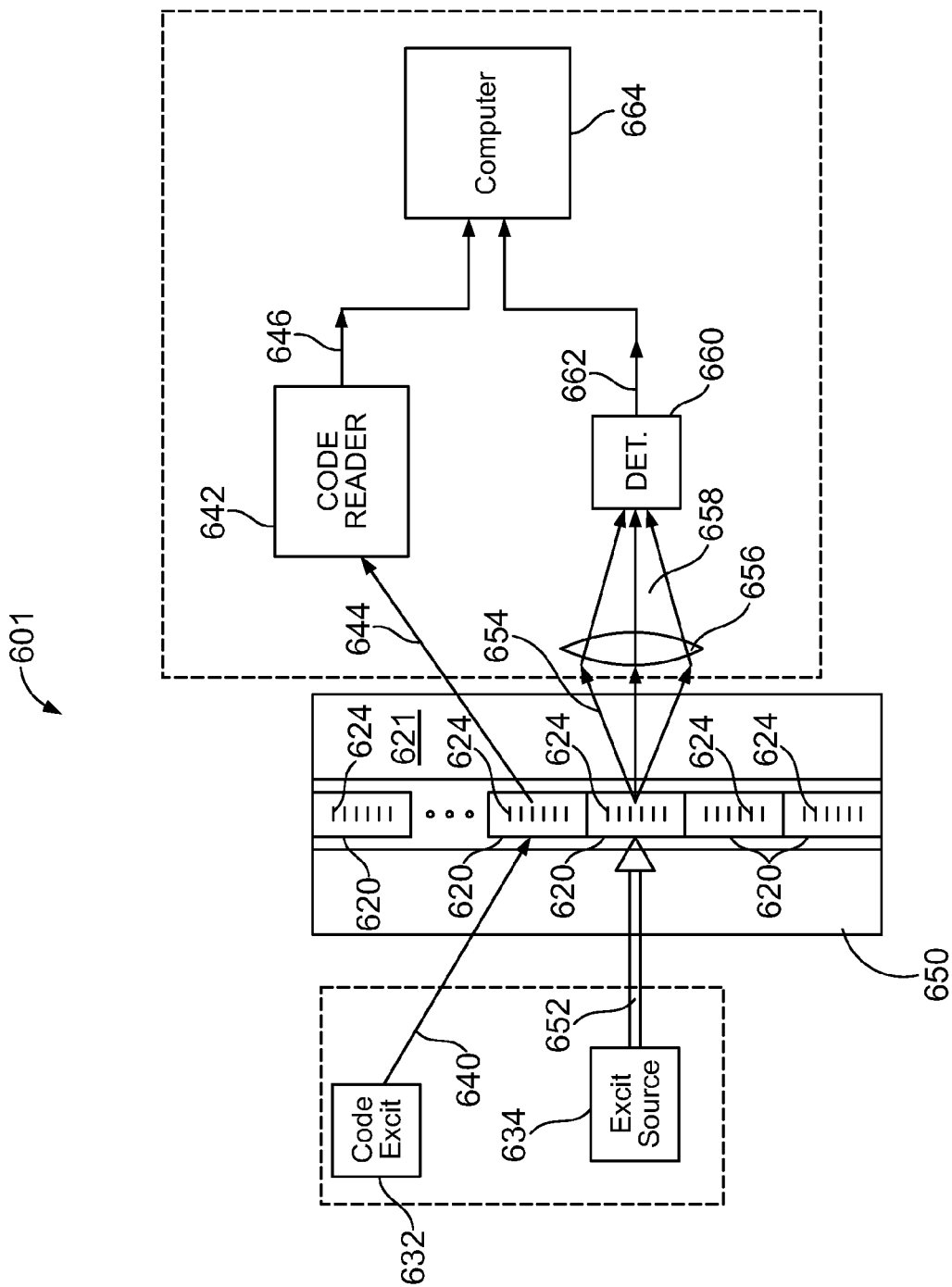
FIG. 28 is a schematic view of a reader system formed in accordance with one embodiment.

FIGS. 26-28 may be referenced with respect to the description of the method 600 shown in FIG. 25. At 602, a plurality of microvessels 620 is provided in a container 626 having a first liquid $L_3$ as shown in FIG. 26. The plurality of microvessels 620 may be a batch of encoded microvessels as described above with respect to FIG. 24. Each microvessel 620 includes a microbody 622 and a reservoir core 625 that holds a substance (not shown) within the reservoir core 625. Optionally, the microbody 622 includes an identifiable code 624. The microbody 622 includes a transparent material that surrounds the reservoir core 625 so that any reactions involving the substance therein may be detected. In the exemplary embodiment, the microvessels 620 include different primer pairs that have been immobilized onto an interior surface that defines the reservoir core 625. Each identifiable code 624 may be uniquely associated or correlated with the primer pair within the reservoir core 625. It will be understood that the method exemplified below can be similarly applied in a configuration where a different template nucleic acid is immobilized onto an interior surface that defines the reservoir core 625 and each identifiable code is uniquely associated with the template within the reservoir core 625. (In such an embodiment, universal primers that are complementary to universal linkers on each template can be introduced to the reservoir cores in liquid $L_3$).

The liquid $L_3$ may be an aqueous liquid having a sample of interest therein. For example, the sample of interest may be cDNA fragments. In such cases, the liquid $L_3$ may also include other components for amplifying the sample of interest through PCR protocols. For example, the liquid $L_3$ may include buffer solution, reagents, enzymes, and dyes.

The interior surfaces of the microvessels 620 may be hydrophilic and configured to draw the liquid $L_3$ into the reservoir core 625. When the microvessels 620 are provided into the container 626, the liquid $L_3$ is inserted into and retained within the reservoir core 625 through capillary action. In some embodiments, a density or number of cDNA fragments suspended within the liquid $L_3$ may be configured so that at most a few cDNA fragments are deposited into the reservoir cores 625 when the liquid $L_3$ is drawn into the reservoir cores 625. At 604, the microvessels 620 are removed from the liquid $L_3$. For example, the liquid $L_3$ may be drained from the container 626 or the microvessels 620 may be collected and moved to another environment. Accordingly, when the microvessels 620 are removed from the container 626, each microvessel 620 may have a primer pair that is different than the primer pairs in other microvessels 620 and also the common liquid $L_3$, which includes the cDNA fragments and other components for amplification. Each different primer pair may be associated with a unique identifiable code 624.

At 606 in FIG. 25, the microvessels may be provided to a container 630 having a second or different liquid $L_4$ therein as shown in FIG. 27. The container 630 may be the same as the container 626 if the liquid $L_3$ were removed and the liquid $L_4$ subsequently added. In FIG. 27, the liquid $L_4$ may be a nonpolar liquid, such as alkanes, oils, and fats. When the microvessels 620 are within the liquid $L_4$, the liquid $L_3$ within each microvessel 620 may be separate and effectively isolated from the liquid $L_3$ in other microvessels 620. For example, the liquid $L_4$ may facilitate retaining the liquid $L_3$ within the corresponding microvessels 620 through a polar liquid/nonpolar liquid interface I shown in FIG. 27.

At 608, the microvessels 620 are exposed to predetermined conditions for conducting desired reactions within the respective reservoir cores 625. In the exemplary embodiment, the container 630 may be subject to a predetermined thermal cycle configured to facilitate or control the reactions occurring within the reservoir cores 625. The thermal cycle may be similar to known PCR protocols for amplifying DNA. In such embodiments, if the microvessels 620 include primers that complement the cDNA fragment within the corresponding reservoir core 625, then the primers may help amplifying mRNA within the reservoir core 625. The amplified mRNA may be labeled for detection. Accordingly, embodiments described herein enable individual microvessels 620 that have different primer pairs to reside in a common ambient environment (i.e., the liquid $L_4$) while compartmentalizing different reactions. The reactions in individual microvessels 620 may be different from the reactions in other microvessels 620 because the microvessels 620 may have different primer pairs and/or cDNA fragments.

The method 600 may also include determining, at 610, optically detectable characteristics of the reactions within the corresponding reservoir cores 625, and also determining, at 612, the identifiable codes 624 of the microvessels 620. The determining steps of 610 and 612 may occur at approximately the same time or one determining step may occur before the other. For example, the identifiable code 624 may be determined by illuminating the microvessel 620 with a first light beam and the optical characteristics of the reactions may be determined using a second light beam. Alternatively, the microvessels 620 may be collectively imaged and the optically detectable characteristics and the identifiable codes 624 of the microvessels may be determined. For example, a first image may be to determine the identifiable codes 624 and a second image may be to determine the optical characteristics within the reservoir cores 625. However, in some embodiments, both the optical characteristics and the identifiable codes 624 of the microvessels 620 may be determined from a single image. Subsequent image analysis software may be used to determine the identifiable codes as well as any degree that a reaction occurred within the reservoir core 625. Furthermore, the method 600 may optionally include sorting, at 614, the microvessels 620 based upon at least one of the identifiable codes 624 and the detected optical characteristics.

In some embodiments, determining a detectable characteristic includes detecting the detectable characteristics in real-time as the reactions are occurring in the reservoir cores 625. Thus the progress of reactions can be measured in response to various conditions including, but not limited to, introduction of a reactant, catalyst or other chemical species; excitation by radiation; increase in temperature or the like. For example, nucleic acid amplification occurring in a reservoir core can be detected in real time using methods known in the art such as real-time PCR. Exemplary real-time PCR methods are described in U.S. Pat. Nos. 7,422,850 and 6,814,934, each of which is incorporated herein by reference in its entirety. Alternatively or additionally, detection can occur before a reaction is initiated or after a reaction is substantially complete.

Various methods may be used for providing the detectable characteristic of a desired reaction (e.g., selective hybridization or binding events). In particular embodiments, a microvessel can be used to detect or quantitate a nucleic acid in a real time PCR protocol. For example, various methods described herein may use a fluorescent dye (e.g., SYBR® Green I, EvaGreen™, BOXTO, LCGreen™) that has a significantly greater fluorescent output when incorporated into double-stranded DNA as compared to when the fluorescent dye is in free (i.e., unbound) in the solution. Other dyes or labels may be used, such as Goldview, Nancy-500, SYTO-18, and SYTO-82. In addition, dye-primer based signaling systems (e.g., hairpin primer signaling such as LUX™) may also be used. Probes having reporters and quenchers on opposite ends may also be used. Probe-based assays systems, such as TaqMan® probes, Molecular Beacons®, minor groove binding (MGB) probes, Locked nucleic acid (LNA) probes, and hybridization probes may be used. Similar and other detection chemistries and protocols are described in greater detail in *Real-Time PCR*, edited by M. Tevfik Dovak, 2006; U.S. Pat. No. 6,245,514; U.S. Pat. No. 5,538,848; U.S. Pat. No. 6,174,670 and U.S. Pat. No. 5,804,375, each of which is incorporated by reference herein in its entirety. When the above examples are employed during real-time PCR, a low fluorescent signal may be increased proportionally during each succeeding PCR cycle in tandem with an exponential increase in the DNA products formed.

Additional detection methods may include luminescence, fluorescence resonance energy transfer (FRET), fluorescence polarization, mass spectrometry, and electrical detection. Such detection mechanisms as well as others are briefly described in Kwok, Pui-Yan "Methods for Genotyping Single Nucleotide Polymorphisms," Annu Rev. Genomics Hum. Genet. 2001. 2:235-58, which is incorporated by reference herein in the entirety. The Kwok article also describes various genotyping methods that may be suitable for embodiments described herein.

The optically detectable characteristics from the reservoir cores 625 described above with respect to FIGS. 25-27 may be indicative of a number or amount of amplicons that are produced by nucleic acid amplification within the reservoir cores 625. Each amplicon may have a detectable label (e.g., fluorescent label) that emits a fluorescent signal when excited by light energy of a predetermined wavelength. By determining those primer pairs that chemically reacted with the sample of interest (i.e., those that were extended in a PCR process), the sample of interest may be identified and/or properties of the sample of interest may be identified. As set forth in further detail below, the sequences of the primer pairs can be associated with a code that is present in or on the microvessel, thereby facilitating convenient identification of sample of interest or a property of the sample.

FIG. 28 illustrates an exemplary detection system or device 601 for determining the identifiable code 624 (FIG. 26) and optical characteristics of reactions occurring within select reservoir cores 625 (FIG. 26). The detection device 601 includes a code excitation source 632, a fluorescent excitation source 634, and a container 650 having an examination surface 621 positioned relative to the code excitation and fluorescent excitation sources 632 and 634. The microvessels 620 may be provided to the detection device 601 in a random manner. For example, the microvessels 620 may flow in a fluidic medium onto the examination surface 621 such that the microvessels 620 fall in a random manner onto the examination surface 621. The container 650 may be, for example, a tray having flat or grooved surfaces or an enclosed channel (capillary tube or flow cell) that align the microvessels 620. However, the examination surface 621 may also be a flat or substantially smooth surface.

The microvessels 620 may be aligned into a desired orientation on the examination surface 621. For example, the reservoir cores 625 of the microvessels 620 may be aligned with respect to each other. Furthermore, the examination surface 621 may align the microvessels 620 end-to-end along a common axis as shown in FIG. 28. Although FIG. 28 only illustrates one channel or groove, the examination surface 621 may have a plurality of enclosed channels or open-sided channels (i.e., grooves) that extend parallel to each other. Microvessels can be aligned using methods and devices for aligning elongated particles such as the methods and devices set forth in U.S. Pat. No. 7,164,533, which is incorporated herein by reference in the entirety, and U.S. Pat. No. 7,399,643, which is also incorporated herein by reference in the entirety.

When microvessels described herein are provided to an examination surface, the microvessels may be dispensed or randomly provided such that the microvessels have random locations on the examination surface and/or different orientations with respect to each other. In some embodiments, the microvessels are configured to fall randomly onto their sides or in such a manner that the elongated core axes of the microvessels extend along a common plane (or extend substantially parallel to a planar examination surface). In such embodiments, the identifiable codes may be determined and the reservoir cores may be viewed or imaged to determine if a reaction has occurred or is occurring within the reservoir cores. In more particular embodiments, the core axes of the microvessels are aligned in a common direction so that an input light (or code-reading beam) may move along the microvessels and be incident upon the microvessels in substantially the same manner to determine the identifiable codes. For example, a linear channel extending along a channel axis may have a plurality of microvessels whose core axes extend parallel to the channel axis. The input light may move along the channel and be incident upon the identifiable code at substantially the same angle. In each of the above embodiments, the microvessels may have different rotational orientations about the core axis, but the microvessels may still be readable and the substances within the reservoir cores may still be detectable.

Returning to the exemplary embodiment in FIG. 28, the identifiable codes 624 in the microvessels 620 may be detected when incident light 640 (also called code-reading beam) from the code excitation source 632 illuminates at least one of the microvessels 620. The identifiable code 624 may provide an output light signal or pattern 644 to a reader 642. In the exemplary embodiment, the incident light 640 is diffracted by, reflected by, or transmitted through the identifiable code 624 to provide the output pattern 644 to the reader 642. The reader 642 may include the optics and electronics necessary to read the output patterns 644 provided by the identifiable codes 624. The reader 642 provides a signal on a line 646 that is indicative of the identifiable code 624 in each microvessel 620.

The incident light 640 may be directed transversely from a side of a container 650 (or from an end or any other angle) with a narrow band (single wavelength) and/or multiple wavelength source. Other illumination, readout techniques, types of identifiable codes, geometries, containers, and materials may be used for the microvessels 620. For example, the microvessels 620 may be imaged as a group.

Furthermore, a second or optical excitation signal or beam 652 may be provided from the fluorescent excitation source 634 that is incident upon the microvessels 620 in the container 650. If the microvessels 620 have fluorescent substances, such as nucleic acid amplicons, within the reservoir cores 625 (FIGS. 26-27), a fluorescent optical output light signal 654 (or emission signal) may be emitted from such microvessels 620. The fluorescent optical output signal 654 may pass through a lens 656 that is configured to focus light 658 to an optical fluorescence detector 660. Instead of or in addition to the lens 656, other imaging optics may be used to provide the desired characteristics of the optical image/signal onto the fluorescence detector 660. The detector 660 may then provide an output signal on a line 662 that is indicative of the amount or level of fluorescence within a corresponding microvessel(s) 620. These observed reactions may provide data that is subsequently analyzed. The data may facilitate identifying an unknown target analyte.

The container 650 may comprise glass material, plastic, or any other material that is transparent to the code-reading incident light 640 and the output pattern 644. The container 650 may also be transparent to the fluorescent excitation beam 652 and the output fluorescent optical signal 654. The container 650 may be configured for various desired applications or experiments, including harsh temperature ranges, harsh chemicals, or other application specific requirements. Exemplary containers (e.g., positioning devices, trays, plates) for aligning elongated microbeads to interrogate with incident light and detect fluorescence therefrom are described in U.S. Pat. No. 7,399,643 and U.S. Patent Application Publication No. 2006/0063271, both of which are incorporated herein by reference in the entirety. The exemplary containers described in these documents may also be used with respect to the microvessels described herein. The material of the container itself need not be transparent to the code reading incident light. For example, code reading need not be performed in the container or the code-reading incident light can be directed in a way that avoids obstruction by the container.

The identifiable code signal 646 from the code reader 642 and the fluorescent signal 662 from the fluorescence detector 660 can be provided to a computing device 664. The computing device 664 can receive the identifiable code signal 646 associated with each microvessel 620 and can determine the known biomolecule or chemical that was bound to or retained in the interior surfaces of the microvessels 620. For example, the computing device 664 may determine the primer pair or template nucleic acid that was immobilized within the reservoir core 625 from a predetermined table that correlates a predetermined relationship between the identifiable code 624 and the primer pair or template. In addition, the computing device 664 may determine a degree or level of fluorescence associated with each microvessel 620. The computing device 664 may then correlate the level of fluorescence or other detectable property with the known substance (e.g., primer pair or template of nucleic acid) that is associated with the identifiable code to determine information about the unknown target analyte (e.g., nucleic acid). The information may be displayed on a display or printout and the information may also be stored in a storage medium or remote database for review and/or analysis.

In alternative embodiments, the identifiable code excitation light 640 and the fluorescence excitation light 652 may be provided by one source beam. For example, the input optical signal may be a common wavelength that performs both functions simultaneously, or sequentially, if desired.

In alternative reading or detection systems, the microvessels 620 may flow through a microfluidic circuit or capillary tube in a fluidic medium, such as in a flow cytometer or flow analyzer. The identifiable code 624 and any fluorescence emitting from the reservoir core 625 may be detected as the microvessels flow alongside a code detector and/or a fluorescence detector.

In particular embodiments, one or more microvessels can be moved or transported under the influence of an electric field. For example, a microvessel that is loaded to hold one or more substance in a reservoir core can be used to transport the substance(s) from one location to another. In the exemplary embodiment of a capillary tube, electrophoresis can be used to move one or more microvessels into, through, or out of the capillary. In embodiments that utilize an examination surface, one or more microvessels can be moved via electrophoresis to or from the examination surface. If desired, one or more microvessels can be electrophoretically transported to a particular location or feature of an examination surface such as a well or groove. In embodiments that utilize electrophoretic transport, the microvessel(s) will typically be made from a material that insulates the reservoir core or dampens electroosmotic force occurring at reservoir core. However, it will be understood that in particular embodiments the material can be selected to allow electrophoretic ejection of substances from the reservoir core.

Figure 29:
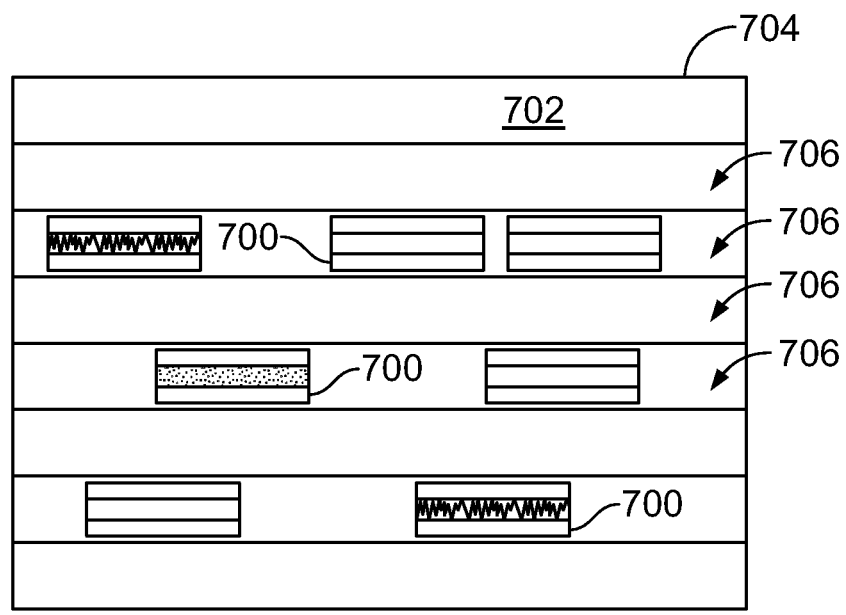
FIG. 29 illustrates a plan view of a plurality of microvessels arranged on an examination surface in accordance with one embodiment.
Figure 30:
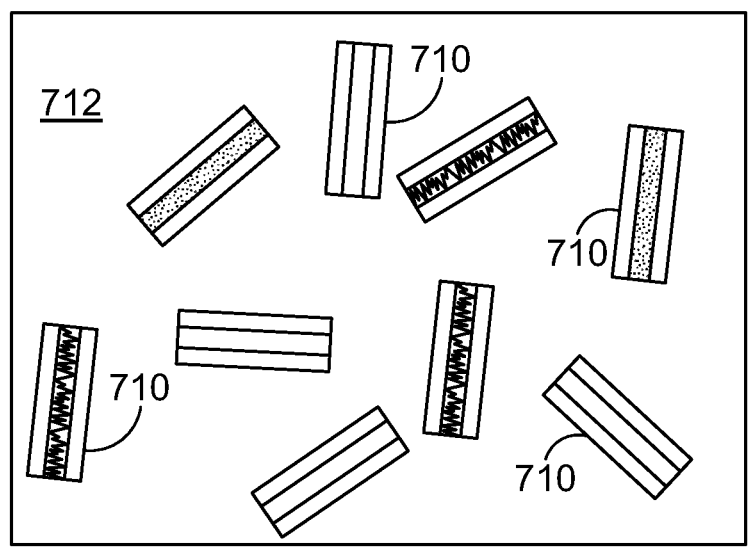
FIG. 30 illustrates a plan view of a plurality of microvessels positioned randomly on an examination surface in accordance with another embodiment.
Figure 31:
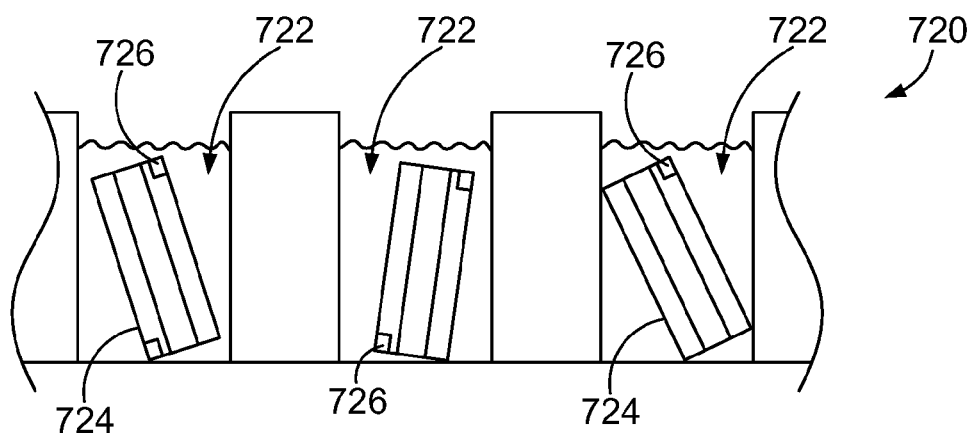
FIG. 31 is a side cross-sectional view of an apparatus having a plurality of isolated microvessels in accordance with one embodiment.

FIGS. 29-31 show other methods or systems for detecting reactions. In FIG. 29, the reactions being detected occur during real-time PCR. The optically detectable characteristics in real-time PCR may be provided, for example, by stem-loop molecular beacons. As shown, a plurality of microvessels 700 are arranged on an examination surface 702 of a container 704. In the exemplary embodiment, the container 704 is a tray having a plurality of grooves 706 formed along the examination surface 702. The microvessels 700 may be randomly located within the grooves 706. Each groove 706 may be sized and shaped with respect to a size and shape of the microvessels 700 to align the microvessels 700 with respect to each other along a common axis.

In real-time PCR, multiple images may be captured of the microvessels 700 throughout a thermal cycle (i.e., multiple amplification cycles). For example, an image of the tray of microvessels 700 may be captured after each amplification cycle to determine a level of an optically detectable property or characteristic (e.g., fluorescence). Alternatively, each microvessel 700 may be scanned as described above to determine the level of the optically detectable characteristic. A level of an optically detectable characteristic may indicate how many copies of amplicons were made during each amplification cycle. Before, during, or after the thermal cycle, the tray of microvessels 700 may be scanned to determine an identifiable code of each microvessel 700. A location of each microvessel 700 may then be determined. The locations of the microvessels 700 may then be correlated with the different levels of fluorescence. Primer pairs corresponding with each microvessel 700 may be identified and correlated with the corresponding level of fluorescence. Accordingly, the imaging system illustrated in FIG. 29 may be characterized as a mapper where positions or locations of randomly located microvessels 700 are determined and correlated with the detected reactions.

FIG. 30 illustrates a plan view of a plurality of microvessels 710 positioned randomly on an examination surface 712 in accordance with another embodiment. In the exemplary embodiment, the examination surface 712 is flat or substantially smooth such that the microvessels 710 may fall randomly onto the examination surface 712 in various orientations. However, as described above, the microbodies and reservoir cores of the microvessels 710 may be sized and shaped such that the reactions are detectable regardless of the rotational orientation of the microvessels 710. An image of the entire examination surface 712 or only a portion of the examination surface 712 may be captured. In some embodiments, only one image is captured and includes both identifiable codes of the microvessels 710 and the detected reactions (e.g., fluorescence). However, in other embodiments, two separate images may be taken and overlaid with respect to each other to correlate the identifiable code with the corresponding detected reaction.

FIG. 31 is a side cross-sectional view of an apparatus 720 having a plurality of compartments or chambers 722 where a plurality of microvessels 724 are isolated from each other. In the exemplary embodiment, the apparatus 720 may be a microplate having a plurality of wells. However, the apparatus 720 may be other containers that include separate compartments. As described above, in some embodiments, the microvessels 724 may function as micropackages configured to deliver a biological or chemical substance to a compartment or well 722 to facilitate performing a reaction therein. As shown, each microvessel 724 is encoded with an identifiable code 726. The identifiable codes 726 may be associated with the substance that the corresponding microvessel 724 is configured to deliver to the corresponding compartment 722.

As shown, each well 722 is sized and shaped such that a volume of the well 722 accommodates no more than a single microvessel 724. The reservoir cores of the microvessels 724 may be in fluid communication with the ambient environment surrounding the microvessels. In some embodiments, when the microvessels 724 are deposited within the corresponding wells 722, each reservoir core of a microvessel 724 may also be in fluid communication with the ambient environment that surrounds the compartment or well 722. For example, the container 720 may be porous such that a common fluid may be directed to flow into each well 722 of the container 720. The fluid may contain other chemicals or biomolecules for performing a reaction. The fluid may flow into the reservoir core of the microvessels 724. The biological or chemical substance carried within the reservoir core may chemically react with the fluid and/or may diffuse out of the reservoir core into the compartment 722. As such, the size and shape of the reservoir cores as well as the surface properties of the interior surfaces may be configured to control the flow of a liquid into the reservoir cores. Furthermore, the dimensions, surface properties, and liquids may also be configured to control a rate of diffusion into or out of the reservoir core.

If the reaction provides a detectable property, the identifiable code 726 of the microvessel 724 may be determined to identify a substance produced, consumed, or delivered within the reservoir core. In such embodiments, the identifiable code 726 may be positioned in the microvessel 724 to be easily detected while in the compartment 722. For example, as shown in FIG. 31, the identifiable codes 726 may be located at ends of the microvessels 724.

Figure 32:
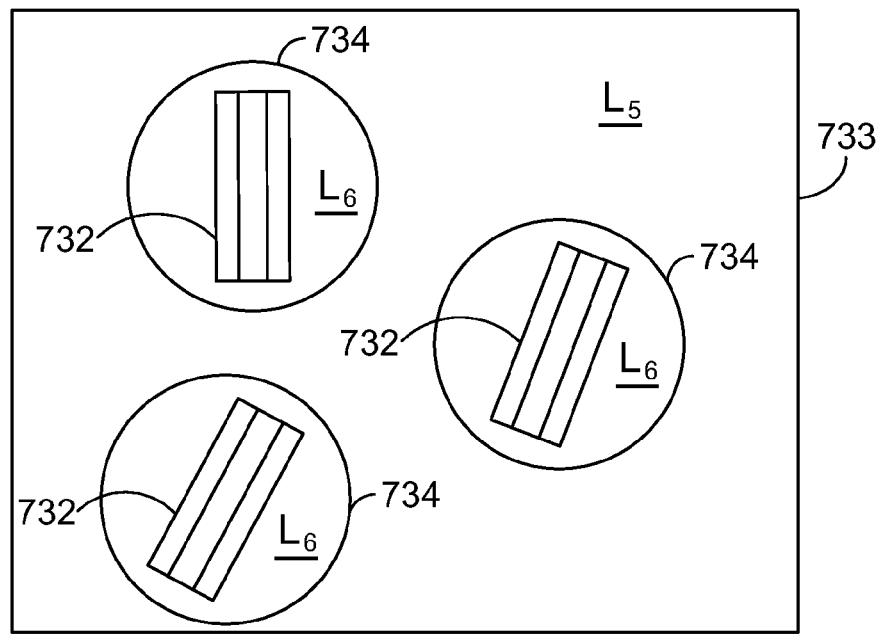
FIG. 32 is a side view of a plurality of isolated microvessels in a common liquid in accordance with one embodiment.

FIG. 32 is a side view of a plurality of isolated microvessels 732 in separate compartments within a common liquid $L_5$. More specifically, microvessels 732 may be added to a mixture of an aqueous solution $L_6$ and a non-polar liquid $L_5$ (e.g., water-in-oil emulsion). The exterior surfaces of the microvessels 732 may be substantially hydrophilic. When the microvessels 732 are mixed within the mixture, the microvessels 732 may attract the aqueous solution. The cohesive and adhesive forces generated by surface properties of the aqueous solution $L_6$, non-polar liquid $L_5$, and the exterior surfaces of the microvessels 732 may form micelles 734. In some embodiments, a density of the microvessels, a total volume of aqueous solution, and the surface properties of the microvessels 732 and the aqueous solution $L_6$ may be configured so that generally only one microvessel 732 is contained within a micelle. However, embodiments may include more than one microvessel 732 in the micelles. Optionally, the microvessels 732 may include an identifiable code as described above.

As shown in FIG. 32, each microvessel 732 is in a micelle 734 and the micelles 734 are in a container 733. As such each microvessel 732 is within an ambient environment of liquid $L_6$ and each micelle 734 in turn is within an ambient environment of liquid $L_5$. As such, the reservoir core of each of the microvessels 732 is in fluid communication with the ambient environment that surrounds the microbody of the microvessel 732. In other words, the reservoir core may be in fluid communication with the aqueous solution $L_6$. In this case, the plurality of compartments that hold the microvessels 732 are the micelles 734.

Figure 33:
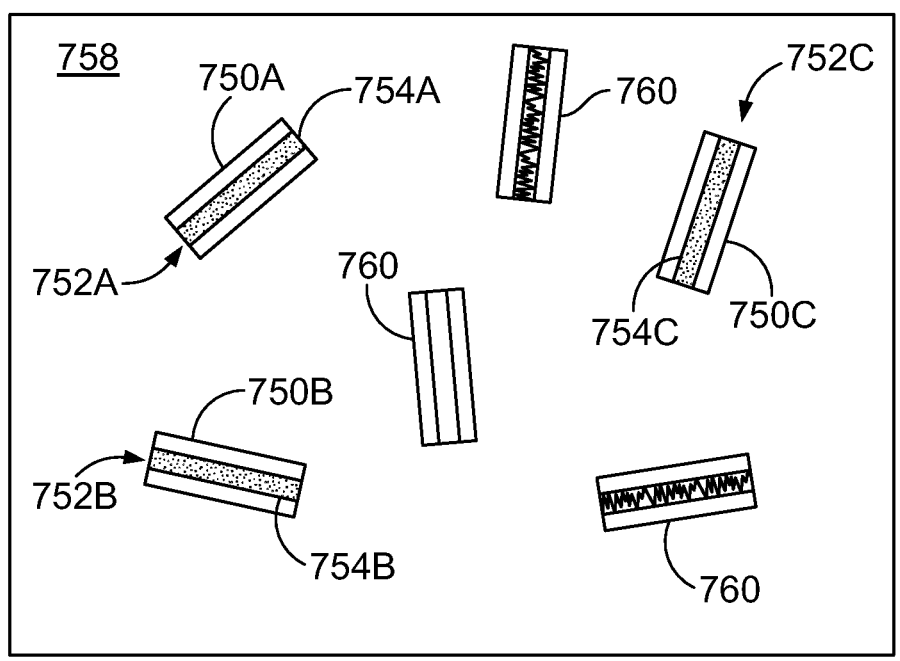
FIG. 33 illustrates a plan view of an examination surface having a plurality of reference microvessels thereon in accordance with an alternative embodiment.

FIG. 33 illustrates a plan view of an examination surface 758 having a plurality of reference microvessels 750 thereon in accordance with an alternative embodiment. As shown, the microvessels 750 are not encoded, but alternative embodiments may include identifiable codes. Embodiments described herein may also be used as references or standards for calibrating an imaging system. For example, the reference microvessels 750A-750C may be used is calibrating fluorescent detectors. In such embodiments, reservoir cores 752A-752C of the reference microvessels 750A-750C may have respective known compositions 754A-754C deposited into the reservoir cores 752A-752C. Each composition 754A-754C may emit a predetermined emission signal (e.g., 670 or 570 nm wavelengths) when excited by an optical excitation beam.

When detected or imaged, the reference microvessels 750A-750C may produce a predetermined set of optical signals thereby forming a reference standard. As such, the reference microvessels 750A-750C may provide references or standards for determining a level or quality of emissions from other microvessels 760 that are loaded with samples of interest. For example, different microvessels in a set can have different predefined concentrations of an optically detectable substance. Alternatively or additionally, different microvessels can have different analytes with different detectable characteristics such as fluorophores with different excitation or emission wavelengths. Optionally the microvessels can have codes that are correlated with the type and/or amount of substance in the respective reservoir core.

In alternative embodiments, the reference microvessels 750 may include identifiable codes as described above. The identifiable code of each reference microvessel may be associated or correlated with a predefined concentration of a substance held within the reservoir core of the reference microvessel.

In some embodiments, the reference microvessels 750 may have annuluses that surround corresponding reservoir cores 752. Each annulus may be doped (e.g., with rare earth dopant, Chromium, CdTe, CdSe/ZnS, or PbSe complexes) so that the material of the annuluses fluoresce at a desired wavelength.

In addition to the above described embodiments, the microvessels and accompanying methods, assays, systems, and apparatuses described herein may be similar to the microparticles and accompanying methods, assays, systems, and apparatuses described in U.S. patent application Ser. No. 10/661,234 (filed Sep. 12, 2003); Ser. No. 10/645,686 (Aug. 20, 2003); Ser. No. 10/645,689 (Aug. 20, 2003); Ser. No. 10/661,031 (Sep. 12, 2003); Ser. No. 10/661,082 (Sep. 12, 2003); Ser. No. 10/661,115 (Sep. 12, 2003); Ser. No. 10/661,116 (Sep. 12, 2003); Ser. No. 10/661,234 (Sep. 12, 2003); Ser. No. 10/661,254 (Sep. 12, 2003); Ser. No. 10/661,836 (Sep. 12, 2003); Ser. No. 10/763,995 (Jan. 22, 2004); Ser. No. 10/956,791 (Oct. 1, 2004); Ser. No. 10/990,057 (Nov. 15, 2004); Ser. No. 11/063,660 (Feb. 22, 2005); Ser. No. 11/063,665 (Feb. 22, 2005); Ser. No. 11/063,666 (Feb. 22, 2005); Ser. No. 11/158,782 (Jun. 21, 2005); Ser. No. 11/187,262 (Jul. 21, 2005); Ser. No. 11/206,987 (Aug. 18, 2005); Ser. No. 11/226,892 (Sep. 13, 2005); Ser. No. 11/226,914 (Sep. 13, 2005; Ser. No. 11/281,907 (Nov. 16, 2005); Ser. No. 11/281,910 (Nov. 16, 2005); Ser. No. 11/281,937 (Nov. 16, 2005); Ser. No. 11/283,517 (Nov. 17, 2005); Ser. No. 11/283,518 (Nov. 17, 2005); Ser. No. 11/454,307 (Jun. 16, 2006); Ser. No. 11/544,309 (Oct. 6, 2006); Ser. No. 11/546,027 (Oct. 10, 2006); Ser. No. 11/601,584 (Nov. 16, 2006); Ser. No. 11/607,837 (Nov. 30, 2006); Ser. No. 11/784,798 (Apr. 10, 2007); Ser. No. 12/053,242 (Mar. 21, 2008); Ser. No. 12/144,209 (Jun. 23, 2008); Ser. No. 12/174,490 (Jul. 16, 2008); Ser. No. 12/235,834 (Sep. 23, 2008), each of which is incorporated by reference in its entirety.

FIG. 34 illustrates a perspective view of a microvessel 800 formed in accordance with an alternative embodiment. As shown, the microvessel 800 has a microbody 802 and a plurality of reservoir cores 804 extending therein along an axial direction. The microvessel 800 also includes an identifiable code 806 that may extend in the axial direction parallel to the reservoir cores 804. The reservoir cores 804 may be separate from each other (i.e., not in direct fluid communication). The identifiable code 806 may comprise a series of axially aligned segments that are separated from each other by gaps such that a transparent material extends through the microbody 802 between the segments. The identifiable code 806 may be binary or non-binary. The segments and gaps may be composed of materials that exhibit different transmissivity (in an optical transmittance mode) or reflectivity (in an optical reflectance mode) to the specific light used in imaging the microvessels 800. In some embodiments, the identifiable code 806 may be identified by locations of the gaps between the segments. The segments may comprise silicon and the transparent material may be glass.

The embodiment illustrated in FIG. 34 may be fabricated using a similar technology that is used for integrated circuits (e.g. interconnects) or MEMS. For example, U.S. Pat. No. 7,745,091, which is incorporated by reference in the entirety, describes fabricating encoded particles without reservoir cores. However, reservoir cores may be formed using similar methods described herein. For instance, after the axially aligned opaque segments are fabricated, a transmissive layer (e.g., glass) may be deposited over the opaque segments. The transmissive layer may be applied in one step or a plurality of transmissive layers. If a plurality of transmissive layers is applied, the different layers may have different dopant levels that are suitable for the differential etching process described herein. As shown in FIG. 34, the identifiable code 806 may separate two elongated transmissive portions. A region in each of these elongated portions may then be removed.

FIG. 35 illustrates a plan view of a microvessel 810 formed in accordance with another embodiment. The microvessel 810 may have a microbody 812 that includes a reservoir core 814 extending therethrough in an axial direction. The microbody 812 may also include spatially-defined machine-readable codes 816 that extend in the axial direction parallel to the reservoir core 814. The identifiable code 816 may be formed from morphological markings 818 (e.g., pits, grooves, notches, teeth, or bumps) on a surface of the microbody 812 that change the morphology of the microvessel 810. The morphological markings 818 may be located according to a predetermined coding system. For example, FIG. 35 shows eighteen (18) morphological markings 818. The coding system may be a binary system that includes the presence or absence of any one of the morphological markings 818.

FIGS. 36(a)-(d) illustrate cross-sectional views of microvessels 831-834, respectively. As shown, each microvessel 831-834 may include a microbody 841-844 having a reservoir core 851-854, respectively, that extends into the corresponding microbody. As shown in FIGS. 36(a) and 36(b), the reservoir cores 851 and 852 may have different cross-sectional shapes. In both FIGS. 36(a) and 36(b), the microbodies 841 and 842 may have identifiable codes 861 and 862, respectively, distributed about the corresponding reservoir cores. The identifiable codes 861 and 862 may be located so that the identifiable codes 861 and 862 do not interfere or affect light energy emitted from the corresponding reservoir cores 851 and 852. Furthermore, the identifiable codes 861 and 862 may be located along a surface of the corresponding microbody so that incident light may be immediately reflected and/or refracted to determine the identifiable code.

In FIG. 36(c), a shape of the interior surface of the reservoir core 853 may be configured to increase an intensity of radiation onto a sample of interest (not shown) within the reservoir core 853. In FIG. 36(d), the microbody 844 may have a cross-sectional shape other than a square or circular cross-section.

Figure 37:
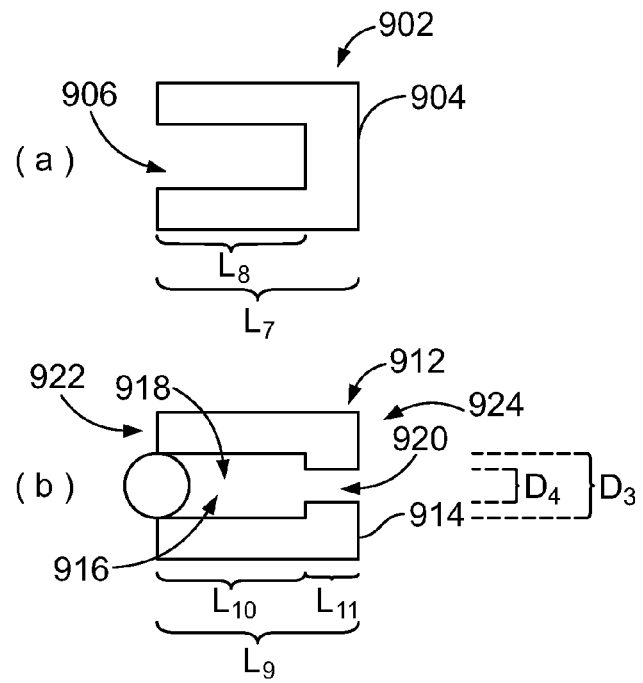
FIG. 37 illustrates side cross-sectional views of microvessels formed in accordance with other embodiments.

FIG. 37 illustrates side cross-sectional views of microvessels 902 and 912 that may be formed in accordance with alternative embodiments. As shown in FIG. 37(a), the microvessel 902 has a microbody 904 and a reservoir core 906 extending into the microbody 904. The microbody 904 has a length $L_7$, and the reservoir core 906 extends a depth or length $L_8$ into the microbody 904 from one end of the microbody 904. As shown, the length $L_7$ may be greater than the length $L_8$. Optionally, the microvessel 902 may be encoded and have surfaces selectively modified as described above.

As shown in FIG. 37(b), the microvessel 912 has a microbody 914 and a reservoir core 916 extending into the microbody 914. The microbody 914 has a length $L_9$. The reservoir core 916 has first and second sections 918 and 920. The first section 918 extends a depth or length $L_{10}$ from an end 922 toward an opposite end 924. The second section 920 extends a depth or length $L_{11}$ from the end 924 toward the opposite end 922. The first section 918 may have a diameter $D_3$ and the second section 920 may have a smaller diameter $D_4$. Accordingly, the reservoir core 916 may be in fluidic communication with the ambient environment at both ends 922 and 924 of the microvessel 912. However, dimensions of the reservoir core 916 may be varied. For example, liquid may enter the reservoir core 916 more easily through the end 922 than the end 924. As one example, the second section 920 may be configured to allow gas or fluid to exit the reservoir core 916 when the liquid enters the reservoir core 916 at the end 922.

Also shown in FIG. 37(b), in some embodiments, the microvessel 912 may include a reservoir cap or stopper 926. The cap 926 may prevent unwanted fluid from entering the reservoir core 916 and/or prevent fluid from exiting the reservoir core 916. As shown, the cap 926 may be a polymer bead. The cap 926 may form an interference fit with the reservoir core 916 at the end 922.

Figure 38:
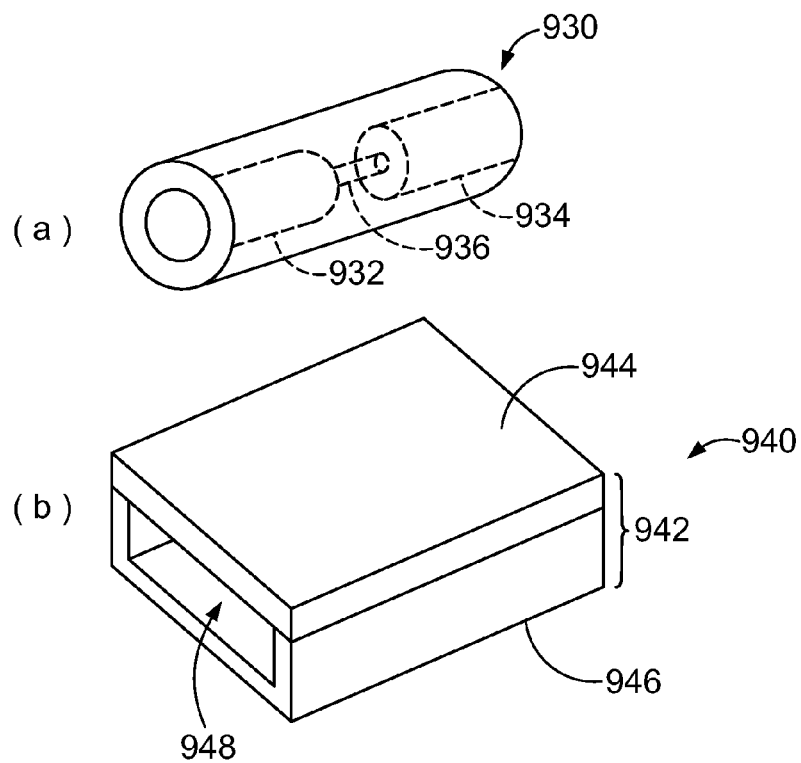
FIG. 38 illustrates perspective views of microvessels formed in accordance with other embodiments.

FIG. 38 illustrates perspective views of microvessels 930 and 940 formed in accordance with alternative embodiments. As shown in FIG. 38(a), the microvessel 930 may include two reservoir cores 932 and 934 that are fluidicly coupled to one another through a passage or channel 936. The passage 936 may be sized and shaped to control diffusion of a first liquid held within the reservoir core 932 into a second liquid held within the reservoir core 934. As shown in FIG. 38(b), the microvessel 940 may include a microbody 942 having a reservoir core 948 extending therethrough. The microbody includes a first portion 944 that comprises a transparent first material and a second portion 946 that comprises a different second material. The second material may not be as transparent as the first material. As such, the microbody 942 may be a composite that comprises two different materials.

Figure 39:
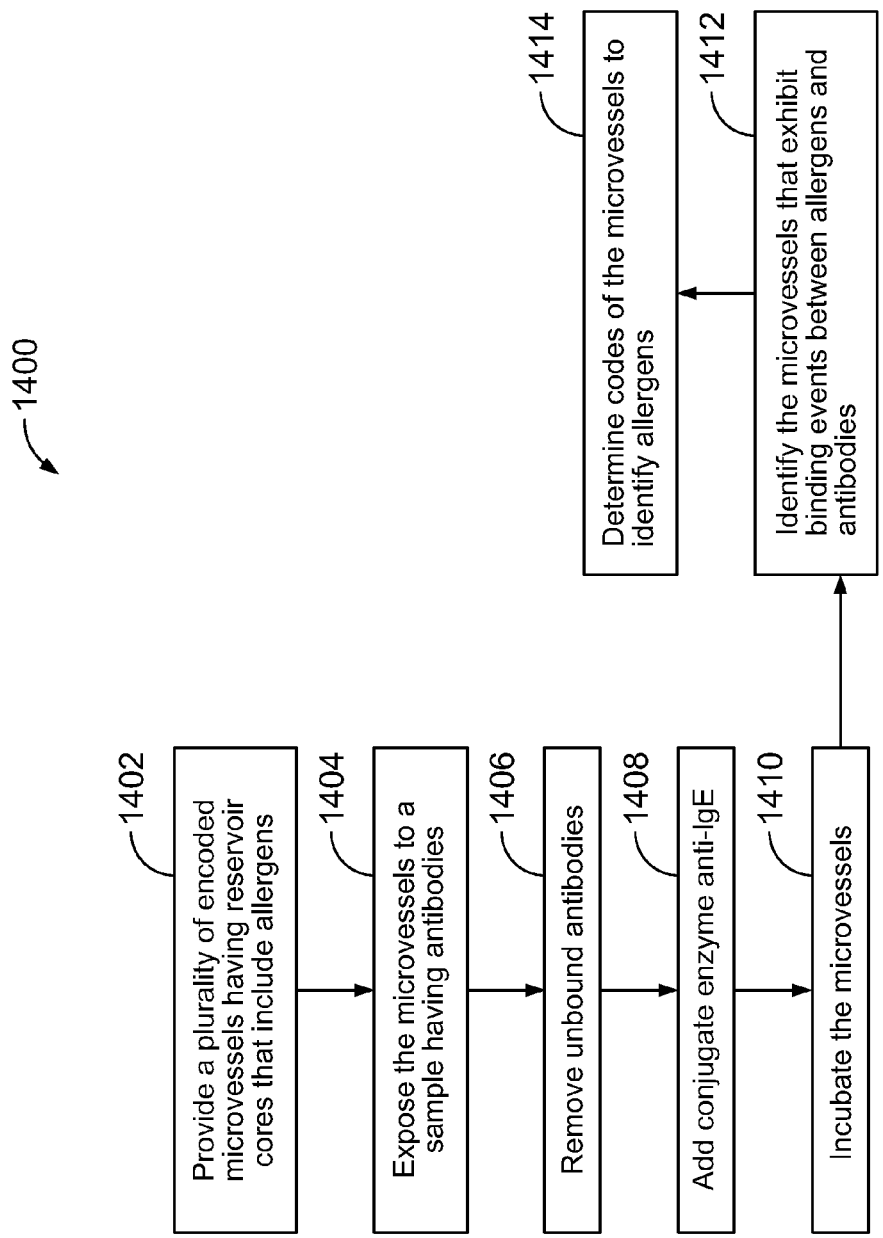
FIG. 39 is a block diagram illustrating a method of conducting an immunoassay.

FIG. 39 illustrates a method 1400 of conducting an immunoassay. The method 1400 is described with specific reference to identifying an individual's sensitivity to allergens-of-interest. However, the method 1400 may be used in other immunoassay protocols to determine, for example, whether an antigen or antibody exists within a sample. The method 1400 includes, at 1402, providing a plurality of encoded microvessels having microbodies and reservoir cores therein. The reservoir cores may hold an antigen or allergen therein. In the exemplary embodiment, each of the microvessels have an identifiable code that is associated with the allergen within the corresponding reservoir core. In alternative embodiments, the microvessels are not individually identifiable but are located at known positions in an array of microvessels.

The reservoir cores may contain a solid-phase substance or material that has an antibody or antigen immobilized thereon. In the illustrated embodiment, the solid-phase material has an allergen immobilized thereto. The reservoir core may extend only partially through the microbody and the solid-phase material may be located a depth therein. Various solid phase substances may be used including, but not limited to, CPGs, activated cellulose, gels, porous matrices, foams, microparticles or beads, and the like. The solid-phase material may also be a cellulose polymer including a CNBr-activated cellulose derivative that has allergens covalently coupled thereto. In particular embodiments, non-competitive binding of the antibodies may be desired. As such, the solid-phase material may be configured to provide a sufficiently large surface area so that a number of allergens in the reservoir core significantly exceeds a number of antibodies in a sample.

At 1404, the microvessels are exposed to a sample. For example, an individual's plasma or serum may be added to a container that is holding the microvessels. The sample may include antibodies as exemplified in FIG. 39. However, it will be understood that the microvessel reservoir core can alternatively hold antibody(ies) and the sample can include allergens or other target molecules that will be bound to the antibodies.

In embodiments where the microvessels are individually identifiable, the microvessels may be mixed within the sample. Returning to the exemplary configuration of FIG. 39, when exposed to the sample, antibodies in the sample and allergens attached to the solid-phase material may selectively bind to each other. More specifically, in allergy testing embodiments, IgE antibodies within the sample may selectively bind to the allergens-of-interest in the reservoir cores of the different microvessels. At 1406, the unbound IgE antibodies may be removed or washed away from the solid-phase material. At 1408, enzyme labeled antibodies against IgE (or conjugate enzyme anti-IgE) may be added to the container. The microvessels may then be exposed to a thermal cycle. After incubation, at 1410, the unbound enzyme-anti-IgE may be washed away and the microvessels may then be incubated with a developing agent, such as a fluorogenic agent.

The microvessels may then be examined. For example, the method 1400 may include, at 1412, identifying the microvessels that exhibit detectable characteristics of a binding event between the antibodies and allergens. The microvessels may be identified, for example, by scanning a plate or holder having the microvessels thereon to detect fluorescence emanating from the microvessels. Before, after, or during the identifying operation, the identifiable codes of the microvessels may be determined, at 1414. After identifying the microvessels, the results of the examination may then be analyzed to identify the particular allergens that an individual is sensitive to.

In alternative embodiments, the microvessels described herein may be used in an enzyme-linked immunosorbent assay (ELISA) protocol. In such embodiments, the microvessels may hold different substances in the reservoir core and on the exterior surface of the microbody. For example, encoded microvessels may be prepared that include a specific monoclonal antibody that selectively binds with a complementary antigen. The monoclonal antibody may be immobilized to the exterior surface of the microvessel. The microvessel may have an identifiable code, as described herein, that is associated with the monoclonal antibody. In addition to the monoclonal antibodies, the microvessel may also include modified reporter antibodies within the reservoir core. The modified reporter antibodies are configured to selectively bind with a complex that includes the monoclonal antibodies and the complementary antigens. Accordingly, a set of microvessels may exist in which microvessels with different codes have different monoclonal antibodies.

To conduct the assay, the set of encoded microvessels may be exposed to a serum including antigens. If complementary antigens exist in the serum, the antigens may selectively bind to the complementary monoclonal antibodies. The set of microvessels may then be washed to remove the serum and excess antigens. The microvessels may then be individually positioned within recesses or wells of a microplate that are sized to accommodate only a single microvessel. A common liquid may then be directed into the wells, the liquid being configured to release the reporter antibodies within the reservoir cores. In such embodiments, the microvessels may be effectively isolated from other microvessels within their corresponding wells. The microplate may be vibrated to facilitate mixing the reporter antibodies with the monoclonal antibodies/antigen complex. The microvessels may then be removed and added to a solution that includes a fluorescent label that selectively binds to the reporter antibodies. At this time, the microvessels having monoclonal antibodies that positively reacted with a complementary antigen should fluoresce. The microparticles may be, for example, aligned along a grooved plate to identify those microparticles that fluoresce and determine the identification code of said microparticles.

FIGS. 40-45 illustrate a method 1500 of producing an array having biomolecules at known locations or reaction sites. Various microparticles, such as those described herein, and others known in the art may be used. Generally, the microparticles used in the method 1500 provide solid supports that are configured to transport biological or chemical substances. As such, the microparticles used in the method 1500 may be function as microcarriers. For example, in some embodiments, the microparticles used in the method 1500 may be similar to the various microvessels having reservoir cores described herein. In other embodiments, the microparticles may comprise solid masses (i.e., without reservoir cores). In such microparticles, biological or chemical substances (e.g., biomolecules) may be immobilized to an exterior surface of the microparticle.

The microparticles used in the method 1500 may be individually identifiable based on a coding system. The codes may be separate features that are immobilized to the microbeads (e.g., tags), or the codes may be formed with the microbead. In exemplary embodiments, the microparticles comprise an optical substrate having a variation in at least one of a refractive index and optical absorption. Such optical substrates may or may not include reservoir cores as described herein. For instance, gratings disposed within the microparticles may constitute codes of the microparticles. The gratings may include a superposition of different predetermined periodic variations of an index of refraction disposed in the optical substrate along an axis. Exemplary microparticles are described in greater detail in U.S. patent application Ser. Nos. 10/661,234; 10/661,031; 10/661,082; 10/661,115; 10/661,116; 10/661,234; 10/661,254; and 10/661,836, which are each incorporated by reference in the entirety. The microbeads described in U.S. Pat. No. 7,745,091, which is incorporated by reference in the entirety, may also be used in the method 1500. Furthermore, other coding systems may be used, such as morphological markings on the microparticle or sequence tags that are immobilized to a surface of the microparticle.

Figure 40:
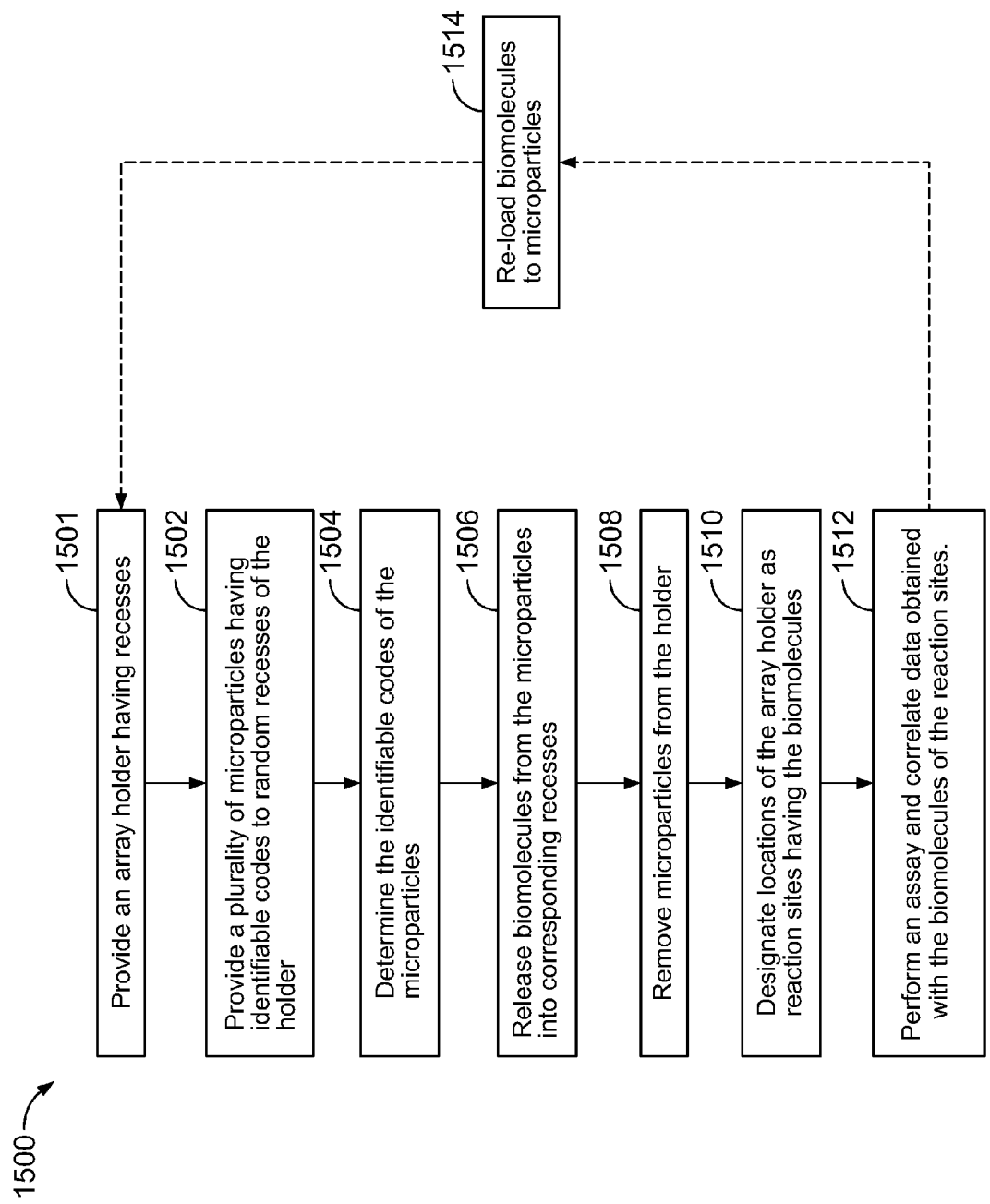
FIG. 40 is a block diagram illustrating a method of preparing an array.
Figure 41:
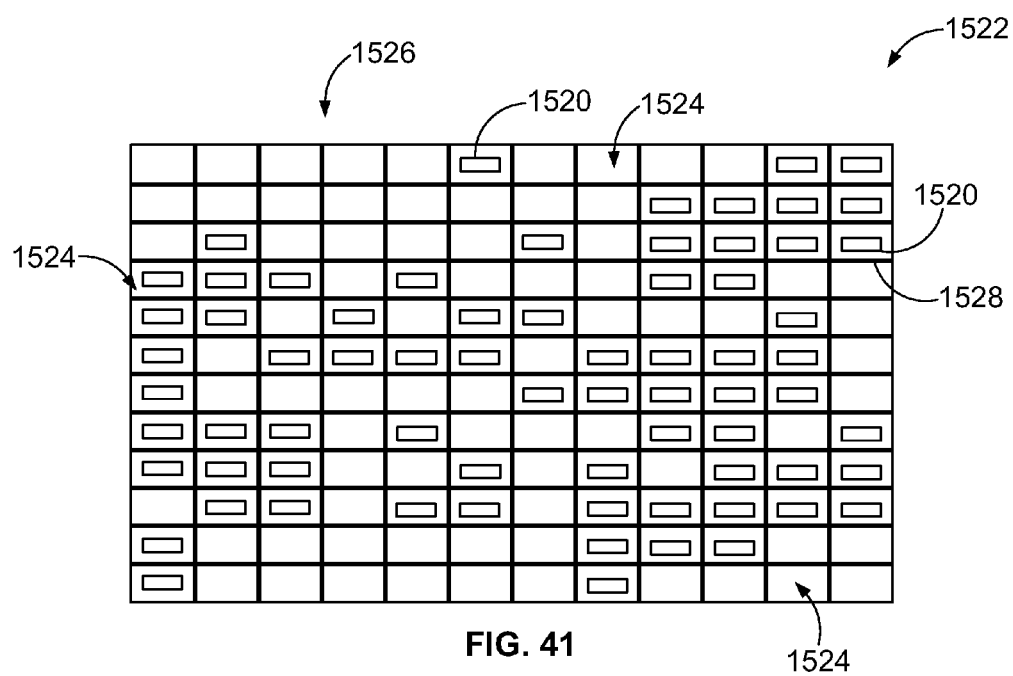
FIG. 41 is a plan view of an array holder that may be used in accordance with various embodiments.

FIGS. 41-45 may be referenced with respect to the method 1500 of FIG. 40. The method 1500 includes providing, at 1501, an array holder 1522. The holder 1522 may form an array having a plurality of recesses 1524 that are generally disposed in a coplanar manner. FIG. 41 is a plan view of the holder 1522 and illustrates at least one active side or surface 1526. The active side 1526 is generally planar and includes the recesses 1524 thereon. The recesses 1524 may have recess locations that spatially ordered (e.g., in rows and columns as shown in FIG. 41) or the recess locations may be more random due to, for example, how the array holder is manufactured.

As shown in FIG. 41, the recesses 1524 are accessible along the active side 1526 and may be configured to receive the microparticles 1520. In some embodiments, the recesses 1524 may be wells, pits, cavities, and the like. In alternative embodiments, the recesses 1524 may be grooves or channels. Furthermore, the recesses 1524 may define compartments or chambers that are greater in size than the microparticles such that adjacent microparticles are separated by sidewalls therebetween. Alternatively, the recesses 1524 may not be larger than the microparticles 1520 therein. For example, the recesses 1524 may be defined by small ridges that are used to align the microparticles 1520.

In some embodiments, the holder 1522 may be an assembly that includes separate parts or components. For example, the holder 1522 may include a planar substrate (e.g., chip or slide) and a gasket that is mounted onto the planar substrate. The planar substrate may form the bottoms of the recesses 1524 and the gasket may have a plurality of openings therethrough that define sidewalls of the recesses 1524. In other embodiments, the holder 1522 may also be a substantially single structure. For example, the holder 1522 may be a solid plate that is fabricated (e.g., through machining, molding, lithography, and the like) to include the recesses 1524. Exemplary holders and exemplary methods for manufacturing and using such holders are described in greater detail in U.S. Pat. Nos. 7,164,533 and 7,399,643, each of which is incorporated by reference in the entirety. The holders, methods of manufacturing, and methods of use described in the '533 and '643 patents may similarly be applied to embodiments with recesses as described herein. As another example, the holder 1522 may be a fiber-optic bundle where the fiber ends are etched to form the recesses 1524. The holder 1522 may also be a silicon wafer in which the recesses 1524 are formed by deposited photoresist and plasma-etched surfaces.

Although not shown, the holder 1522 may be one component in a larger assembly or system. For example, the holder 1522 may be operatively connected to a fluidic circuit that provides the microparticles 1520 to the holder 1522. Furthermore, the holder 1522 may be configured to hold the microparticles 1520 while an assay is performed and when the microparticles are examined. In some cases, the holder 1522 may be transported from one station for performing an assay to another station for examining the microparticles 1520. In other cases, the holder 1522 may remain at substantially one location for both processes.

In some embodiments, surfaces along the active side 1526 may be modified for subsequent reactions. For instance, surfaces within the recesses 1524 may have functional groups immobilized thereto. By way of example, the surfaces within the recesses 1524 may be covalently coated with alkyne or azide containing moiety to perform "click chemistry" (e.g., copper catalyzed azide-alkyne cycloaddition). Some examples of using click chemistry with nucleic acids and other biomolecules are described in El-Sagheerab et al. "Click Chemistry with DNA," Chem. Soc. Rev., 2010, 39, 1388-1405 and also in Binder et al., "'Click' Chemistry in Polymer and Material Science: An Update," Macromol. Rapid Commun. 2008, 29, 952-981, each of which is incorporated by reference in the entirety. Those skilled in the art understand that other targeting chemistries may be used with embodiments described herein. Exemplary chemistries include, but are not limited to those used to crosslink biomolecules and attach biomolecules to solid supports, many of which are commercially available from sources such as Sigma Aldrich (St. Louis, Mo.) or Thermo Scientific (Rockford, Ill.). Other examples for immobilizing oligonucleotides or other biomolecules to surfaces include using triazine-hydrazine with aldehyde-functionalized oligos, such as those described in U.S. Pat. No. 7,259,258, which is incorporated by reference in the entirety; triazine chloride with amine-functionalized oligos; carboxylic acid with amine-functionalized oligos using a coupling reagent, such as EDC, or coupling reagents known to those skilled in the art, thiol with thiol-functionalized oligos; alkene surfaces with dialkene-functionalized oligos that are coupled through Diels-Alder reactions; and acetyl bromide surfaces with thiophosphate-functionalized oligos, such as those described in WO 2005/065814, which is incorporated by reference in the entirety. Glass-like surfaces can also be modified with various glass-reactive molecules, such as functionalized silanes, some of which are commercially available through Gelest, Inc. Oligos with terminal C6 amines or other functionalities may be used, such as those produced by Glen Research, Inc. Accordingly, surfaces of the holder 1522 may be modified in various manners and for various purposes. In addition to embodiment(s) described with respect to the method of FIG. 40, the above-described surface chemistries may also be used with other embodiments described herein.

Figure 45:
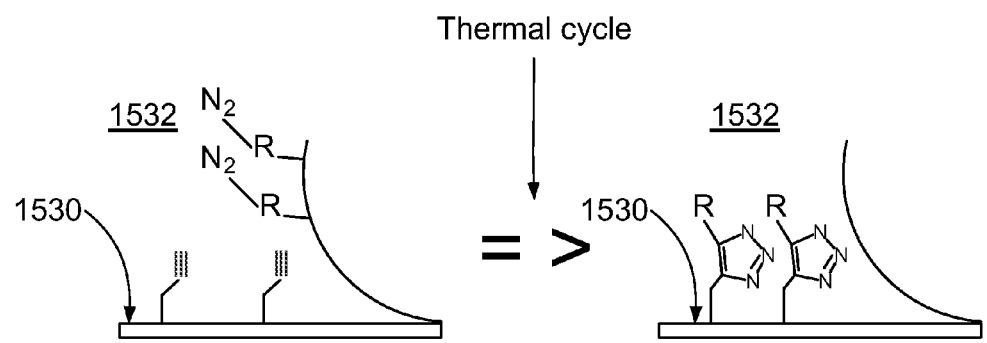
FIG. 45 illustrates one example of click chemistry that may be used to transfer biomolecules on the microparticles to a support surface in the recesses.

The method 1500 also includes providing, at 1502, a plurality of microparticles 1520 to the array holder 1522. The microparticles 1520 may include a code that is uniquely associated with a biological or chemical substance that is carried by the corresponding microparticle 1520. In particular embodiments, the biological or chemical substance comprises nucleic acid sequences (e.g., oligonucleotides, primers) that have been modified to include functional groups (e.g., acetylene moiety, azide) at a terminal end. The sequences may be immobilized to an exterior surface of the microparticles 1520 (as shown in FIG. 45).

When the microparticles 1520 are provided at 1502, the microparticles 1520 may be dispensed onto the active side 1526 in a random manner such that the microparticles 1520 fall into the random recesses 1524. For example, the microparticles 1520 may be delivered through a microfluidic circuit (not shown) onto the active side 1526 or may be dispensed manually by an individual using, e.g., a pipette. When the microparticles 1520 are provided to the active side 1526, the microparticles 1520 may fall directly into the recesses 1524 into a desired orientation or the microparticles 1520 may at least partially rest on sidewalls 1528 that define the recesses 1524. Optionally, the holder 1522 may be tilted or shaken (e.g., through vibration) to facilitate self-assembly of the microparticles 1520 into the recesses 1524.

Figure 42:
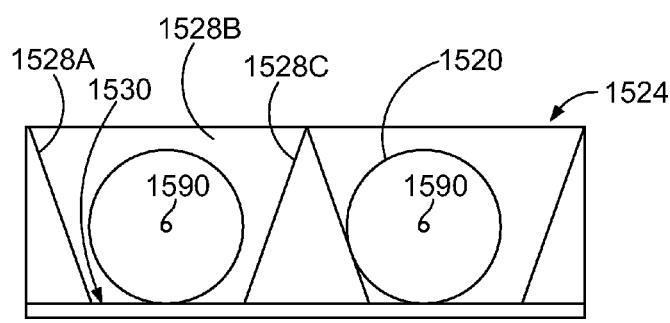
FIG. 42 is a side view of microparticles located in recesses of the holder in FIG. 41.
Figure 43:
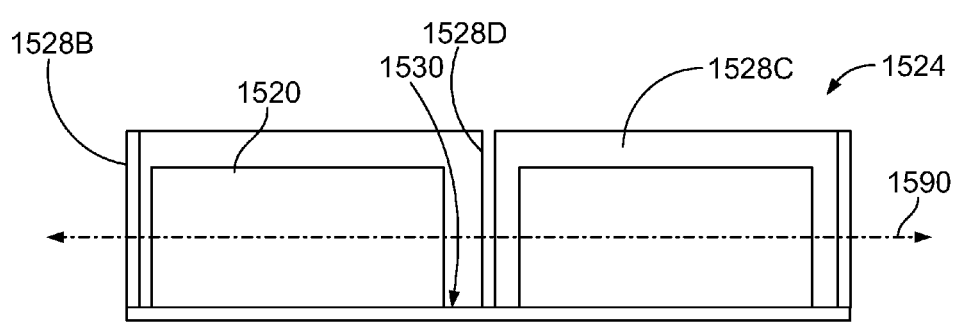
FIG. 43 is a different side view of the microparticles that are located in the recesses.

FIGS. 42 and 43 illustrate different side views of exemplary recesses 1524. In the illustrated embodiment, the recesses 1524 are defined by sidewalls 1528A-1528D and a bottom support surface 1530. Each of the recesses 1524 may be sized relative to the microparticles 1520 so that each recess 1524 may accommodate only a single microparticle 1520. However, in some cases, it may be desirable to permit a plurality of microparticles 1520 within each of the recesses 1524 and, as such, the recesses 1524 may be sized accordingly. Furthermore, the sidewalls 1528A-1528D may be sized and shaped to facilitate positioning the microparticle 1520 in a desired orientation. The orientation of the microparticle 1520 may facilitate reading the code and/or a detectable characteristic from the microparticle 1520 or from the recess 1524. The orientation may also facilitate introducing a load of the biological or chemical substance to conduct a desired reaction or event. As shown in FIG. 42, the sidewalls 1528A and 1528C are angled with respect to the support surface 1530. When the microparticle 1520 is positioned within the recess 1524, a longitudinal axis 1590 may extend substantially parallel to or substantially align with other microparticles 1520 in other recesses 1524. As such, the holder 1522 and the recesses 1524 may be configured to hold the microparticles 1520 in fixed positions and in a substantially common orientation with respect to a device that detects the code.

The method 1500 also includes determining, at 1504, the identifiable code of the microparticles 1520. The determining operation may be performed in a similar manner as described above with respect to FIG. 28. For example, an input light may be incident upon each microparticle 1520 at a similar angle. When illuminated, the identifiable code of the corresponding microparticle 1520 may reflect, refract, or filter the input light to provide an output light. The output light may have a pattern that is indicative of the code of the corresponding microparticle 1520. In other embodiments, the entire holder 1522 or only portions of the holder 1522 may be imaged with the microparticles 1520 within the recesses 1524. The images may then be analyzed to determine the identifiable codes and which recesses 1524 the microparticles 1520 were located.

Although the determining operation 1504 is described as being performed after placing the microparticles 1520 into the recesses 1524 but before conducting any reactions for analysis, the determining operation 1504 may be performed at various times. For example, the identifiable codes of the microparticles 1520 may be determined after, for example, fluorescence detection if the microparticles 1520 remain in the recesses 1524 while the desired assay is performed.

In particular embodiments, the method 1500 also includes, at 1506, releasing the biomolecules carried by the microparticles 1520 into the corresponding recesses 1524. The releasing operation may include manipulating or controlling environmental conditions of the microparticles 1520 in the recesses 1524. For example, the releasing operation may include, but is not limited to, changing a temperature or pressure of the ambient environment, adding a solution or other matter to the recesses, physically disturbing the microparticles (e.g., by vibration) in the recesses, and applying a magnetic field. In particular embodiments, the releasing operation may include providing a common solution 1532 to the recesses 1524 that facilitates releasing the biomolecules. In the exemplary embodiment, the solution 1532 is a catalyst solution that includes Cu for performing click chemistry as known by those skilled in the art. However, other solutions 1532 may be provided. For example, the solution 1532 may include other components for performing a desired reaction.

Figure 44:
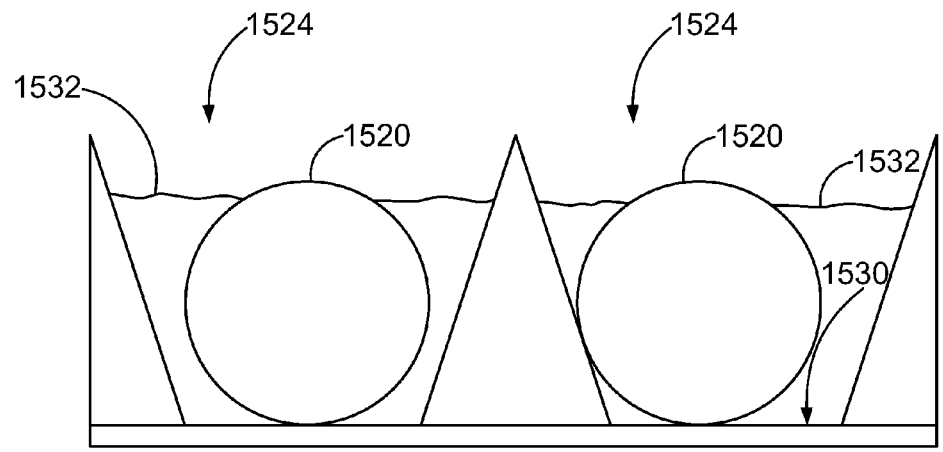
FIG. 44 illustrates the recesses being fluidicly isolated from each other.

When the solution 1532 is provided, the holder 1522 may be completely submerged such that the solution 1532 in each recess 1524 is effectively in liquid communication with the solution 1532 of other recesses 1524. If desired, liquid communication may be broken so that the reaction components in each recess 1524 (e.g., the microparticle 1520 and any substances immobilized thereto, the solution 1532, and the functional groups immobilized to the support surface 1530) are effectively isolated from each other. Isolation of the recesses 1524 may be accomplished by evaporation of the solution 1532, application of an oil film, or pressing a membrane onto the holder 1522 to absorb a portion of the solution 1532. As shown in FIG. 44, the recesses 1524 are effectively isolated from each other.

When the reaction components are provided to the recesses 1524, conditions of the holder 1522 may be controlled or manipulated to transfer the biomolecules. For example, as shown in FIG. 45, the holder 1522 may subject to a thermal cycle so that DNA on the microparticles 1520 dehybridize. The released nucleic acids having the functional group at a terminal end may react with the functional groups immobilized to the support surface 1530 through click chemistry. For example, an acetylene moiety on the nucleic acid may form a stable triazole linkage. Optionally, an azide solution may be used as a scavenger of alkyne to lower crosstalk. Accordingly, the microparticles 1520 may be exposed to certain conditions that release the biomolecules that the microparticle is carrying and immobilize the biomolecules to the support surface 1530.

Optionally, the method 1500 may also include removing, at 1508, the microparticles 1520 after the microparticles 1520 have released or delivered the substances to the recesses 1524. The release can also be timed to occur after codes of the particles have been read, such that the identity of the particular material released at a particular recess or other location can be determined based on a known association of a particular code with a particular material. By way of example, the microparticles 1520 may be removed by inverted centrifugation or by washing the microparticles 1520 from the recesses 1524. If the microparticles 1520 have inherent magnetic qualities, the microparticles 1520 may also be removed through controlled magnetics. In those embodiments that use the solution 1532, the solution 1532 may also be removed (i.e., through washing or centrifugation) before performing an assay.

The method may also include, at 1510, designating the recesses 1524 as reaction sites that include the transferred biomolecules from the corresponding microparticles 1520. A reaction site may represent a region or an area along the active side 1526 of the holder 1522 where desired reactions will occur with biomolecules located at the reaction site. More specifically, each recess 1524 that had a corresponding microparticle 1520 therein may be designated as a reaction site that includes the transferred biomolecules. The transferred biomolecules in each recess 1524 may be identified by correlating the identification codes of the microparticles 1520 with the associated biomolecules. When the recesses 1524 are designated as reaction sites, information regarding the biomolecules at each reaction site and a location of the reaction site may be stored in a database or other storage device/medium.

Thus, after processing the holder 1522 via the method 1500, the holder 1522 may constitute an array having different biomolecules at known spatial locations on the active side 1526. Although one example of immobilizing biomolecules to surfaces of the recesses 1524 has been provided above, the holder 1522 may be modified or processed in various manners as desired.

The method 1500 may also include, at 1512, performing an assay using the holder 1522 to obtain data on desired reactions. Various multiplex assays, such as those described above, may be performed using the processed holder 1522. For example, the biomolecules immobilized to the support surface 1530 may be released into the recesses 1524. In one particular embodiment, the biomolecules (e.g., primer sequences) that are immobilized to the support surface 1530 may include a photocleavable linker. When desired, the recesses 1524 may be illuminated with UV light to release the biomolecules into a surrounding solution. After or while the assay is performed, detection data, such as a detected level of fluorescence from each recess 1524, may be communicated to a system controller or module. The detection data obtained from each recess 1524 may be correlated to the biomolecules of the corresponding reaction site for subsequent analysis of, e.g., a target analyte.

Optionally, the microparticles 1520 may be re-loaded with biomolecules after being removed from the holder 1522, at 1514, or recycled to be used again in producing another microarray. For example, after the microparticles are removed at 1508, the microparticles 1520 may be pooled into a common solution and undergo various chemical reactions to attach the desired biomolecules to the microparticles. For example, PCR may be performed using the ssDNA attached to the microparticles 1520 as a template. In alternative embodiments, a different set or batch of microparticles may be provided to the holder 1522 that has already been processed through one iteration of the method 1500. The steps of the method 1500 may be repeated resulting in two rounds of transferring biomolecules from encoded microparticles into the recesses.

In the exemplary embodiment described with respect to FIGS. 40-45, the microparticles 1520 do not have reservoir cores. However, in alternative embodiments, the microvessels described herein may also be used to transfer biological or chemical substances to the recesses 1524 to prepare an array in a similar manner. For example, the microvessels may be used to deliver a large number of amplicons within the reservoir core to a corresponding recess.

Figure 46:
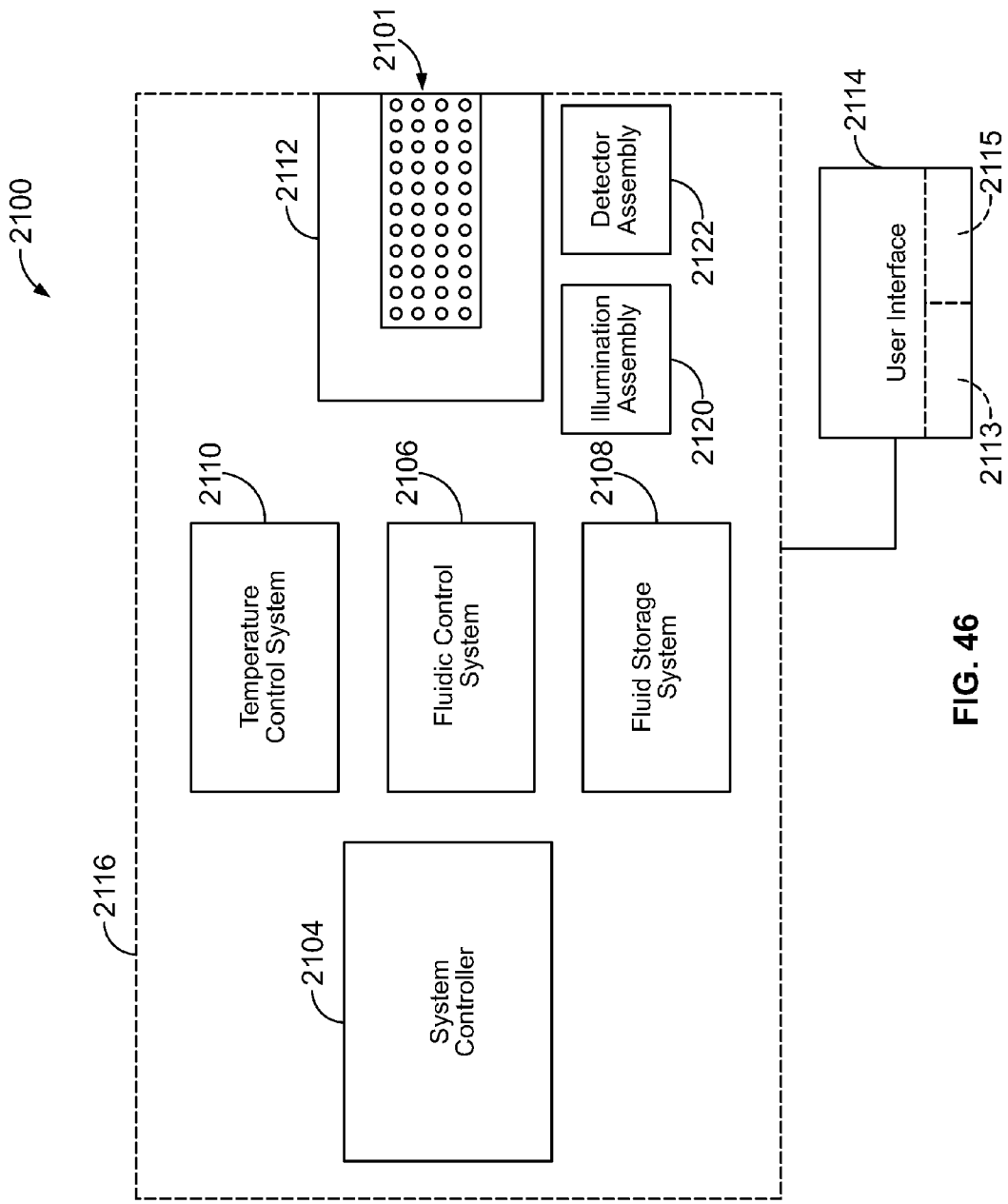
FIG. 46 is a schematic diagram of a system formed in accordance with one embodiment that may be used with various other embodiments described herein.

FIG. 46 is a block diagram of a system 2100 formed in accordance with one embodiment that may be used for biological or chemical analysis. In some embodiments, the system 2100 is a workstation that may be similar to a bench-top device or desktop computer. For example, a majority of the systems and components for conducting the desired reactions can be within a common housing 2116. The system 2100 is configured to receive an array holder 2102 to perform desired reactions within the holder 2102. In particular embodiments, the system 2100 is configured to perform massively parallel reactions with the holder 2102. The system 2100 may include the assemblies and components that are used to perform the methods 600, 1400, and 1500 described above. For example, the system 2100 may include the code excitation source 632, the fluorescent excitation source 634, the reader 642, the fluorescence detector 660, the container 650, and the computing device 664 of the system 601 that is described with respect to FIG. 28. U.S. Patent Application Publication No. 2006/0071075, which is incorporated by reference in the entirety, also describes optical readers that may be suitable for embodiments described herein. In addition, U.S. Pat. No. 7,745,091, which is incorporated by reference in the entirety, describes imaging systems that may be used with various embodiments.

The various components, assemblies, and systems (or subsystems) that interact with each other may perform a predetermined method or assay protocol for biological or chemical analysis. For example, the system 2100 includes a system controller 2104 that may communicate with the various components, assemblies, and sub-systems of the system 2100. For example, the system controller 2104 may communicate instructions for performing the various steps in the methods 600, 1400, and 1500. The system 2100 may also include a system receptacle or interface 2112 that engages the holder 2102; a fluidic control system 2106 to control the flow of fluid throughout a fluid network of the system 2100 and the holder 2102; a fluid storage system 2108 that is configured to hold all fluids and waste that may be used by the system 2100; and a temperature control system 2110 that may regulate the temperature of the fluid in the fluid network, the fluid storage system 2108, and/or the holder 2102.

In addition, the system 2100 may include an illumination assembly 2120 having one or more light sources (e.g., lasers). For example, the illumination assembly 2120 may include a code-reading beam that interrogates the encoded microparticles described herein. The illumination assembly 2120 may also include one or more excitation beams that may be used to excite labels attached to samples in the holder 2102. The system 2100 may also include a detector assembly 2122 having one or more detectors. The detector assembly 2122 may include code-reading detectors (e.g., CCDs) that are configured to detect output light patterns from microparticles. The detector assembly 2122 may also include activity detectors (CCDs or PMTs). The activity detectors may be used to, for example, detect fluorescence that is emanating from the samples.

Also shown, the system 2100 may include a user interface 2114 that interacts with the user. For example, the user interface 2114 may include a display 2113 to display or request information from a user and a user input device 2115 to receive user inputs. In some embodiments, the display 2113 and the user input device 2115 are the same device (e.g., touchscreen). As will be discussed in greater detail below, the system 2100 may communicate with various components of the primary systems 2106, 2108, and 2110 to perform predetermined protocols. The system 2100 may also be configured to analyze any detection data to provide a user with desired information.

The system controller 2104 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not intended to limit in any way the definition and/or meaning of the term system controller. In the exemplary embodiment, the system controller 2104 executes a set of instructions that are stored in one or more storage elements, memories, or modules in order to at least one of obtain and analyze detection data. Storage elements may be in the form of information sources or physical memory elements within the system 2100.

The system controller 2104 may include various modules for performing the assays and protocols described herein. For example, the system controller 2104 may include an illumination module that communicates with the illumination assembly 2120. For example, the illumination module may issue commands for directing a code-reading beam or fluorescence excitation beam onto the microparticles. The system controller 2104 may also include a detection module that communicates with the detector assembly and an analysis module. The analysis module may receive data regarding the determined identification codes in the recesses, the biomolecules associated with each identification code, and also detection data that is obtained from the samples. The data may be analyzed to provide information to a user of the system 2100.

The set of instructions may include various commands that instruct the system 2100 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the system 2100, processed in response to user inputs, or processed in response to a request made by another processing machine (e.g., a remote request through a communication link).

The system controller 2104 may be connected to other components of the system 2100 via communication links.

The system controller 2104 may also be communicatively connected to off-site systems or servers. The communication links may be hardwired or wireless. The system controller 2104 may receive user inputs or commands, from the user interface 2114.

The fluidic control system 2106 includes a fluid network and is configured to direct and regulate the flow of one or more fluids through the fluid network. The fluid network may be in fluid communication with the holder 2102 and the fluid storage system 2108. The temperature control system 2110 is configured to regulate the temperature of fluids at different regions of the fluid network, the fluid storage system 2108, and/or the holder 2102. The fluid storage system 2108 is in fluid communication with the holder 2102 and may store various reaction components or reactants that are used to conduct the desired reactions therein. The fluid storage system 2108 may also store fluids for washing or cleaning the fluid network and holder 2102. For example, the fluid storage system 2108 may include various reservoirs to store reagents, enzymes, other biomolecules, buffer solutions, aqueous, and non-polar solutions, and the like. Furthermore, the fluid storage system 2108 may also include waste reservoirs for receiving waste products from the holder 2102.

The system receptacle or interface 112 is configured to engage the holder 2102 in at least one of a mechanical, electrical, and fluidic manner. The system receptacle 2112 may hold the holder 2102 in a desired orientation to facilitate detection of codes or desired reactions. In addition, the system 2100 may communicate remotely with other systems or networks. Detection data obtained by the system 2100 may be stored in a remote database.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the specific components and processes described herein are intended to define the parameters of the various embodiments of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A plurality of isolated microvessels comprising:
   (a) a plurality of encoded microvessels each comprising a microbody and a reservoir cavity in the microbody, wherein the microbody separates a biological or chemical substance in the reservoir cavity from an ambient environment surrounding the microbody, the microbody comprising a transparent material that facilitates detection of an optical characteristic of the substance within the reservoir cavity, wherein the microbody of each microvessel further includes an identifiable code that distinguishes individual microvessels of the plurality of encoded microvessels from each other, wherein each of the microbodies has an elongated structure that extends lengthwise between opposite ends of the corresponding microbody and includes an inner coding region that surrounds the reservoir cavity and an outer region that surrounds the inner coding region, the inner coding region having the identifiable code of the corresponding microbody formed therein; and
   (b) a plurality of compartments each configured to separate individual microvessels of the plurality of encoded microvessels from each other.

2. The plurality of isolated microvessels according to claim 1 wherein the plurality of compartments comprise a plurality of micelles in an emulsion, each micelle of the plurality of micelles including only one of the microvessels.

3. The plurality of isolated microvessels according to claim 1 wherein the compartment is a well having a volume that accommodates no more than a single microvessel.

4. The plurality of isolated microvessels according to claim 1 wherein the reservoir cavities comprise nucleic acid templates that are separated from the ambient environment surrounding each microbody and wherein the ambient environment surrounding each microbody comprises one or more substances in common selected from the group consisting of a polymerase, a nucleic acid primer that is complementary to the template, and one or more nucleotides.

5. The plurality of isolated microvessels according to claim 1 wherein the reservoir cavity of each of the different microvessels comprises a predefined concentration of the biological or chemical substance.

6. The plurality of isolated microvessels according to claim 5, wherein the identifiable code distinguishes the concentration of each said biological or chemical substance.

7. The plurality of isolated microvessels according to claim 5, wherein the different microvessels produce a predetermined set of optical signals, thereby forming a reference standard.

8. The plurality of isolated microvessels in accordance with claim 1 wherein the reservoir cavities include a solid or semi-solid material for holding the substance, the material comprising a light-cured photopolymer that is different from the transparent material of the microbody.

9. The plurality of isolated microvessels according to claim 1, wherein the microbodies have the same size and structure and the reservoir cavities occupy the same position within the corresponding microbodies, each of the microbodies defining an opening to the corresponding reservoir cavity, the opening being sealed with a material that separates the biological or chemical substance in the reservoir cavity from the ambient environment surrounding the microbody.

10. The plurality of isolated microvessels according to claim 1, wherein the microbody defines only a single space that includes the reservoir cavity.

11. The plurality of isolated microvessels according to claim 1, wherein a central axis extends through the elongated structure between the opposite ends, the reservoir cavity extending parallel to and coinciding with the central axis.

12. The plurality of isolated microvessels according to claim 1, wherein the microbody has first and second openings to the reservoir cavity, the first and second openings being sealed with a material that separates the biological or chemical substance in the reservoir cavity from the ambient environment surrounding the microbody.

13. The plurality of isolated microvessels according to claim 1, wherein the microbody has first and second openings to the reservoir cavity, and wherein the reservoir cavity has a linear path as the reservoir cavity extends from the first opening to the second opening.

14. The plurality of isolated microvessels according to claim 13, wherein the linear path extends along an axis, the reservoir cavity having a cross-section taken transverse to the axis that is uniform along the linear path.

15. The plurality of isolated microvessels according to claim 1, wherein the reservoir cavities of the microbodies have the same shape.

16. The plurality of isolated microvessels according to claim 1, wherein a material of the microbody forms the identifiable code within the microbody.

17. The plurality of microvessels according to claim 1, wherein each of the outer region and the inner coding region has an index of refraction, the index of refractions of the outer region and the inner coding region being different.

18. The plurality of microvessels according to claim 1, wherein the inner coding region comprises a photosensitive material.

19. A method of providing an array having biomolecules at known locations, the method comprising:
(a) providing the plurality of isolated microvessels of claim 1;
(b) determining the identifiable codes of the microvessels within the corresponding compartments; and
(c) designating the compartments as reaction sites that include the biomolecules associated with the identifiable codes of the corresponding microvessels thereby providing an array of biomolecules at known locations.

20. The method in accordance with claim 19 further comprising releasing the biomolecules from the microvessels into the corresponding compartments.

21. The method in accordance with claim 20 wherein the releasing comprises providing a catalyst for performing click chemistry, the released biomolecules being immobilized to surfaces of the corresponding compartments.

\* \* \* \* \*